US009956263B2

(12) United States Patent
Nam et al.

(10) Patent No.: US 9,956,263 B2

(45) Date of Patent: May 1, 2018

(54) COMPOSITION FOR IMPROVING SKIN CONDITIONS COMPRISING A FRAGMENT OF HUMAN HEAT SHOCK PROTEIN 90A AS AN ACTIVE INGREDIENT

(71) Applicant: REGERON, INC., Chuncheon-si, Gangwon-do (KR)

(72) Inventors: Kibum Nam, Chuncheon-si (KR); Kyunyoung Lee, Chuncheon-si (KR); Youngwook Cho, Chuncheon-si (KR); Dahlkyun Oh, Chuncheon-si (KR)

(73) Assignee: REGERON, INC., Chuncheon (KR)

( * ) Notice: Subject to any disclaimer, the term of this patent is extended or adjusted under 35 U.S.C. 154(b) by 0 days. days.

(21) Appl. No.: 14/911,215

(22) PCT Filed: Aug. 11, 2014

(86) PCT No.: PCT/KR2014/007430

§ 371 (c)(1),
(2) Date: Jun. 20, 2016

(87) PCT Pub. No.: WO2015/020499

PCT Pub. Date: Feb. 12, 2015

(65) Prior Publication Data

US 2017/0087211 A1 Mar. 30, 2017

(30) Foreign Application Priority Data

Aug. 9, 2013 (KR) ........................ 10-2013-0094930

(51) Int. Cl.

| | |
|---|---|
| ***C07K 1/00*** | (2006.01) |
| ***A61K 38/00*** | (2006.01) |
| ***A61K 38/17*** | (2006.01) |
| ***A61K 9/127*** | (2006.01) |
| ***A61K 9/00*** | (2006.01) |
| ***A61K 47/10*** | (2017.01) |
| ***A61K 47/32*** | (2006.01) |
| ***A61K 8/64*** | (2006.01) |
| ***A61Q 19/02*** | (2006.01) |
| ***A61Q 19/06*** | (2006.01) |
| ***A61Q 19/08*** | (2006.01) |
| ***A61K 8/14*** | (2006.01) |

(52) U.S. Cl.

CPC ............ *A61K 38/1709* (2013.01); *A61K 8/14* (2013.01); *A61K 8/64* (2013.01); *A61K 9/0014* (2013.01); *A61K 9/127* (2013.01); *A61K 47/10* (2013.01); *A61K 47/32* (2013.01); *A61Q 19/02* (2013.01); *A61Q 19/06* (2013.01); *A61Q 19/08* (2013.01)

(58) Field of Classification Search

None

See application file for complete search history.

(56) References Cited

U.S. PATENT DOCUMENTS

| | | | | |
|---|---|---|---|---|
| 2007/0081963 A1* | 4/2007 | Oh | .......................... | A61K 8/14 424/70.14 |
| 2008/0213346 A1 | 9/2008 | Oh et al. | | |
| 2009/0053314 A1 | 2/2009 | Pyo et al. | | |
| 2011/0021435 A1 | 1/2011 | Lee et al. | | |
| 2011/0082082 A1* | 4/2011 | Li | .......................... | C07K 14/47 514/9.4 |
| 2011/0318400 A1* | 12/2011 | Lax | .......................... | A61K 8/64 424/401 |
| 2014/0073576 A1 | 3/2014 | Lee et al. | | |

FOREIGN PATENT DOCUMENTS

| | | |
|---|---|---|
| CA | 2924146 A1 | 2/2015 |
| EP | 3030253 A1 | 6/2016 |

OTHER PUBLICATIONS

Berke et al., Atopic Dermatitis: An Overview, American Family Physician, 2012, pp. 35-42, vol. 86, Issue 1, American Academy of Family Physicians.

Bolinder et al., Site Differences in Insulin Receptor Binding and Insulin Action in Subcutaneous Fat of Obese Females, Journal of Clinical Endocrinology and Metabolism, 1983, pp. 455-461, vol. 57, Issue 3, The Endocrine Society.

Bos et al., The 500 Dalton rule for the skin penetration of chemical compounds and drugs, Experimental Dermatology, 2000, pp. 165-169, vol. 9, Munksgaard.

Capristo et al., Environmental prevention in atopic eczema dermatitis syndrome (AEDS) and asthma: avoidance of indoor allergens, Allergy, 2004, pp. 53-60, vol. 59, Suppl. 78, Blackwell Munksgaard.

Cheng et al., A fragment of secreted Hsp90α carries properties that enable it to accelerate effectively both acute and diabetic wound healing in mice, The Journal of Clinical Investigation, Nov. 2011, pp. 4348-4361, vol. 121, Issue 11.

(Continued)

*Primary Examiner* — Shulamith H Shafer

(74) *Attorney, Agent, or Firm* — Denise L. Mayfield; Husch Blackwell LLP

(57) ABSTRACT

Liposomal and/or nano-liposomal encapsulated HSP90a, HPf polypeptide (115 aa) and novel polypeptides HPf ΔC1 (101 aa) and HPfΔC2 (87 aa), as well as methods for manufacturing/preparing and using the compositions, are disclosed. Chimeric fusion proteins that include an HSP90a, HPf-polypeptide, HPf ΔC1 or HPfΔC2 polypeptide are presented. Transformed cell lines and expression vectors capable of expressing the chimeric fusion proteins, are provided. Methods for producing large amounts of recombinant HSP90a, HPf polypeptide, HPf ΔC1 or HPfΔC2 polypeptide, using expression vectors and transformed cell lines, are described. Topical and other delivery form preparations and methods for using the preparations, including methods for improving skin conditions (atopic dermatitis, wrinkles, skin elasticity, dark spots (over pigmentation), overall skin rejuvenation, skin ageing) for therapeutic and cosmeceutical uses are presented. Liposomal preparations and methods for using them for enhancing wound healing and methods for suppressing subcutaneous fat cell differentiation and reducing subcutaneous fat formation are disclosed.

21 Claims, 27 Drawing Sheets

(56) References Cited

OTHER PUBLICATIONS

Dhingra et al., Mechanisms of Contact Sensitization Offer Insights into the Role of Barrier Defects vs. Intrinsic Immune Abnormalities as Drivers of Atopic Dermatitis, Journal of Investigative Dermatology, 2013, pp. 2311-2314, vol. 133.

Pockley, A. Graham, Heat shock proteins as regulators of the immune response, The Lancet, Aug. 9, 2003, pp. 469-476, vol. 362.

Schoop et al., Epideral Organization and Differentiation of HaCaT Keratinocytes in Organotypic Coculture with Human Dermal Fibroblasts, The Journal of Investigative Dermatology, 1999, pp. 343-353, vol. 112, The Society for Investigative Dermatology, Inc.

Van Noort et al., The link between small heat shock proteins and the immune system, The International Journal of Biochemistry & Cell Biology, 2012, pp. 1670-1679, vol. 44.

Subcutaneous Tissue, MeSH Descriptor Data 2017, 1 page, U.S. National Library of Medicine. Accessed Oct. 23, 2017.

Blommel et al., A Combined Approach to Improving Large-Scale Production of Tobacco Etch Virus Protease, Protein Expr Purif., Sep. 2007, pp. 53-68, vol. 55, Issue 1.

Lees-Miller et al., The Human Double-stranded DNA-activated Protein Kinase Phosphorylates the 90-kDa Heat-Shock Protein, hsp90α at Two NH2-terminal Threonine Residues, The Journal of Biological Chemistry, Oct. 15, 1989, pp. 17275-17280, vol. 264, Issue 29, Waverly Press, U.S.A.

PCT International Search Report for International application No. PCT/KR2014/007430, dated Nov. 7, 2014, 4 pages.

* cited by examiner

1. Competent cell (negative control)
2. TRX(TEVc)-HPfΔC1/2-overexpressed cell
3. Total cell lysate after homogenizat
4. Supernatant fraction after homogenization
5. Pellet after sonication (Inclusion body)

1. Competent cell (negative ctrl)
2. Total cell lysate
3. Pellet after sonication (Inclusion body)
4. Supernatant fraction after homogenization
5. Washing solution of the pellet 1. Protein marker
2. Competent cell (negative ctrl)
3. Total cell lysate
4. Supernatant fraction after homogenization
5. Pellet after sonication (Inclusion body)
6. Washing solution of the pellet
7. Solubilized inclusion body 8-11. Solubilized inclusion body + TEV protease Final refining yield : 0.1- 0.2 g/L

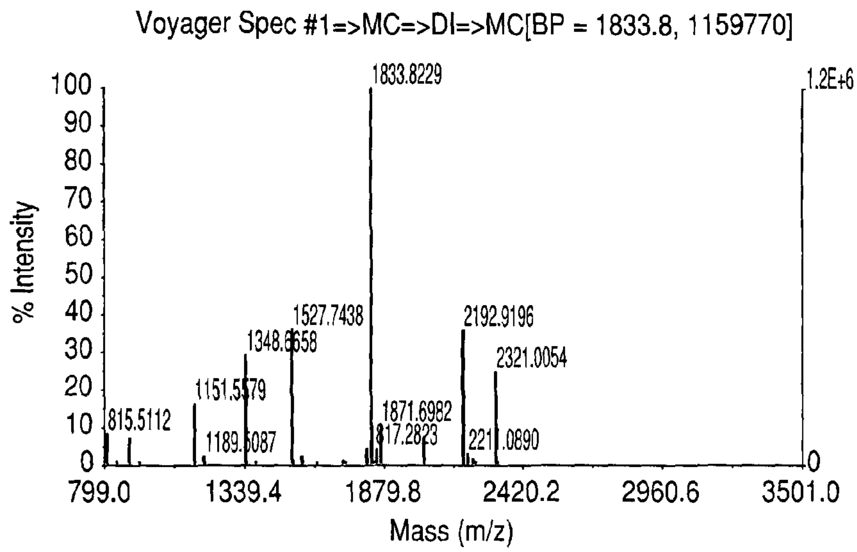

Fraction-Spot-Run ID: 1-1-1
MS-Fit search selects 3 entries.

[-] Results Summary

| Protein Hit Number | MOWSE Score | # pep # mat % mat 20 pks | % Cov | % TIC | Mean Err ppm | Data Tol ppm | # Hom Prot | MS-Digest Index# | Protein MW (Da)pI | Accession # | Species | Protein Name |
|---|---|---|---|---|---|---|---|---|---|---|---|---|
| 1 | 134023 | 8/8/40 | 11.2 | 40.0 | 1.94 | 17.1 | 1 | 166215 | 84660/4.9 | PO7900 | HUMAN | Heat shock protein HSP 90-alpha |
| 3 | 61.1 | 4/4/20 | 4.2 | 20.0 | 7.78 | 9.92 | No | 229426 | 123511/8.9 | Q6PKGO | HUMAN | La-related protein 1 |

| | | | | | | | | | | | | | | | | | | | | |
|---|---|---|---|---|---|---|---|---|---|---|---|---|---|---|---|---|---|---|---|---|
| 166215 | X | X | X | . | X | X | . | . | . | . | . | X | . | . | . | . | X | . | . | X |
| 229426 | . | . | X | . | . | . | . | . | X | . | . | . | . | . | . | . | X | . | . | X |

Similar Matched for Protein Hit 1

| Protein Hit Number | MOWSE Score | # pep # mat % mat 20 pks | % Cov | % TIC | Mean Err ppm | Data Tol ppm | # Hom Prot | MS-Digest Index# | Protein MW (Da)pI | Accession # | Species | Protein Name |
|---|---|---|---|---|---|---|---|---|---|---|---|---|
| 1 | 134023 | 8/8/40 | 11.2 | 40.0 | 1.94 | 17.1 | 1 | 166215 | 84660/4.9 | PO7900 | HUMAN | Heat shock protein HSP 90-alpha |

| Protein Hit Number | MOWSE Score | # pep # mat % mat 20 pks | % Cov | % TIC | Mean Err ppm | Data Tol ppm | # Hom Prot | MS-Digest Index# | Protein MW (Da)pI | Accession # | Species | Protein Name |
|---|---|---|---|---|---|---|---|---|---|---|---|---|
| 2 | 182 | 5/5/25 | 8.1 | 25.0 | -1.78 | 8.53 | 4 | 61540 | 83265/5.0 | PO8238 | HUMAN | Heat shock protein HSP 90-alpha |

FIG. 8

No DNFB

DNFB Only

DNFB+control

DNFB+ HPf

No treatment-1

DNFB only-1

DNFB + Control-1

DNFB + HPf-1

No treatment-2

DNFB only-2

DNFB + Control-2

DNFB + HPf-2

FIG. 17A-C-1 FIG. 17A-C-2 FIG. 17A-C-3
Control
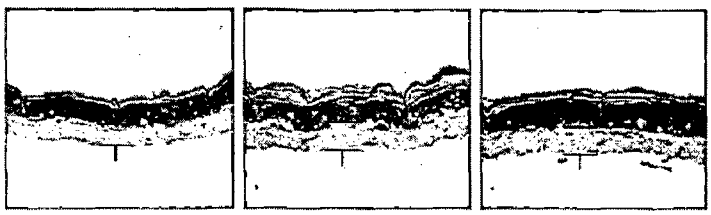
HPf
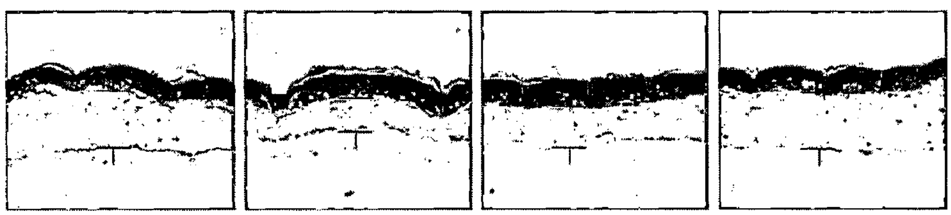
FIG. 17B-H-1 FIG. 17B-H-2 FIG. 17B-H-3 FIG. 17B-H-4
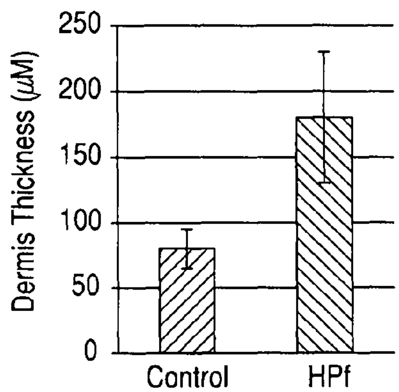
FIG. 17C

SEQUENCE LISTING

```
<160> NUMBER OF SEQ ID NOS: 33

<210> SEQ ID NO 1
<211> LENGTH: 115
<212> TYPE: PRT
<213> ORGANISM: Artificial Sequence
<220> FEATURE:
<223> OTHER INFORMATION: Amino acid sequence for HPf

<400> SEQUENCE: 1

Glu Glu Lys Glu Asp Lys Glu Glu Glu Lys Glu Lys Glu Glu Lys Glu
1               5                   10                  15

Ser Glu Asp Lys Pro Glu Ile Glu Asp Val Gly Ser Asp Glu Glu Glu
            20                  25                  30

Glu Lys Lys Asp Gly Asp Lys Lys Lys Lys Lys Lys Ile Lys Glu Lys
        35                  40                  45

Tyr Ile Asp Gln Glu Glu Leu Asn Lys Thr Lys Pro Ile Trp Thr Arg
    50                  55                  60

Asn Pro Asp Asp Ile Thr Asn Glu Glu Tyr Gly Glu Phe Tyr Lys Ser
65                  70                  75                  80
```

-continued

```
Leu Thr Asn Asp Trp Glu Asp His Leu Ala Val Lys His Phe Ser Val
                85                  90                  95

Glu Gly Gln Leu Glu Phe Arg Ala Leu Leu Phe Val Pro Arg Arg Ala
            100                 105                 110

Pro Phe Asp
        115


<210> SEQ ID NO 2
<211> LENGTH: 732
<212> TYPE: PRT
<213> ORGANISM: Artificial Sequence
<220> FEATURE:
<223> OTHER INFORMATION: Full amino acid sequence for HSP90a

<400> SEQUENCE: 2

Met Pro Glu Glu Thr Gln Thr Gln Asp Gln Pro Met Glu Glu Glu Glu
1               5                   10                  15

Val Glu Thr Phe Ala Phe Gln Ala Glu Ile Ala Gln Leu Met Ser Leu
            20                  25                  30

Ile Ile Asn Thr Phe Tyr Ser Asn Lys Glu Ile Phe Leu Arg Glu Leu
        35                  40                  45

Ile Ser Asn Ser Ser Asp Ala Leu Asp Lys Ile Arg Tyr Glu Ser Leu
    50                  55                  60

Thr Asp Pro Ser Lys Leu Asp Ser Gly Lys Glu Leu His Ile Asn Leu
65                  70                  75                  80

Ile Pro Asn Lys Gln Asp Arg Thr Leu Thr Ile Val Asp Thr Gly Ile
                85                  90                  95

Gly Met Thr Lys Ala Asp Leu Ile Asn Asn Leu Gly Thr Ile Ala Lys
            100                 105                 110

Ser Gly Thr Lys Ala Phe Met Glu Ala Leu Gln Ala Gly Ala Asp Ile
        115                 120                 125

Ser Met Ile Gly Gln Phe Gly Val Gly Phe Tyr Ser Ala Tyr Leu Val
    130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
            180                 185                 190

Asp Gln Thr Glu Tyr Leu Glu Glu Arg Arg Ile Lys Glu Ile Val Lys
        195                 200                 205

Lys His Ser Gln Phe Ile Gly Tyr Pro Ile Thr Leu Phe Val Glu Lys
    210                 215                 220

Glu Arg Asp Lys Glu Val Ser Asp Asp Glu Ala Glu Glu Lys Glu Asp
225                 230                 235                 240

Lys Glu Glu Glu Lys Glu Lys Glu Glu Lys Glu Ser Glu Asp Lys Pro
                245                 250                 255

Glu Ile Glu Asp Val Gly Ser Asp Glu Glu Glu Glu Lys Lys Asp Gly
            260                 265                 270

Asp Lys Lys Lys Lys Lys Lys Ile Lys Glu Lys Tyr Ile Asp Gln Glu
        275                 280                 285

Glu Leu Asn Lys Thr Lys Pro Ile Trp Thr Arg Asn Pro Asp Asp Ile
    290                 295                 300

Thr Asn Glu Glu Tyr Gly Glu Phe Tyr Lys Ser Leu Thr Asn Asp Trp
305                 310                 315                 320
```

-continued

```
Glu Asp His Leu Ala Val Lys His Phe Ser Val Glu Gly Gln Leu Glu
                325                 330                 335

Phe Arg Ala Leu Leu Phe Val Pro Arg Arg Ala Pro Phe Asp Leu Phe
            340                 345                 350

Glu Asn Arg Lys Lys Lys Asn Asn Ile Lys Leu Tyr Val Arg Arg Val
        355                 360                 365

Phe Ile Met Asp Asn Cys Glu Glu Leu Ile Pro Glu Tyr Leu Asn Phe
    370                 375                 380

Ile Arg Gly Val Val Asp Ser Glu Asp Leu Pro Leu Asn Ile Ser Arg
385                 390                 395                 400

Glu Met Leu Gln Gln Ser Lys Ile Leu Lys Val Ile Arg Lys Asn Leu
                405                 410                 415

Val Lys Lys Cys Leu Glu Leu Phe Thr Glu Leu Ala Glu Asp Lys Glu
            420                 425                 430

Asn Tyr Lys Lys Phe Tyr Glu Gln Phe Ser Lys Asn Ile Lys Leu Gly
        435                 440                 445

Ile His Glu Asp Ser Gln Asn Arg Lys Lys Leu Ser Glu Leu Leu Arg
    450                 455                 460

Tyr Tyr Thr Ser Ala Ser Gly Asp Glu Met Val Ser Leu Lys Asp Tyr
465                 470                 475                 480

Cys Thr Arg Met Lys Glu Asn Gln Lys His Ile Tyr Tyr Ile Thr Gly
                485                 490                 495

Glu Thr Lys Asp Gln Val Ala Asn Ser Ala Phe Val Glu Arg Leu Arg
            500                 505                 510

Lys His Gly Leu Glu Val Ile Tyr Met Ile Glu Pro Ile Asp Glu Tyr
        515                 520                 525

Cys Val Gln Gln Leu Lys Glu Phe Glu Gly Lys Thr Leu Val Ser Val
    530                 535                 540

Thr Lys Glu Gly Leu Glu Leu Pro Glu Asp Glu Glu Glu Lys Lys Lys
545                 550                 555                 560

Gln Glu Glu Lys Lys Thr Lys Phe Glu Asn Leu Cys Lys Ile Met Lys
                565                 570                 575

Asp Ile Leu Glu Lys Lys Val Glu Lys Val Val Val Ser Asn Arg Leu
            580                 585                 590

Val Thr Ser Pro Cys Cys Ile Val Thr Ser Thr Tyr Gly Trp Thr Ala
        595                 600                 605

Asn Met Glu Arg Ile Met Lys Ala Gln Ala Leu Arg Asp Asn Ser Thr
    610                 615                 620

Met Gly Tyr Met Ala Ala Lys Lys His Leu Glu Ile Asn Pro Asp His
625                 630                 635                 640

Ser Ile Ile Glu Thr Leu Arg Gln Lys Ala Glu Ala Asp Lys Asn Asp
                645                 650                 655

Lys Ser Val Lys Asp Leu Val Ile Leu Leu Tyr Glu Thr Ala Leu Leu
            660                 665                 670

Ser Ser Gly Phe Ser Leu Glu Asp Pro Gln Thr His Ala Asn Arg Ile
        675                 680                 685

Tyr Arg Met Ile Lys Leu Gly Leu Gly Ile Asp Glu Asp Asp Pro Thr
    690                 695                 700

Ala Asp Asp Thr Ser Ala Ala Val Thr Glu Glu Met Pro Pro Leu Glu
705                 710                 715                 720

Gly Asp Asp Asp Thr Ser Arg Met Glu Glu Val Asp
                725                 730
```

<210> SEQ ID NO 3
<211> LENGTH: 351
<212> TYPE: DNA
<213> ORGANISM: Artificial Sequence
<220> FEATURE:
<223> OTHER INFORMATION: Base sequence for HPf

<400> SEQUENCE: 3
atggaagaaa aggaagacaa agaagaagaa aaagaaaaag aagagaaaga gtcggaagac 60
aaacctgaaa ttgaagatgt tggttctgat gaggaagaag aaaagaagga tggtgacaag 120
aagaagaaga agaagattaa ggaaaagtac atcgatcaag aagagctcaa caaaacaaag 180
cccatctgga ccagaaatcc cgacgatatt actaatgagg agtacggaga attctataag 240
agcttgacca atgactggga agatcacttg gcagtgaagc atttttcagt tgaaggacag 300
ttggaattca gagcccttct atttgtccca cgacgtgctc cttttgatta a 351

<210> SEQ ID NO 4
<211> LENGTH: 37
<212> TYPE: DNA
<213> ORGANISM: Artificial Sequence
<220> FEATURE:
<223> OTHER INFORMATION: Base Sequence for PCR primer HPf -up

<400> SEQUENCE: 4
gagacatatg gaagaaaagg aagacaaaga agaagaa 37

<210> SEQ ID NO 5
<211> LENGTH: 38
<212> TYPE: DNA
<213> ORGANISM: Artificial Sequence
<220> FEATURE:
<223> OTHER INFORMATION: Base sequence for PCR primer HPf-dn

<400> SEQUENCE: 5
tataggtacc ttaatcaaaa ggagcacgtc gtgggaca 38

<210> SEQ ID NO 6
<211> LENGTH: 33
<212> TYPE: DNA
<213> ORGANISM: Artificial Sequence
<220> FEATURE:
<223> OTHER INFORMATION: Base sequence for PCR primer HPf delta C1-dn

<400> SEQUENCE: 6
ggggtacctc attccaactg tccttcaact gaa 33

<210> SEQ ID NO 7
<211> LENGTH: 33
<212> TYPE: DNA
<213> ORGANISM: Artificial Sequence
<220> FEATURE:
<223> OTHER INFORMATION: Base sequence for PCR primer HPf delta C2-dn

<400> SEQUENCE: 7
ggggtacctc aatcttccca gtcattggtc aag 33

<210> SEQ ID NO 8
<211> LENGTH: 31
<212> TYPE: DNA
<213> ORGANISM: Artificial Sequence
<220> FEATURE:
<223> OTHER INFORMATION: Base sequence for PCR primer TRX-up

<400> SEQUENCE: 8

```
ttaattcata tgagcgataa aattattcac c                                 31


<210> SEQ ID NO 9
<211> LENGTH: 19
<212> TYPE: DNA
<213> ORGANISM: Artificial Sequence
<220> FEATURE:
<223> OTHER INFORMATION: Base sequence for PCR primer TRX-NGc-dn

<400> SEQUENCE: 9

accgtttttg aacagcagc                                               19


<210> SEQ ID NO 10
<211> LENGTH: 48
<212> TYPE: DNA
<213> ORGANISM: Artificial Sequence
<220> FEATURE:
<223> OTHER INFORMATION: Base sequence for PCR primer TRX-TEVc-dn

<400> SEQUENCE: 10

ctggaagtac aggttttcgg atccattacc gtttttgaac agcagcag               48


<210> SEQ ID NO 11
<211> LENGTH: 46
<212> TYPE: DNA
<213> ORGANISM: Artificial Sequence
<220> FEATURE:
<223> OTHER INFORMATION: Base sequence for PCR primer HPf-NGc-up

<400> SEQUENCE: 11

gctgctgttc aaaaacggtg aagaaaagga agacaaagaa gaagaa                 46


<210> SEQ ID NO 12
<211> LENGTH: 54
<212> TYPE: DNA
<213> ORGANISM: Artificial Sequence
<220> FEATURE:
<223> OTHER INFORMATION: Base sequence for PCR primer HPf-TEVc-up

<400> SEQUENCE: 12

ggatccgaaa acctgtactt ccagggtgaa gaaaaggaag acaaagaaga agaa         54


<210> SEQ ID NO 13
<211> LENGTH: 31
<212> TYPE: DNA
<213> ORGANISM: Artificial Sequence
<220> FEATURE:
<223> OTHER INFORMATION: Base sequence for PCR primer HGH-Nde-up

<400> SEQUENCE: 13

gagacatatg ttcccgacca tcccgctgtc t                                 31


<210> SEQ ID NO 14
<211> LENGTH: 58
<212> TYPE: DNA
<213> ORGANISM: Artificial Sequence
<220> FEATURE:
<223> OTHER INFORMATION: Base sequence for PCR primer HGH-7His-dn

<400> SEQUENCE: 14

tttcggatcc agaaccatga tgatggtgat gatgatgacc gaagccacag ctgccctc     58


<210> SEQ ID NO 15
<211> LENGTH: 35
<212> TYPE: DNA
<213> ORGANISM: Artificial Sequence
```

<220> FEATURE:
<223> OTHER INFORMATION: Base sequence for PCR primer HSP90(full)-up

<400> SEQUENCE: 15
gagacatatg cctgaggaaa cccagaccca gaccc 35

<210> SEQ ID NO 16
<211> LENGTH: 35
<212> TYPE: DNA
<213> ORGANISM: Artificial Sequence
<220> FEATURE:
<223> OTHER INFORMATION: Base sequence for PCR primer HSP90(full)-dn

<400> SEQUENCE: 16
tataggtacc ttagtctact tcttccatgc gtgat 35

<210> SEQ ID NO 17
<211> LENGTH: 21
<212> TYPE: DNA
<213> ORGANISM: Artificial Sequence
<220> FEATURE:
<223> OTHER INFORMATION: Base sequence for PCR primer HSP90-5p(mid)

<400> SEQUENCE: 17
actggcggaa gataaagaga a 21

<210> SEQ ID NO 18
<211> LENGTH: 255
<212> TYPE: DNA
<213> ORGANISM: Artificial Sequence
<220> FEATURE:
<223> OTHER INFORMATION: Base sequence for TRX(NGc)

<400> SEQUENCE: 18
atgagcgata aaattattca cctgactgac gacagttttg acacggatgt actcaaagcg 60
gacggggcga tcctcgtcga tttctgggca gagtggtgcg gtccgtgcaa aatgatcgcc 120
ccgattctgg atgaaatcgc tgacgaatat cagggcaaac tgaccgttgc aaaactgaac 180
atcgatcaaa accctggcac tgcgccgaaa tatggcatcc gtggtatccc gactctgctg 240
ctgttcaaaa acggt 255

<210> SEQ ID NO 19
<211> LENGTH: 282
<212> TYPE: DNA
<213> ORGANISM: Artificial Sequence
<220> FEATURE:
<223> OTHER INFORMATION: Base sequence for TRX(TEVc)

<400> SEQUENCE: 19
atgagcgata aaattattca cctgactgac gacagttttg acacggatgt actcaaagcg 60
gacggggcga tcctcgtcga tttctgggca gagtggtgcg gtccgtgcaa aatgatcgcc 120
ccgattctgg atgaaatcgc tgacgaatat cagggcaaac tgaccgttgc aaaactgaac 180
atcgatcaaa accctggcac tgcgccgaaa tatggcatcc gtggtatccc gactctgctg 240
ctgttcaaaa acggtaatgg atccgaaaac ctgtacttcc ag 282

<210> SEQ ID NO 20
<211> LENGTH: 101
<212> TYPE: PRT
<213> ORGANISM: Artificial Sequence
<220> FEATURE:
<223> OTHER INFORMATION: Amino acid sequence for HPf delta C1

<400> SEQUENCE: 20

Glu Glu Lys Glu Asp Lys Glu Glu Glu Lys Glu Lys Glu Glu Lys Glu
1 5 10 15

Ser Glu Asp Lys Pro Glu Ile Glu Asp Val Gly Ser Asp Glu Glu Glu
20 25 30

Glu Lys Lys Asp Gly Asp Lys Lys Lys Lys Lys Lys Ile Lys Glu Lys
35 40 45

Tyr Ile Asp Gln Glu Glu Leu Asn Lys Thr Lys Pro Ile Trp Thr Arg
50 55 60

Asn Pro Asp Asp Ile Thr Asn Glu Glu Tyr Gly Glu Phe Tyr Lys Ser
65 70 75 80

Leu Thr Asn Asp Trp Glu Asp His Leu Ala Val Lys His Phe Ser Val
85 90 95

Glu Gly Gln Leu Glu
100

<210> SEQ ID NO 21
<211> LENGTH: 87
<212> TYPE: PRT
<213> ORGANISM: Artificial Sequence
<220> FEATURE:
<223> OTHER INFORMATION: Amino acid sequence for HPf delta C2

<400> SEQUENCE: 21

Glu Glu Lys Glu Asp Lys Glu Glu Glu Lys Glu Lys Glu Glu Lys Glu
1 5 10 15

Ser Glu Asp Lys Pro Glu Ile Glu Asp Val Gly Ser Asp Glu Glu Glu
20 25 30

Glu Lys Lys Asp Gly Asp Lys Lys Lys Lys Lys Lys Ile Lys Glu Lys
35 40 45

Tyr Ile Asp Gln Glu Glu Leu Asn Lys Thr Lys Pro Ile Trp Thr Arg
50 55 60

Asn Pro Asp Asp Ile Thr Asn Glu Glu Tyr Gly Glu Phe Tyr Lys Ser
65 70 75 80

Leu Thr Asn Asp Trp Glu Asp
85

<210> SEQ ID NO 22
<211> LENGTH: 309
<212> TYPE: DNA
<213> ORGANISM: Artificial Sequence
<220> FEATURE:
<223> OTHER INFORMATION: Base sequence for HPf delta C1

<400> SEQUENCE: 22
atggaagaaa aggaagacaa agaagaagaa aaagaaaaag aagagaaaga gtcggaagac 60
aaacctgaaa ttgaagatgt tggttctgat gaggaagaag aaaagaagga tggtgacaag 120
aagaagaaga agaagattaa ggaaaagtac atcgatcaag aagagctcaa caaaacaaag 180
cccatctgga ccagaaatcc cgacgatatt actaatgagg agtacggaga attctataag 240
agcttgacca atgactggga agatcacttg gcagtgaagc atttttcagt tgaaggacag 300
ttggaatga 309

<210> SEQ ID NO 23
<211> LENGTH: 267
<212> TYPE: DNA
<213> ORGANISM: Artificial Sequence
<220> FEATURE:

<223> OTHER INFORMATION: Base sequence for HPf delta C2

<400> SEQUENCE: 23
atggaagaaa aggaagacaa agaagaagaa aaagaaaaag aagagaaaga gtcggaagac 60
aaacctgaaa ttgaagatgt tggttctgat gaggaagaag aaaagaagga tggtgacaag 120
aagaagaaga agaagattaa ggaaaagtac atcgatcaag aagagctcaa caaaacaaag 180
cccatctgga ccagaaatcc cgacgatatt actaatgagg agtacggaga attctataag 240
agcttgacca atgactggga agattga 267

<210> SEQ ID NO 24
<211> LENGTH: 1527
<212> TYPE: DNA
<213> ORGANISM: Artificial Sequence
<220> FEATURE:
<223> OTHER INFORMATION: Base sequence for MBP(TEVc)-HPf

<400> SEQUENCE: 24
atgaaaatcg aagaaggtaa actggtaatc tggattaacg gcgataaagg ctataacggt 60
ctcgctgaag tcggtaagaa attcgagaaa gataccggca ttaaagtcac cgttgagcat 120
ccggataaac tggaagagaa attcccgcag gttgcggcaa ctggcgatgg ccctgacatt 180
atcttctggg cacacgaccg ctttggtggc tacgctcaaa gcggcctgtt ggctgaaatc 240
accccggaca aagcgttcca ggacaagctg tatccgttta cctgggatgc cgtacgttac 300
aacggcaagc tgattgctta cccgatcgct gttgaagcgt taagcctgat ttataacaaa 360
gacctgctgc cgaacccacc gaaaacctgg gaagagatcc cggcgctgga taaagaactg 420
aaagcgaaag gtaagagcgc gctgatgttc aacctgcaag aaccgtactt cacctggccg 480
ctgattgctg ctgacggggg ttatgcgttc aagtatgaaa acggcaagta cgacattaaa 540
gacgtgggcg tggataacgc tggcgcgaaa gcgggtctga ccttcctggt tgacctgatt 600
aaaaacaaac acatgaatgc agacaccgat tacagcatcg cagaagctgc ctttaataaa 660
ggcgaaacag cgatgaccat caacggcccg tgggcatgga gcaacatcga caccagcaaa 720
gtgaattatg gtgtaacggt actgccgacc ttcaagggtc aaccgtccaa accgttcgtt 780
ggcgtgctga gcgcaggtat taacgccgcc agcccgaaca aagagctggc aaaagagttc 840
ctcgaaaatt atctgctgac tgatgatggt ctggaagcgg ttaataaaga caaaccgctg 900
ggtgccgtag cgctgaagag ctacgaagaa gagttggtga atgatccgcg tattgccgcc 960
actatggaaa acgcccagaa aggtgaaatc atgccgatca tcccgcagat gagcgttttg 1020
tggtatgccg tgcgtactgc ggtgatcaac gccgccagcg gtcgtcagac tgtcgatgaa 1080
gccctgaaag acgcgcagac tatgattaac ggcgatggtg ctggtctgga agtgctgttt 1140
cagggtccgg agctaggatc cgaaaacctg tacttccagg gtgaagaaaa ggaagacaaa 1200
gaagaagaaa aagaaaaaga agagaaagag tcggaagacc aacaagaaat tgaagatgtt 1260
ggttctgatg aggaagaaga aaagaaggat ggtaacaaga agaagaagaa gattaaggaa 1320
aagtacatcg atcaagaaga gctcaacaaa acaaagccca tctggaccag aaatcccgac 1380
gatattacta atgaggagta cggagaattc tataagagct tgaccaatga ctgggaagat 1440
cacttggcag tgaagcattt ttcagttgaa ggacagttgg aattcagagc ccttctattt 1500
gtcccacgac gtgctccttt tgattaa 1527

<210> SEQ ID NO 25
<211> LENGTH: 981

<212> TYPE: DNA
<213> ORGANISM: Artificial Sequence
<220> FEATURE:
<223> OTHER INFORMATION: Base sequence for HGH(TEVc)-HPf

<400> SEQUENCE: 25

```
atgttcccga ccatcccgct gtctcgtctg tttgacaacg ctatgctccg cgcccatcgt     60

ctgcaccagc tggcctttga cacctaccag gagtttgaag aagcctatat cccaaaggaa    120

cagaagtatt cattcctgca gaacccccag acctccctct gtttctcaga gtctattccg    180

acaccctcca acagggagga aacacaacag aaatccaacc tagagctgct ccgcatctcc    240

ctgctgctca tccagtcgtg gctggagccc gtgcagttcc tcaggagtgt cttcgccaac    300

agcctggtgt acggcgcctc tgacagcaac gtctatgacc tcctaaagga cctagaggaa    360

ggcatccaaa cgctgatggg gaggctggaa gatggcagcc cccggactgg gcagatcttc    420

aagcagacct acagcaagtt cgacacaaac tcacacaacg atgacgcact actcaagaac    480

tacgggctgc tctactgctt caggaaggac atggacaagg tcgagacatt cctgcgcatc    540

gtgcagtgcc gctctgtgga gggcagctgt ggcttcggtc atcatcatca ccatcatcat    600

ggttctggat ccgaaaacct gtacttccag ggtgaagaaa aggaagacaa agaagaagaa    660

aaagaaaaag aagagaaaga gtcggaagac aaacctgaaa ttgaagatgt tggttctgat    720

gaggaagaag aaaagaagga tggtgacaag aagaagaaga agaagattaa ggaaaagtac    780

atcgatcaag aagagctcaa caaaacaaag cccatctgga ccagaaatcc cgacgatatt    840

actaatgagg agtacggaga attctataag agcttgacca atgactggga agatcacttg    900

gcagtgaagc atttttcagt tgaaggacag ttggaattca gagcccttct atttgtccca    960

cgacgtgctc cttttgatta a                                              981
```

<210> SEQ ID NO 26
<211> LENGTH: 2199
<212> TYPE: DNA
<213> ORGANISM: Artificial Sequence
<220> FEATURE:
<223> OTHER INFORMATION: Base sequence for HSP90a full CDS

<400> SEQUENCE: 26

```
atgcctgagg aaacccagac ccaagaccaa ccgatggagg aggaggaggt tgagacgttc     60

gcctttcagg cagaaattgc ccagttgatg tcattgatca tcaatacttt ctactcgaac    120

aaagagatct ttctgagaga gctcatttca aattcatcag atgcattgga caaaatccgg    180

tatgaaagct tgacagatcc cagtaaatta gactctggga aagagctgca tattaacctt    240

ataccgaaca aacaagatcg aactctcact attgtggata ctggaattgg aatgaccaag    300

gctgacttga tcaataacct tggtactatc gccaagtctg ggaccaaagc gttcatggaa    360

gctttgcagg ctggtgcaga tatctctatg attggccagt tcggtgttgg tttttattct    420

gcttatttgg ttgctgagaa agtaactgtg atcaccaaac ataacgatga tgagcagtac    480

gcttgggagt cctcagcagg gggatcattc acagtgagga cagacacagg tgaacctatg    540

ggtcgtggaa caaaagttat cctacacctg aaagaagacc aaactgagta cttggaggaa    600

cgaagaataa aggagattgt gaagaaacat tctcagttta ttggatatcc cattactctt    660

tttgtggaga aggaacgtga taaagaagta agcgatgatg aggctgaaga aaaggaagac    720

aaagaagaag aaaaagaaaa agaagagaaa gagtcggaag acaaacctga aattgaagat    780

gttggttctg atgaggaaga agaaaagaag gatggtgaca agaagaagaa gaagaagatt    840
```

-continued

```
aaggaaaagt acatcgatca agaagagctc aacaaaacaa agcccatctg gaccagaaat    900

cccgacgata ttactaatga ggagtacgga gaattctata agagcttgac caatgactgg    960

gaagatcact tggcagtgaa gcatttttca gttgaaggac agttggaatt cagagccctt   1020

ctatttgtcc cacgacgtgc tccttttgat ctgtttgaaa acagaaagaa aaagaacaac   1080

atcaaattgt atgtacgcag agttttcatc atggataact gtgaggagct aatccctgaa   1140

tatctgaact tcattagagg ggtggtagac tcggaggatc tccctctaaa catatcccgt   1200

gagatgttgc aacaaagcaa aattttgaaa gttatcagga agaatttggt caaaaaatgc   1260

ttagaactct ttactgaact ggcggaagat aaagagaact acaagaaatt ctatgagcag   1320

ttctctaaaa acataaagct tggaatacac gaagactctc aaaatcggaa gaagctttca   1380

gagctgttaa ggtactacac atctgcctct ggtgatgaga tggtttctct caaggactac   1440

tgcaccagaa tgaaggagaa ccagaaacat atctattata tcacaggtga gaccaaggac   1500

caggtagcta actcagcctt tgtggaacgt cttcggaaac atggcttaga agtgatctat   1560

atgattgagc ccattgatga gtactgtgtc caacagctga aggaatttga ggggaagact   1620

ttagtgtcag tcaccaaaga aggcctggaa cttccagagg atgaagaaga gaaaaagaag   1680

caggaagaga aaaaaacaaa gtttgagaac ctctgcaaaa tcatgaaaga catattggag   1740

aaaaaagttg aaaaggtggt tgtgtcaaac cgattggtga catctccatg ctgtattgtc   1800

acaagcacat atggctggac agcaaacatg gagagaatca tgaaagctca agccctaaga   1860

gacaactcaa caatgggtta catggcagca aagaaacacc tggagataaa ccctgaccat   1920

tccattattg agaccttaag gcaaaaggca gaggctgata agaacgacaa gtctgtgaag   1980

gatctggtca tcttgcttta tgaaactgcg ctcctgtctt ctggcttcag tctggaagat   2040

ccccagacac atgctaacag gatctacagg atgatcaaac ttggtctggg tattgatgaa   2100

gatgacccta ctgctgatga taccagtgct gctgtaactg aagaaatgcc acccccttgaa  2160

ggagatgacg acacatcacg catggaagaa gtagactaa                          2199
```

<210> SEQ ID NO 27
<211> LENGTH: 7
<212> TYPE: PRT
<213> ORGANISM: Artificial Sequence
<220> FEATURE:
<223> OTHER INFORMATION: TEV protease recognition sequence

<400> SEQUENCE: 27

```
Glu Asn Leu Tyr Phe Gln Gly
1               5
```

<210> SEQ ID NO 28
<211> LENGTH: 20
<212> TYPE: DNA
<213> ORGANISM: Artificial Sequence
<220> FEATURE:
<223> OTHER INFORMATION: Base sequence for PCR sense primer of KRT10

<400> SEQUENCE: 28

```
ggtgggagtt atggaggcag                                                 20
```

<210> SEQ ID NO 29
<211> LENGTH: 23
<212> TYPE: DNA
<213> ORGANISM: Artificial Sequence
<220> FEATURE:
<223> OTHER INFORMATION: Base sequence for PCR antisense primer of KRT10

-continued

```
<400> SEQUENCE: 29

cgaactttgt ccaagtagga agc                                          23


<210> SEQ ID NO 30
<211> LENGTH: 20
<212> TYPE: DNA
<213> ORGANISM: Artificial Sequence
<220> FEATURE:
<223> OTHER INFORMATION: Base sequence for PCR sense primer of TGM1

<400> SEQUENCE: 30

catcaagaat ggcctggtct                                              20


<210> SEQ ID NO 31
<211> LENGTH: 20
<212> TYPE: DNA
<213> ORGANISM: Artificial Sequence
<220> FEATURE:
<223> OTHER INFORMATION: Base sequence for PCR antisense primer of TGM1

<400> SEQUENCE: 31

caatcttgaa gctgccatca                                              20


<210> SEQ ID NO 32
<211> LENGTH: 22
<212> TYPE: DNA
<213> ORGANISM: Artificial Sequence
<220> FEATURE:
<223> OTHER INFORMATION: Base sequence for PCR sense primer of IVL

<400> SEQUENCE: 32

tcctccagtc aatacccatc ag                                           22


<210> SEQ ID NO 33
<211> LENGTH: 21
<212> TYPE: DNA
<213> ORGANISM: Artificial Sequence
<220> FEATURE:
<223> OTHER INFORMATION: Base sequence for PCR antisense primer of IVL

<400> SEQUENCE: 33

cagcagtcat gtgcttttcc t                                            21
```

COMPOSITION FOR IMPROVING SKIN CONDITIONS COMPRISING A FRAGMENT OF HUMAN HEAT SHOCK PROTEIN 90A AS AN ACTIVE INGREDIENT

SUBMISSION OF SEQUENCE LISTING

The contents of the electronic submission of the text file Sequence Listing, which is titled HB520756-6.txt, which was created on Oct. 25, 2016, and is 23 KB in size, is incorporated herein by reference in its entirety.

CROSS-REFERENCE TO RELATED APPLICATIONS

This is an International application filed with the Republic of Korea Receiving Office on Aug. 9, 2014. The present PCT application claims the benefit of priority to Republic of Korea patent application 10-2013-0094930, filed on Aug. 9, 2013.

BACKGROUND OF THE INVENTION

Technical Field

The present invention relates to compositions suitable for topical administration, the compositions comprising pharmacologically active polypeptides that are encapsulated in a liposome and/or nano-liposome. The invention also relates to methods of manufacturing the liposome and/or nano-liposome formulations. The invention further relates to methods for improving and/or treating skin conditions, enhancing wound healing, and for inhibiting subcutaneous fat formation.

Related Art

Heat Shock Protein 90a, abbreviated as HSP90a hereafter, is a dimer composed of two monomers containing phosphate groups, and having a molecular weight of 90 KD. The two monomers tend to become easily oligomerized under some conditions, e.g., when present in aqueous solution. Most Heat Shock Proteins have been known to function intracellularly. Other reports indicate that some Heat Shock Proteins work outside the cell, suggesting alternative physiological roles. The role of HSP90a in immune-regulation has been suggested[10, 12]. However, no systemic studies have been carried out with HSP90a, nor has it been described as having any activity for affecting skin conditions, such as atopic dermatitis or skin aging, or as affecting subcutaneous fat formation or accumulation. The relatively large size of the HSP90a fragment has precluded the use of this molecule in topical preparations, as it is unable to penetrate to the skin dermis layer[6].

Atopic dermatitis (AD) is a chronic dermal disorder caused by defects in stratum corneum, which is generally considered idiopathic[9]. It affects children and adults as well. Its epidemiology has been known to associate with hereditary[4] or environmental causes[7], and immunological factors[9].

There is no known cure for AD thus far, although treatments may reduce the severity and frequency of flares. Commonly used compositions for treating atopic dermatitis include small molecule based compounds with properties of anti-histamine, steroids or immune suppression. Alternatively systemic immune suppressing agents may be tried such as cyclosporine, methotrexate, interferon gamma-1b, mycophenolate mofetil and azathioprine[4]. However since these small-molecules based compounds accompany such serious adverse effects as deterioration of immune function upon long term use, new materials to overcome such barriers are needed in the treatment of these and other conditions.

Unlike small molecule based medicine, there are significant advantages in using a polypeptide as active ingredients for the treatment of dermal disorders and/or preparing skin cosmetic products. For example, polypeptides are generally more compatible with interactions with the immune system and cells, and generally decomposed in a pro-physiological manner within the body, hence generating fewer side effects compared to small molecule (chemical) containing preparations, especially during long term use. Furthermore, as relates to uses in cosmeceutical preparations, small molecule containing cosmetic products generally produce only short term cosmetic effects, while polypeptide containing cosmeceutical preparations have been described as providing longer term improvement of overall skin condition, and even skin rejuvenation[3]. However, the overall size and bulkiness of many potentially useful polypeptides prevents the penetration of these ingredients into skin tissues.

Traditionally, macromolecules having a molecular weight of 500 Daltons or more are considered too large to pass through the skin epidermis due to the skin keratin barrier[6]. Even when used with chemical penetration enhancers, macromolecules having a molecular weight of more than 2000 Daltons are considered practically implausible for topical use, as they are unable to penetrate the skin epidermis. Therefore, peptides developed as pharmaceutical/cosmetic ingredients have been limited to those having a much smaller size, such as a size of less than 10 amino acids (roughly about 1100 Daltons MW), so as to optimize the delivery of the active ingredient to the skin dermis. Thus, many potentially useful polypeptides having a size of 10 amino acids or greater have not been utilized in topical preparations. Delivery of an active ingredient, such as a polypeptide, to the skin dermis layer, is necessary to provide the most pharmaceutically meaningful outcomes with functional pharmaceutical/cosmetic preparations.

Liposome based delivery of human growth hormone (hGH), having a MW of 22,124 Daltons (191 amino acid size), has been reported[1-3]. However, challenges associated with effective topical delivery of other pharmacologically different peptides/proteins, such as heat shock protein Hsp90a, remain.

A 115 amino acid fragment of Heat Shock Protein, termed HPf, is encoded by an amino acid sequence spanning between the linker and the middle domain of the native endogenous HSP sequence (FIG. 1). This fragment has been reported to ameliorate skin necrosis caused by diabetic ulcer.[8] Improvements in delivery products are, however, lacking for facilitating fuller use and formulation of these and related polypeptides.

Subcutaneous fat is the layer of subcutaneous tissue that is most widely distributed and is mainly composed of adipocytes. The number of adipocytes varies among different areas of the body, while their size varies according to the body's nutritional state (Subcutaneous Tissue. Medical Subject Headings (MeSH). NLM Retrieved 5 Jun. 2013). Some reports suggest that reducing the size of fat cells could improve fat cell sensitivity to insulin[5]. Numerous small molecule based oral delivery medicines have been developed and marketed for suppressing the accumulation of fat. Oral administration of these types of preparations, however, is associated with adverse side effects. A topical preparation would be more effective in such applications, and would offer the advantage of targeting problem fat deposit areas on the body, among other advantages.

One of the many barriers in the use of polypeptides in topical preparations remains the size and bulkiness of these polypeptide and protein molecules, which, because of the structure of skin tissues, do not penetrate the skin sufficiently to provide beneficial pharmacological and physiological effects in the body. Conventional approaches to this problem have been the use of mesotherapeutic devices, such as micro needles, electroporation devices, laser treatments, and infrared irradiation. For a variety of reasons, these approaches have not provided a sufficiently effective and convenient approach for topical administration of peptide-containing preparations. Problems associated with sufficient shelf-life and product biological stability also limit the use of polypeptide/peptide/protein based topical and other preparations.

A need continues to exist in the medical arts for improved topical preparations with preserved bioactivity and enhanced shelf-life of identified polypeptide/protein-based molecules. In addition, a need continues to exist for achieving effective delivery of these and other potent polypeptide/protein agents deep into skin tissues to achieve maximal physiological benefit to the patient. The present invention provides a solution to these and other technical problems in the medical arts for the use of polypeptide and/or protein-based molecules in topical and other delivery formulation applications and treatment methods.

SUMMARY OF THE INVENTION

The present invention provides, for the first time, liposomal and nano-liposomal encapsulated Heat Shock Protein (HSP) preparations, as well as preparations that include smaller polypeptide fragments of HSP, namely HPf (115 aa), as well as novel polypeptides HPfΔC1 (101 aa), and HPfΔC2 (87 aa). The liposomal preparations are further demonstrated to possess a number of novel and advantageous physiological effects when delivered topically at the skin surface, including the enhancement of wound healing, the inhibition of fat cell differentiation, the improvement of skin conditions (including atopic dermatitis, wrinkle, skin elasticity and dark spots, and promoting overall skin rejuvenation) and effective delivery to skin hair follicles.

The polypeptide compositions and preparations may further be provided as nano-liposomal encapsulated preparations. These preparations are demonstrated to possess long term storage stability and retained bioactivity in solution. The preparations may be provided in a delivery form suitable for topical, mesotherapeutic or systemic administration.

Surprisingly, the present invention has accomplished the effective delivery of HPf, a 115 amino acid fragment of HSP90a, to the stratum corneum of both intact skin and wounded skin, using a topical formulation of the polypeptide in a liposome-based delivery preparation.

According to some aspects of the invention, a liposomal (particularly, a nano-liposomal) encapsulated polypeptide composition is provided comprising a Heat Shock Protein, and HPf polypeptide or fragment thereof, as an active ingredient. The HPf polypeptide fragment may comprise a polypeptide having a 115aa sequence (termed HPf) (SEQ ID. No. 1), a 101 aa sequence (HPfΔC1) (SEQ ID. NO. 20), an 87 aa sequence (HPfΔC2)(SEQ ID. NO. 21), an HSP90a aa sequence (SEQ. ID NO. 2), or a combination thereof. The composition, in some embodiments, is formulated so as to be suitable for topical application to the skin, and in particular, for use in the preparation of cosmeceutical preparations. (cosmetics, skin conditioners, and the like).

In particular embodiments, the nano-liposomes have a particle size of 50-500 nm, 50-350 nm, or 100-250 nm.

The present invention includes the discovery that HSP90a fragments, such as HPf, as well as synthetic polypeptide sequences that are unlike the native sequence, such as HPfΔC1 (101 aa), and HPfΔC2 (87 aa), promote the differentiation of the skin cells, both epidermal and dermal, while inhibiting the differentiation of preadipocytes at the subdermal layer. This activity, in turn, inhibits the progression and severity of atopic eczema and/or atopic dermatitis. This feature provides yet another objective of the present invention.

In another embodiment of the present invention, a composition is provided for use in a medicament for suppressing subcutaneous fat accumulation and fat cell differentiation.

In another aspect, the invention provides a method for reducing and/or inhibiting the accumulation of subcutaneous fat and/or suppressing subcutaneous fat cell differentiation is provided, the method comprising topically applying a nano-liposomal composition comprising a polypeptide having a sequence corresponding to a fragment of Heat Shock Protein. In some embodiments, the polypeptide is defined by a 115aa sequence (termed HPf) (SEQ ID. No. 1), a 101 aa sequence (HPfΔC1) (SEQ ID. NO. 20), an 87 aa sequence (HPfΔC2)(SEQ ID. NO. 21), or an HSP90a aa sequence (SEQ. ID NO. 2), the polypeptide being encapsulated in a nano-liposome.

In another aspect, the invention provides a nano-liposomal preparation for use in a medicament for treatment of obesity, cellulite, varicose veins of lower extremities with ulcer, lower body extremity edema, varicose veins, skin discoloration, venous eczema, scleroderma, inflammatory thrombus, skin ulcer, or chronic pain.

Yet another aspect of the invention provides for transformed cell lines useful in the production and/or manufacture of recombinant HSP90a and HPf polypeptides (HSP90a, HPf, HPfΔC1, HPfΔC2). By way of example, cell lines that may be used in the preparation of these transformed cell lines include a TOP10 cell line, a BL21(D3)pLys cell line, RosettaBlue(DE3) cell line, and RZ4500 cell line. Expression vectors that include a sequence encoding a fusion protein comprising the HSP90am HPf, and/or HPf polypeptide fragments, with a fusion partner protein/peptide, are also disclosed, and are useful in the large-scale and economical production of these useful therapeutic polypeptides. The fusion protein constructs are also defined as part of the present invention.

Another aspect of the invention provides for a method of manufacturing recombinant HSP90a and HPf polypeptides, including the HSP90a, HPf, HPfΔC1, and HPfΔC2 polypeptides.

Yet another aspect of the invention provides a topical liposomal polypeptide formulation containing HSP90a, an HPf polypeptide (HSP90a, HPf, HPfΔC1, HPfΔC2), or a combination thereof, for use in the treatment of a skin condition, wherein the skin condition is atopic dermatitis, wrinkles, dark spots, skin elasticity or skin aging, wherein said composition comprises a concentration of about 100 ng/ml to about 1 mg/ml of the HPf polypeptide or HPf polypeptide fragment.

Yet another aspect of the invention provides a topical liposomal polypeptide formulation containing HSP90a, an HPf polypeptide (HSP90a, HPf, HPfΔC1, HPfΔC2), or a combination thereof, for use in the treatment of subcutaneous fat accumulation, wherein said formulation comprises a concentration of about 100 ng/ml to about 1 mg/ml of the polypeptide.

The invention also provides for a use of a HSP90a, an HPf polypeptide or fragment thereof (HPfΔC1, HPfΔC2), or a combination thereof, in the manufacture of a preparation for the treatment of a skin condition, wherein the skin condition is atopic dermatitis, wrinkles, dark spots, skin elasticity or skin aging.

The invention also provides for a use of a HSP90a, an HPf polypeptide or fragment thereof (HPfΔC1, HPfΔC2), or a combination thereof in the manufacture of a preparation for the treatment of obesity, cellulite, varicose veins of lower extremities with ulcer, lower body extremity edema, varicose veins, skin discoloration, venous eczema, scleroderma, inflammatory thrombus, skin ulcer, or chronic pain.

BRIEF DESCRIPTION OF THE DRAWINGS

FIG. 2-1 shows the recombinant fusion protein constructs of HPf (A) and the fusion partner thioredoxin A (TRX), TRX(NGc)-HPf (B) and TRX(TEVc)-HPf(C), with the hydroxylamine and TEV protease recognition site respectively inserted in between the two, which is needed for facile cleavage and purification of HPf. FIG. 2-2 illustrates the structures of HPf Δ C1 (A), TRX(TEVc)-HPf Δ C1 (B), HPf Δ C2 (C) and TRX(TEVc)-HPf Δ C2 (D). The TEV protease recognition site was inserted after TRX, which is coupled with HPfΔC1 or HPfΔC2, in order to facilitate cleavage of the fusion proteins and purification of HPfΔC1 or HPfΔC2. FIG. 2-3 shows the recombinant fusion protein construct of the fusion partner maltose binding protein (MBP) and TEV including a His×6, MBP(TEVc)-His-TEV(A), and the recombinant fusion construct of MBP and HPf without the His×6, MBP(TEVc)-HPf (B). The TEV protease recognition site inserted in between each fusion construct is needed for facile cleavage and purification of TEV or HPf. FIG. 2-4 shows the recombinant fusion protein construct of HPf and the fusion partner human growth hormone (HGH), HGH (TEVc)-HPf, with the TEV protease recognition site inserted in between the two, which is needed for facile cleavage and purification of HPf. FIG. 2-5 shows the locations of the primers used for cloning the HSP90a gene (B) and the results of the PCR products amplified by said primers (A).

FIG. 3-1 is the result of the SDS-PAGE of the recombinant proteins HPf, TRX(NGc)-HPf, and TRX(TEVc)-HPf produced by expression of their recombinant expression vectors. The recombinant expression vector constructs were expressed in the RZ4500, BL21(DE3)pLyS, and RosettaBlue(DE3) cell lines to quantify the expression levels of these expression vector constructs. FIG. 3-2 is the result of the SDS-PAGE of the small-scale (5 ml) protein expression experiments relating to HPfΔC2, TRX(TEVc)-HPfΔC1 and TRX(TEVc)-HPfΔC2. FIG. 3-3 is the result of the SDS-PAGE of the recombinant protein MBP(TEVc)-HPf produced by expression of its recombinant expression vector. FIG. 3-4 is the result of the SDS-PAGE of the recombinant protein HGH(TEVc)-HPf produced by expression of its recombinant expression vector. FIG. 3-5 is the result of the SDS-PAGE of the HSP90a protein, produced by *e. coli* cells transformed by the HSP90a expression vector.

FIG. 8 describes the MALDI-TOF analysis results of the HPf protein confirming its aa sequence identity with HSP90a.

FIG. 9-1 is the ELS and GFC analysis results of purified HPf1 estimating masses, sizes, and numbers of different HPf1 aggregates formed during its purification. 9-1 (A) demonstrates the Ls int. Distribution (IS); 9-1(B) demonstrates the Wt. conv. Distribution (WT); 9-1 (C) demonstrates the No conv. Distribution (NO); 9-1 (D) demonstrates the GFC (Gel Filtration Chromatography) profile. FIG. 9-2 is a particle size analysis of HPf using TEM electron micrographs (EF-TEM; Energy Filtering-Transmission Electron Microscope, KBSI, Korea).

FIG. 10A-1 shows the effect of varying HPf concentration on 24-hour incubation survival rate of an keratinocyte cell-line (HaCaT) and FIGS. 10A-2, 10B-1, 10B-2, and 10B-3 show the effects of varying HPf concentrations on 24, 48, 120, and 168 hour incubation survival rates of embryonic fibroblast cells (HEF), respectively.

FIG. 13B-1 shows the condition of atopic dermatitis with no DNFB. FIG. 13B-2 shows the condition of atopic dermatitis with DNFB only, FIG. 13B-3 shows the condition of atopic dermatitis with DNFB+control, and FIG. 13 B-4 shows the condition of atopic dermatitis improved by topical administration of HPf on wounds induced by applying DNFB on the NC/Nga mouse skin.

FIG. 14A-1 demonstrates changes in the skin tissue structure with no treatment, 14A-2 with DNFB only treatment, 14A-3 with DNFB+Control-1, and 14A-4 with DNFB+HPf-1 treatment.

FIG. 17A (C-1, C-2, C-3)—Control; FIG. 17B (H-1, H-2, H-3, H-4)—topical HPf application to artificial human skin. FIG. 17C—graph showing HPf topical application promotes thickening of the dermis layer in the structure of artificial human skin.

DETAILED DESCRIPTION OF THE INVENTION

The present inventors have performed intensive research in the identification and manufacture of topical liposomal encapsulated HPf polypeptide and HPf polypeptide fragment compositions having potent pharmacological activity in vivo. The topical preparations include a polypeptide encoded by the amino acid at SEQ ID. No. 1, or a fragment thereof, as an active ingredient. The pharmacological activity of the compositions include improvement of skin conditions, including atopic dermatitis, wrinkles, dark spots, improving skin elasticity and skin rejuvenation, as well as enhancing wound healing. In addition, the compositions are also demonstrated to inhibit subcutaneous fat cell differentiation and to suppress the accumulation of subcutaneous fat.

The term 'human heat shock protein 90a fragment' or 'HSP90a fragment' represents the HSP90a of which partial sequences were removed by biochemical or DNA recombinant techniques. A polypeptide fragment of HSP90a is described as HPf herein. HPf is a 115 amino acid fragment of endogenous HSP90a, and is encoded by the sequence spanning from amino acid (aa) 236 to aa 350, including the "Linker" region (see FIG. 1). HPfΔC1 is the 101 amino acid fragment of the endogenous HSP90a encoded by the sequence spanning from aa 236 to aa 336; and HPfΔC2 is the 87 amino acid fragment of the endogenous HSP90a encoded by the sequence spanning from aa236 to aa 322 (see FIG. 1) of the full amino acid sequence of HSP90a (SEQ ID. NO. 2).

Figures 1A, 9:
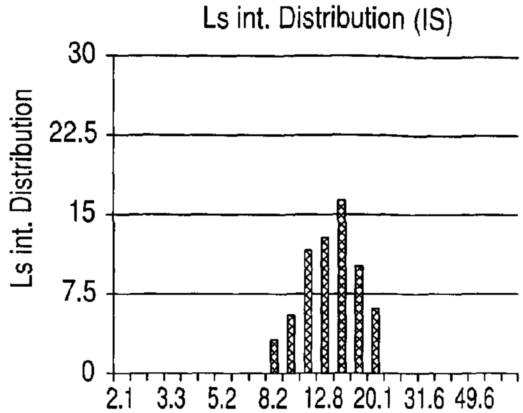
Figures 1B, 9:
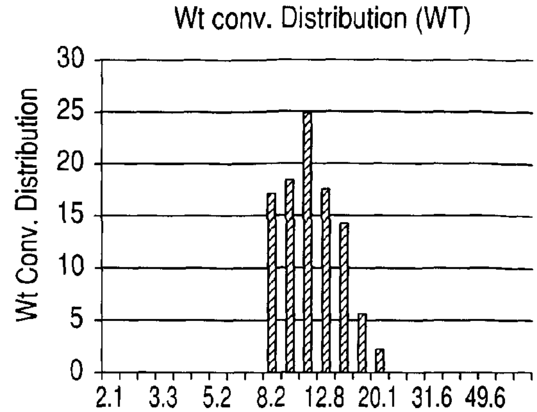
Figures 1C, 9:
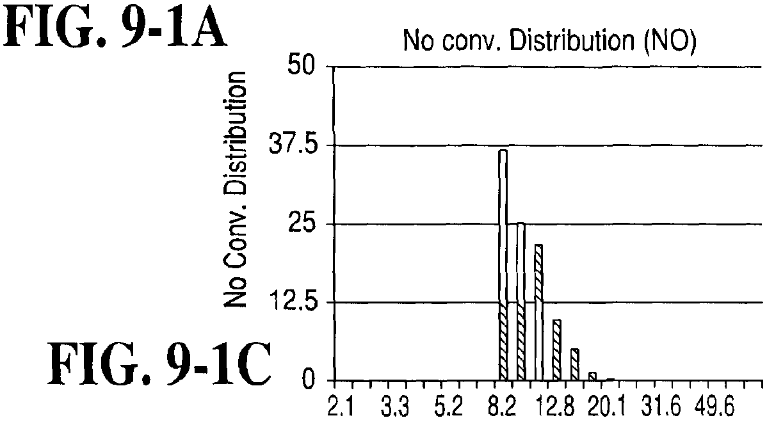

As HPf protein showed a very high propensity of forming aggregates as characterized by ELS and GFC analyses of FIG. 9, its aa sequence and 3D structure were examined for the reasons of HPf aggregation, and the present inventors sought to devise ways to overcome this aggregation problem. The present inventors suspected a hydrophobic stretch of aa sequence in HPf might be the reason for this aggregation. Therefore, two other constructs were designed, HPfΔC1 and HPfΔC2, that eliminated the hydrophobic stretch of HPf, and presented novel polypeptides. The resultant HPfΔC1 and HPfΔC2 showed much better aggregation profile, and hence gave HPfΔC1 or HPfΔC2 separation and purification advantages over HPf. HPfΔC1 construct gave a soluble HPfΔC1 protein form while HPfΔC2 gave an inclusion body form when each over-expression was attempted. To increase the separation yield and facilitate the purification efficiency, the smallest fragment HPfΔC2 was chosen for further studies. The HPfΔC2 polypeptide was surprisingly found to be at least as active as HPf, and in some parameters, to be even more active than HPf.

The biochemical/biological properties of the HPf and HPfΔC2 can be determined based on the following three factors: 1) Over 90% of the amino acid sequence identity with HPf or HPfΔC2, 2) Binding of each fragment to the receptor or other binding proteins of the endogenous HSP90a, and 3) the biological activity of HPf or HPfΔC2.

According to some embodiments, a composition according to the present invention is a phospholipid or liposome composition, and preferably a liposome or nano-liposomal composition. In some embodiments, the HPf (encoded by SEQ ID. NO. 1) is encapsulated in liposomes or nano-liposomes, and applied to the skin. According to some embodiments, the inventive composition is a nano-liposomal composition formulated for topical administration.

As used herein, the term "nano-liposome" refers to a liposome having the form of conventional liposome and a mean particle diameter of 20-1000 nm. According to some embodiments, the mean particle diameter of the nano-liposome is 50-500 nm, more preferably 50-350 nm, and most preferably 100-250 nm.

As used herein, the term "liposome" refers to a spherical phospholipid vesicle of colloidal particles which are associated with themselves, and liposomes composed of amphiphilic molecules, each having a water soluble head (hydrophilic group) and a water insoluble tail (hydrophobic group), and show a structure aligned by spontaneous binding caused by the interaction there between. The liposome is classified, according to the size and lamellarity thereof, into SUV (small unilamellar vesicle), LUV (large unilamellar vesicle) and MLV (multi lamellar vesicle). The liposomes showing various lamellarities as described above have a double membrane structure similar to the cell membrane.

The nano-liposome and liposome of the present invention can be prepared using phospholipid, polyol, a surfactant, fatty acid, salt and/or water.

The phospholipid which is a component used in the preparation of the liposome and nano-liposome, is used as an amphipathic lipid. By way of example, such amphipathic lipids include natural phospholipids (e.g., egg yolk lecithin, soybean lecithin, and sphingomyelin) and synthetic phospholipids (e.g., dipalmitoylphosphatidyl—choline or hydrogenated lecithin), the lecithin being preferred. More preferably, the lecithin is a naturally derived unsaturated or saturated lecithin extracted from soybean or egg yolk.

Polyols which can be used in the preparation of the inventive nano-liposome are not specifically limited, and may include propylene glycol, dipropylene glycol, 1,3-butylene glycol, glycerin, methylpropanediol, isoprene glycol, pentylene glycol, erythritol, xylitol and sorbitol.

The surfactant which can be used in the preparation of the inventive nano-liposome may be any surfactant known in the art, and examples thereof include anionic surfactants (e.g., alkyl acyl glutamate, alkyl phosphate, alkyl lactate, dialkyl phosphate and trialkyl phosphate), cationic surfactants, amphoteric surfactants and nonionic surfactants (e.g., alkoxylated alkylether, alkoxylated alkylester, alkylpolyglycoside, polyglycerylester and sugar ester).

The fatty acids which can be used in the preparation of the inventive nano-liposome are higher fatty acids, and preferably saturated or unsaturated fatty acid having a C12-22 alkyl chain, and examples thereof include lauric acid, myristic acid, palmitic acid, stearic acid, oleic acid and linoleic acid.

Water which is used in the preparation of the inventive nano-liposome is generally deionized distilled water.

According to some embodiments, the inventive nano-liposome is prepared only with phospholipid, salt and water, as described in detail in the Examples below.

According to some embodiments, the HPf-containing nano-liposome is prepared through a process comprising the steps of: (a) dissolving a phospholipid capable of forming liposome (preferably, yellow yolk lecithin or soybean lecithin) in a buffered aqueous solution of salt containing HPf; and (b) passing the aqueous solution containing HPf and phospholipid through a high-pressure homogenizer while gradually increasing the content of the phospholipid and the pressure of the high-pressure homogenizer as the number of the passages increases, thus preparing a HPf-containing nano-liposome.

The aqueous solution containing HPf is preferably a buffer solution having a pH of 6-8, and more preferably about 7, for example, sodium phosphate buffer solution. If the sodium phosphate buffer solution is used, the concentration thereof will preferably be 5-100 mM, more preferably 5-60 mM, even more preferably 10-30 mM, and most preferably about 20 mM.

The mixture of the phospholipid and the HPf-containing aqueous solution is passed through a high-pressure homogenizer several times, in which the amount of the phospholipid and the pressure of the homogenizer are gradually increased as the number of the passages increases. According to a preferred embodiment of the present invention, the pressure of the homogenizer is increased gradually to 0-1000 bar, and preferably 0-800 bar. The pressure can be increased by 50 bar or 100 bar in each cycle, and preferably 100 bar. According to a preferred embodiment of the present invention, the amount of the phospholipid is gradually increased to 5-40 w/v (%) in each cycle, and more preferably 5-30 w/v (%). Through the high-pressure homogenization process including these gradual increases in phospholipid content and pressure, an HPf-containing nano-liposome is prepared and a liquid HPf-containing nano-liposome is preferably prepared.

The present invention is shown herein to be effective for treating atopic dermatitis. While not wishing to be limited to any particular theory or mechanism of action, it is contemplated that this effect may be the result of suppressing the immune function around the affected areas while simultaneously healing the wounds, whereas anti-histamine or steroid containing compositions traditionally used for atopic dermatitis work only by suppressing the immune functions without a wound healing activity.

The composition of the present invention is also shown to provide an improvement of various other skin conditions. For example, the compositions provide an effective treatment for various skin conditions, including wrinkles, dark spots, improving skin elasticity, reducing skin aging, and improving skin moisture.

Furthermore, the composition of the present invention is effective in suppressing the subcutaneous fat cell differentiation hence reducing the subcutaneous fat accumulation. Accordingly, the liposome encapsulated HPf of the present invention is effective for treating obesity, and the accompanying adversities, such as cellulite, varicose veins of lower extremities with ulcer, the edema of lower extremities due to the varicose veins, coloration of the skin, venous eczema, scleroderma, inflammatory thrombus, skin ulcer, chronic pain, disablement of leg functions or any combination of the above symptoms due to the obesity.

The present composition may be provided as a cosmetic or pharmaceutical composition. Accordingly, the active and effective ingredients include compositions that are commonly used for preparing cosmetic products, such as a stabilizer, emulsifier, vitamins, coloring agents, perfume, auxiliaries as well as carrier or combination of any of these besides the HPf and the encapsulating nano-liposome. This product is referred to as Lipo-HSP90a.

The cosmetic compositions of this invention for improving skin conditions may be formulated in a wide variety of forms, for example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray.

The cosmetically acceptable carrier contained in the present cosmetic composition, may be varied depending on the type of the formulation. For example, the formulation of ointment, pastes, creams or gels may comprise animal and vegetable fats, waxes, paraffin, starch, tragacanth, cellulose derivatives, polyethylene glycols, silicones, bentonites, silica, talc, zinc oxide or mixtures of these substances. In the formulation of powder or spray, it may comprise lactose, talc, silica, aluminum hydroxide, calcium silicate, polyamide powder and mixtures of these substances. Spray may additionally comprise the customary propellants, for example, chlorofluorohydrocarbons, propane/butane or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butylglycol, oils, in particular cottonseed oil, groundnut oil, maize germ oil, olive oil, castor oil and sesame seed oil, glycerol fatty esters, polyethylene glycol and fatty acid esters of sorbitan or mixtures of these substances. The formulation of suspension may comprise liquid diluents, for example water, ethanol or propylene glycol, suspending agents, for example ethoxylated isosteary alcohols, polyoxyethylene sorbitol esters and poly oxyethylene sorbitan esters, microcrystalline cellulose, aluminum metahydroxide, bentonite, agar and tragacanth or mixtures of these substances.

The formulation of soap may comprise alkali metal salts of fatty acids, salts of fatty acid hemiesters, fatty acid protein hydrolysates, isothionates, lanolin, fatty alcohol, vegetable oil, glycerol, sugars or mixtures of these substances.

In addition, the cosmetic compositions of this invention may contain auxiliaries as well as carrier. The non-limiting examples of auxiliaries include preservatives, antioxidants, stabilizers, solubilizers, vitamins, colorants, odor improvers or mixtures of these substances.

According to the conventional techniques known to those skilled in the art, the pharmaceutical compositions of this invention can be formulated with pharmaceutical acceptable carrier and/or vehicle as described above, finally providing several forms including a unit dosage form. Most preferably, the pharmaceutical composition is a solution comprising nano-liposomes.

The pharmaceutical compositions comprise a pharmaceutically acceptable carrier. The acceptable carriers include carbohydrates (e.g., lactose, amylose, dextrose, sucrose, sorbitol, mannitol, starch, cellulose), gum acacia, calcium phosphate, alginate, gelatin, calcium silicate, microcrystalline cellulose, polyvinylpyrrolidone, water, salt solutions, alcohols, gum arabic, syrup, vegetable oils (e.g., corn oil, cotton-seed oil, peanut oil, olive oil, coconut oil), polyethylene glycols, methyl cellulose, methylhydroxy benzoate, propylhydroxy benzoate, talc, magnesium stearate and mineral oil, but not limited to. The pharmaceutical compositions of this invention, further may contain wetting agent, sweetening agent, emulsifier, buffer, suspending agent, preservatives, flavors, perfumes, lubricant, stabilizer, or mixtures of these substances. Details of suitable pharmaceutically acceptable carriers and formulations can be found in Remington's Pharmaceutical Sciences (19th ed., 1995), which is incorporated herein by reference.

The pharmaceutical composition of this invention is developed for topical administration onto skin. The correct dosage of the pharmaceutical compositions of this invention will be varied according to the particular formulation, the mode of application, age, body weight and sex of the patient, diet, time of administration, condition of the patient, drug combinations, reaction sensitivities and severity of the disease. It is understood that the ordinary skilled physician will readily be able to determine and prescribe a correct dosage of this pharmaceutical compositions. According to a preferred embodiment of this invention, the suitable dosage unit is to administer once a day with 10 pg HPf/cm2 of the affected area ~1 mg/cm2, 1 ng/cm2~10 μg/cm2, most preferably 10 ng/cm2~1 μg/cm2.

EXAMPLES

The following specific examples are intended for illustrating the invention and should not be construed as limiting the scope of the invention as defined by appended claims.

Example 1. Obtaining the Fragment of HSP90a (HPf)

1-1) Amplification of the HSP90a Fragment (HPf) cDNA

The 115 amino acids polypeptide (SEQ ID. NO. 1) used in the present invention is a fragment of HSP90a (UniProt id: P07900), the sequence spanning from amino acid (aa) no. 236 to aa no. 350 of the endogenous protein. This fragment is referred to as a fragment HPf. In order to produce the HPf in a large scale, the HPf gene was cloned and expressed in *E. coli.*

More specifically, to clone the gene from the human cDNA library, HEK (Human Embryonic kidney) 293 cell line (CRL-1537, ATCC, USA) was incubated in 6 well plates for 3 days. After the removal of the culture media TRizol solution (Invitrogen, USA) 1 ml was added to dissolve the cells, which was then mixed with 200 μl chloroform by strong vortexing for 10 seconds. The mixture was centrifuged at 12,000×g (Centrifuge 5418, Eppendorf, USA) for 15 minutes. After the supernatant was collected and transferred to a new E-tube 0.5 ml isopropyl was added and centrifuged at 12,000×g for 10 minutes to precipitate the total RNA. The total RNA was washed with 70% ethanol once then dissolved in water free of RNAse and DNAse. Such purified RNA was used to construct the cDNA library. The cDNA was synthesized using Omniscript Reverse Transcription kit (Qiagen, U.S.A.) following the instruction provided in the manufacturer's manual. First, the total RNA 1 μg, 1×RT buffer, dNTP mix, oligo-dT primers, RNAse inhibitors and Omniscript Reverse Transcriptase were mixed, then DNase, RNase free water was added to adjust the volume to 20 μl, which then was incubated at 37° C. for 60 minutes to obtain the cDNA library. Using the cDNA library as the template, genes to be cloned were prepared by amplifying by PCR. The PCR mixture contains 1×PCR buffer, 6.4 μl 2.5 mM dNTP mix, template (cDNA prepared above), 0.8 μl 100 pmole primer stock, (SEQ ID. NO. 4 and 5) and 0.4 μl proofreading Taq polymerase (TAKARA, Japan) in total volume of 100 μl. The PCR was performed at 95° C., 30 seconds for denaturing, 60°, 30 seconds for annealing, 72°, 45 seconds for amplification, repeating 35 cycles to amplify the HPf gene. Subsequently the product was analyzed using agarose gel electrophorosis to verify the amplification of HPf gene. The HPf nucleotide sequence is encoded by the SEQ ID. NO. 3, and the amino acid by sequence at SEQ ID. NO. 1.

1-2) Preparation of the Recombinant HPf Protein

Figures 1A, 2:
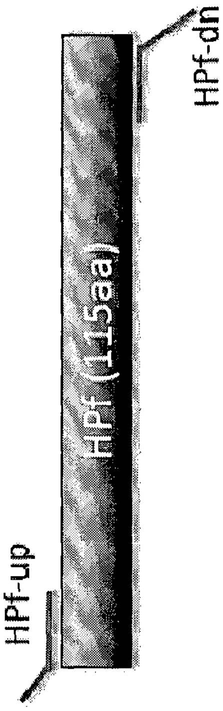

The HPf cDNA obtained from the Example procedure 1-1 above (cDNA of SEQ ID. NO. 3) prepared through amplification with two primers (SEQ ID. NO. 4 and SEQ ID. NO. 5) was cloned into pNKmut plasmid (Korean Patent 10-0985746) using restriction enzymes NdeI and KpnI (FIG. 2-1A).

To increase the stability and production of HPf, fusion proteins of HPf were expressed using TRX (Thioredoxin A, pET-32a, Novagen, USA), MBP (maltose binding protein, GeneScript, USA), or HGH (human growth hormone, DNA-sequence ID: NM_000515.3) as a fusion partner fused in front of HPf.

To facilitate purification of HPf from the fusion protein with TRX, a cleavage site for either hydroxylamine (Asn/Gly; N/G) or TEV (Tabacco Etch Virus) was inserted in between TRX and HPf in the fusion construct.

To prepare a fusion protein TRX(NGc)-HPf that is a chimeric construct of HPf coupled to a fusion partner TRX with an internal hydroxylamine cleavage site, TRX DNA portion TRX(NGc) (SEQ ID. NO. 18) was obtained by performing PCR using primers (SEQ ID. NO. 8 and SEQ ID. NO. 9) and pET-32a (0.1 μg) as the template following Example 1-1 above. Similarly HPf DNA portion was obtained by performing PCR using primers (SEQ ID. NO. 5 and SEQ ID. NO. 11) following the procedure as in Example 1-1. To combine TRX(NGc) and HPf DNA's, primers (SEQ ID. NO. 5 and SEQ ID. NO. 8) were adopted to perform PCR using the 1:1 mixture of TRX(NGc) and HPf as the template. The subsequent PCR product was subcloned into Expression Vector pNKmut (Korean Patent 10-0985746) using DNA restriction enzymes NdeI and KpnI (FIG. 2-1B).

Likewise, to prepare a fusion protein TRX(TEVc)-HPf that is a chimeric construct of HPf coupled to a fusion partner TRX with an internal TEV cleavage site, TRX DNA portion TRX(TEVc) (SEQ ID. NO. 19) was obtained by performing PCR using primers (SEQ ID. NO. 8 and SEQ ID. NO. 10) and pET-32a (0.1 μg) as the template following Example 1-1 above. Similarly HPf DNA portion was obtained by performing PCR using primers (SEQ ID. NO. 5 and SEQ ID. NO. 12) following the same procedure as in Example 1-1. BamHI restriction site was also created between TRX and HPf for later ease of cloning manipulations. To combine TRX(TEVc) and HPf DNA's, primers (SEQ ID. NO. 5 and SEQ ID. NO. 8) were used to perform PCR using the 1:1 mixture of TRX(TEVc) and HPf as the template. The subsequent PCR product was subcloned into Expression Vector pNKmut (Korean Patent 10-0985746) using DNA restriction enzymes NdeI and KpnI (FIG. 2-1C).

Figures 1B, 2:
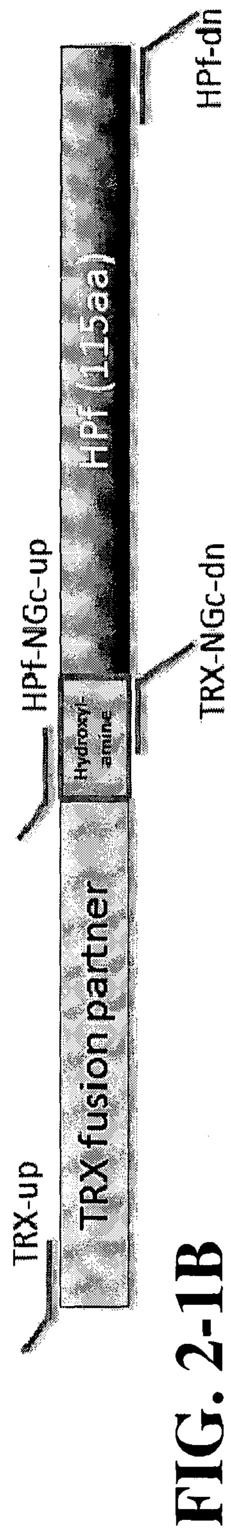
Figures 1C, 2:
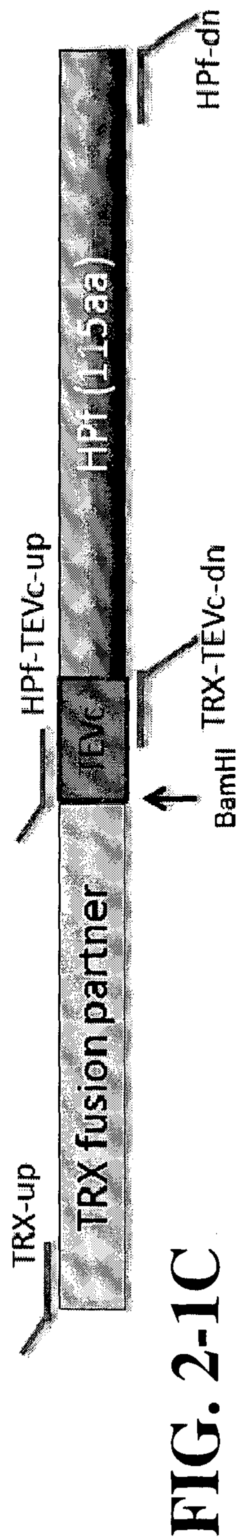
Figures 2, 2A:
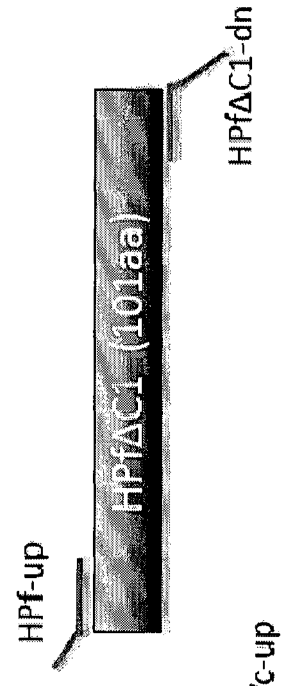
Figures 2, 2B:
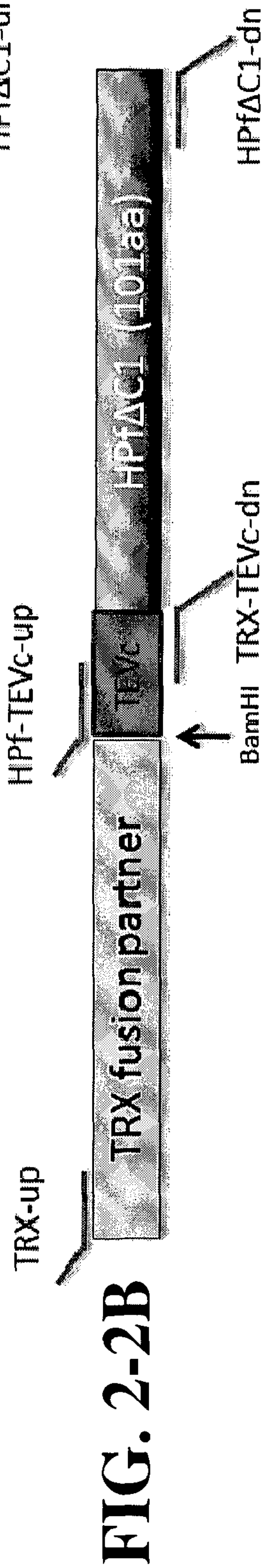
Figures 2, 2C:
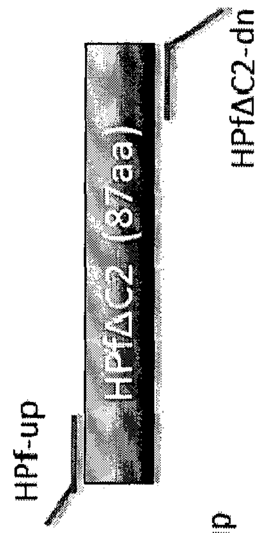
Figures 2, 2D:
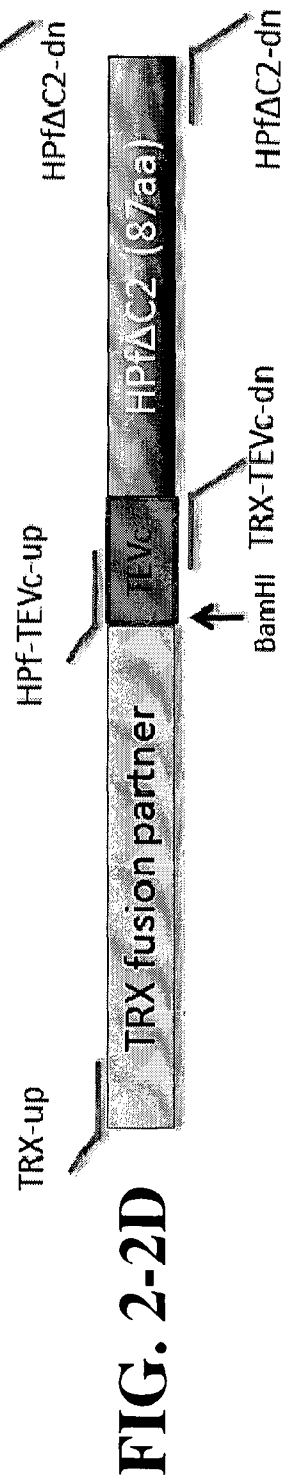
Figures 2, 3, 3A:
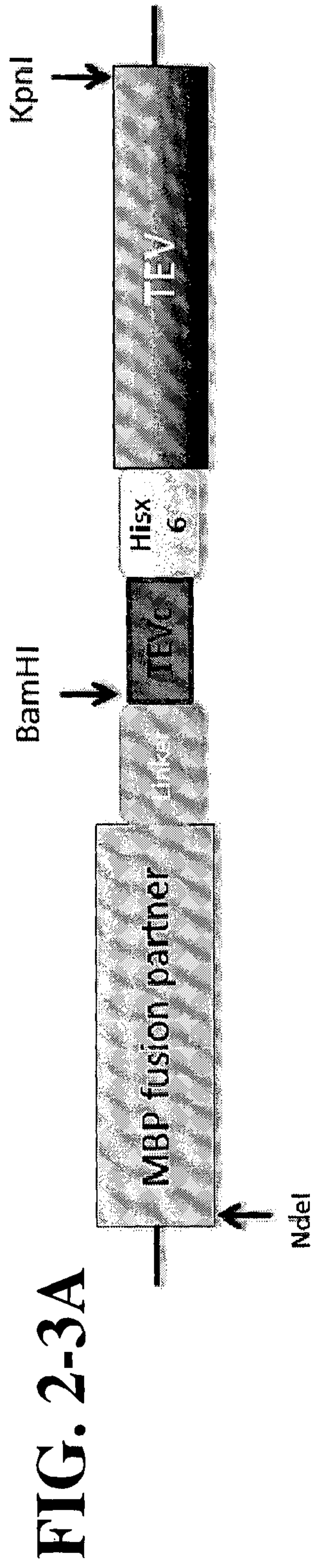

TRX(NGc)-HPf or TRX(TEVc)-HPf fusion protein thus produced in a transformed *E. coli* cells showed a much greater level of expression compared to HPf produced without a TRX fusion partner (FIGS. 3-1A and 3-1B).

Figure 1:
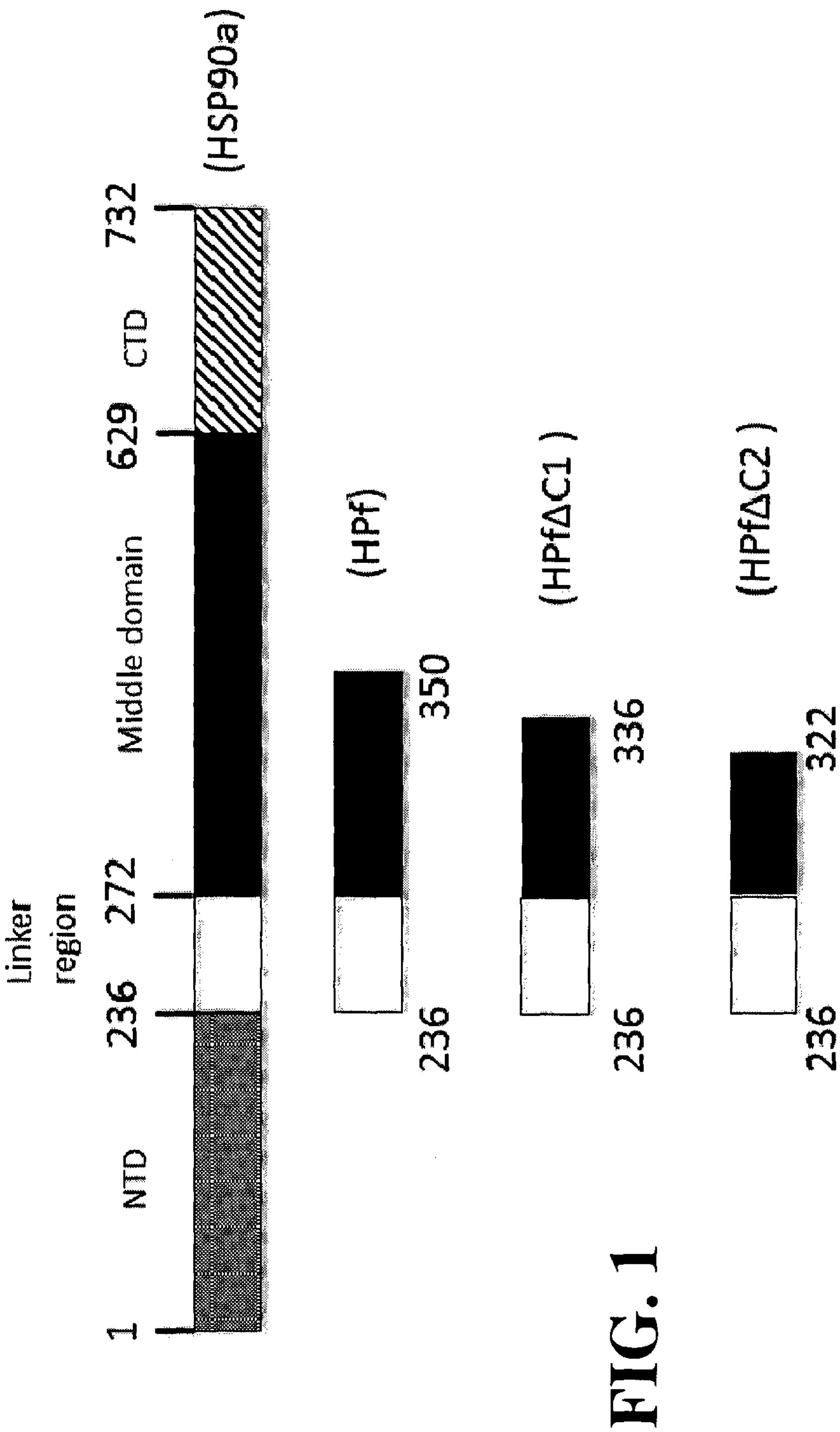
FIG. 1 shows the sequence of three (3) fragments of the endogenous HSP90a polypeptide: a 115 amino acid fragment, (Glu236aa to Asp350aa), named HPf; a 101 amino acid fragment (Glu236-Glu336), named HPfΔC1; and an 87 amino acid fragment (Glu236-Asp 322), named HPfΔC2. HPf and HPfΔC2 are used as active ingredients of the present preparations/formulations.

HPf protein's c-terminal deletion mutant—HPfΔC1 and HPfΔC2 is constructed. HPfΔC1 is a fragment of HSP90a (part of HSP90a) consisting of 101 amino acids in total comprising from Glu236 to Glu336 of HSP90a protein (UniProt ID: P0790), which was eliminated 14 amino acids from HPf in the carboxyl-terminal (SEQ ID. NO. 20). Also, HPfΔC2 is a fragment of HSP90a composed of 87 amino acids in total comprising from Glu236 to Asp322 (of HSP90a), which has 28 carboxyl-terminal amino acids less of HPf, resulting in the smallest protein of the present invention (SEQ ID. NO. 21) (FIG. 1).

In order to express the HPfΔC1 recombinant protein, the HPf cDNA, acquired from the Example procedure 1-1, was used as the template and Seq. no. 4 and 6 as primers, via a PCR method described in Example 1-1. The HPfΔC1 gene with the sequence identical to seq. no. 22 was thus obtained and was further cloned into protein expression vector pNK-mut (Korean Patent 10-0985746) using DNA restriction enzymes NdeI and KpnI. (FIG. 2-2A).

To clone TRX(TEVc)-HpfΔC1 fusion protein composed of Thioredoxin A coupled with TEV protease recognition site, HPfΔC1 gene was obtained by running a PCR using HPf cDNA as a template and seq. no 6 and 12 as primers by following the same PCR method described in Example 1-1 above. TRX(TEVc)-HPf fusion protein-expression plasmid and HPfΔC1 gene produced by the PCR were digested by BamHI and KpnI DNA restriction enzymes, then HPfΔC1 was cloned into HPf gene-eliminated plasmid by substitution, yielding HGH(TEVc)-HPfΔC1 fusion protein-expression plasmid. (FIG. 2-2B).

In order to express HPfΔC2 recombinant protein, HPf cDNA acquired from Example 1-1 was used as the template, and primers for seq. no. 4 and 7 were used to acquire HPfΔC2 with seq. no. 23, by following the PCR methods described in Example 1-1 above. The resultant PCR product thus obtained was cloned into the protein expression vector pNKmut (Korean Patent 10-0985746) using DNA restriction enzymes NdeI and KpnI. (FIG. 2-2C).

To clone TRX(TEVc)-HPfΔC2 fusion protein composed of Thioredoxin A coupled with TEV protease recognition site, HPfΔC2 gene was obtained by running a PCR using HPf cDNA obtained from Example 1-1 as the template and seq. no 7 and 12 as primers by following the same PCR methods described in Example 1-1 above. TRX(TEVc)-HPf fusion protein-expression plasmid and HPfΔC2 gene produced by the PCR were digested by BamHI and KpnI DNA restriction enzymes, then HPfΔC2 was cloned into HPf gene-eliminated plasmid by substitution, yielding HGH (TEVc)-HPfΔC2 fusion protein-expression plasmid. (FIG. 2-2D).

TRX(TEVc)-HPfΔC1 and TRX(TEVc)-HPfΔC2 were transformed into *E. coli* strain for a scaled-up fermentation, then their respective protein expression was determined by using SDS-PAGE. Unexpectedly, those two smaller-version proteins, HPfΔC1 and HPfΔC2, were expressed as soluble protein forms in the cytoplasm while all HPf-containing fusion proteins are expressed as inclusion body forms (FIG. 3-2C).

The primers used for all PCR procedures are listed in the Table 1 below.

TABLE 1

Sequences of the primers for PCR

| Primers | Sequence | Seq. No. |
|---|---|---|
| HPf-up | 5'-GAGACATATGGAAGAAAAGGAAGACAAAGAAGAAGAA-3' | 4 |
| HPf-dn | 5'-TATAGGTACCTTAATCAAAAGGAGCACGTCGTGGGACA-3' | 5 |
| HPfΔC1-dn | 5'-GGGGTACCTCATTCCAACTGTCCTTCAACTGAA-3' | 6 |
| HPfΔC2-dn | 5'-GGGGTACCTCAATCTTCCCAGTCATTGGTCAAG-3' | 7 |
| TRX-up | 5'-TTAATTCATATGAGCGATAAAATTATTCACC-3' | 8 |
| TRX-NGc-dn | 5'-ACCGTTTTTGAACAGCAGC-3' | 9 |
| TRX-TEVc-dn | 5'-CTGGAAGTACAGGTTTTCGGATCCATTACCGTTTTTGAACAGCAGCAG-3' | 10 |
| HPf-NGc-up | 5'-GCTGCTGTTCAAAAACGGTGAAGAAAAGGAAGACAAAGAAGAAGAA-3' | 11 |
| HPf-TEVc-up | 5'-GGATCCGAAAACCTGTACTTCCAGGGTGAAGAAAAGGAAGACAAAGAAGAAGAA-3' | 12 |
| HGH-Nde-up | 5'-GAGACATATGTTCCCGACCATCCCGCTGTCT-'9 | 13 |
| HGH-7His-dn | 5'-TTTCGGATCCAGAACCATGATGATGGTGATGATGATGACCGAAGCCACAGCTGCCCTC-3' | 14 |
| HSP90 (full)-up | 5'-GAGACATATGCCTGAGGAAACCCAGACCCAGACCC-3' | 15 |

TABLE 1-continued

| Sequences of the primers for PCR | | |
|---|---|---|
| Primers | Sequence | Seq. No. |
| HS P90(full)-dn | 5'-TATAGGTACCTTAGTCTACTTCTTCCATGCGTGAT-3' | 16 |
| HSP90-5p(mid) | 5'-ACTGGCGGAAGATAAAGAGAA-3' | 17 |

To express HPf and HPfΔC2 as fusion proteins coupled to a MBP (maltose binding protein) fusion partner, MBP-TEV fusion construct was synthesized as referenced in Paul, et al (2007) (GeneScript. USA). To facilitate the cloning of MBP with other genes to be expressed, MBP-TEV was modified by introducing DNA restriction enzyme sites NdeI, KpnI, and BamHI at the beginning, at the end, and in between MBP and TEV genes, respectively. (FIG. 2-3A).

Figures 2, 3, 3B:
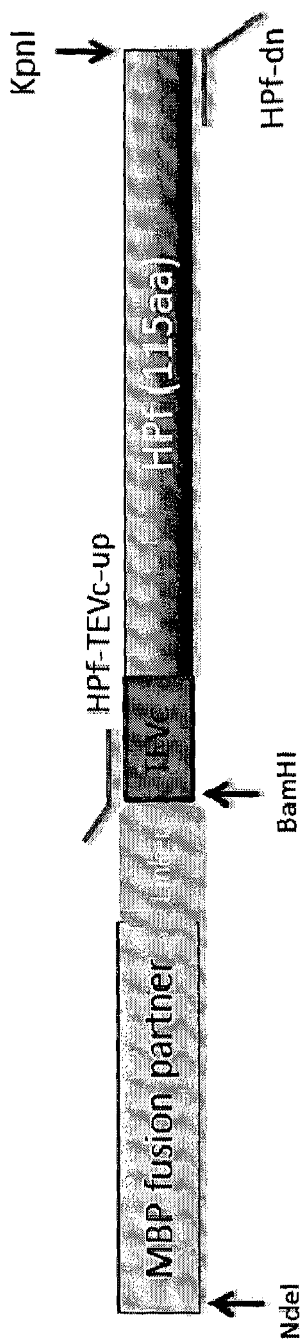

The modified MBP-TEV gene was cloned into the protein-expression vector pNKmut (Korean Patent 10-0985746) plasmid by using DNA restriction enzymes NdeI and KpnI.

pNKmut plasmid containing MBP-TEV fusion construct was recovered and digested by DNA restriction enzymes BamHI and KpnI to remove the internal TEV gene. On the other hand, using SEQ ID. NO. 5 and 12 as primers, a HPf gene was obtained by following the PCR methods described above in Example 1-1. HPf gene thus obtained was digested by BamHI and KpnI, then inserted into the BamHI-KpnI digested pNKmut plasmid containing MBP to obtain MBP (TEVc)-HPf fusion protein-expression plasmid having the sequence identical to SEQ ID. NO. 24 (FIG. 2-3B).

By using TEV recognition site, MBP and its coupled HPf plasmid were transformed into the *E. coli* fermentation host, RZ4500 (Biotechnology Institute, Korea University, S. Korea), BL21(DE3) pLyS (Novagen, USA) and RosettaBlue (DE3) (Novagen, USA) cell lines. MBP(TEVc)-HPf fusion protein expression of the respective transformant was confirmed using SDS-PAGE. The result showed that BL21 (DE3)pLyS transformant showed the highest level of MBP (TEVc)-HPf fusion protein expression in *E. coli*. (FIG. 3-3).

To express HPf fusion construct coupled to HGH (human growth hormone) gene, HGH gene was obtained through running a PCR using HGH gene as the template (DNA-sequence ID: NM_000515.3) and SEQ ID. NO. 13 and 14 as primers by following the same PCR method as described above in Example 1-1.

Figures 2, 3, 4:
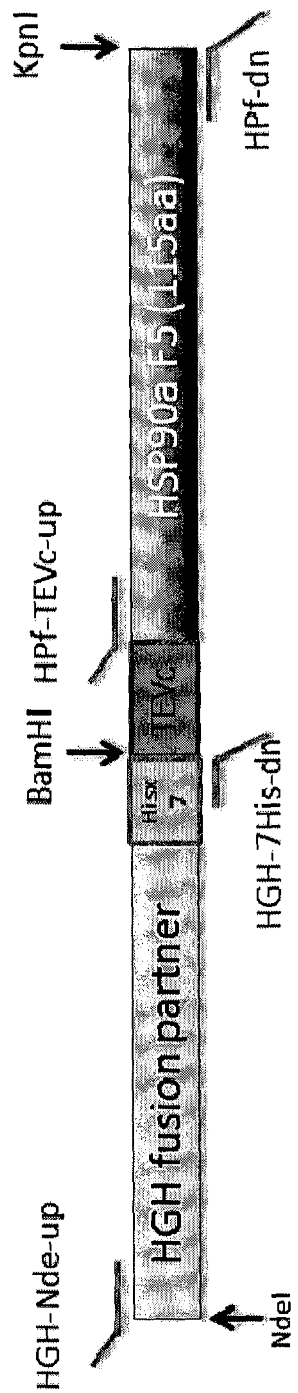
Figures 1B, 3:
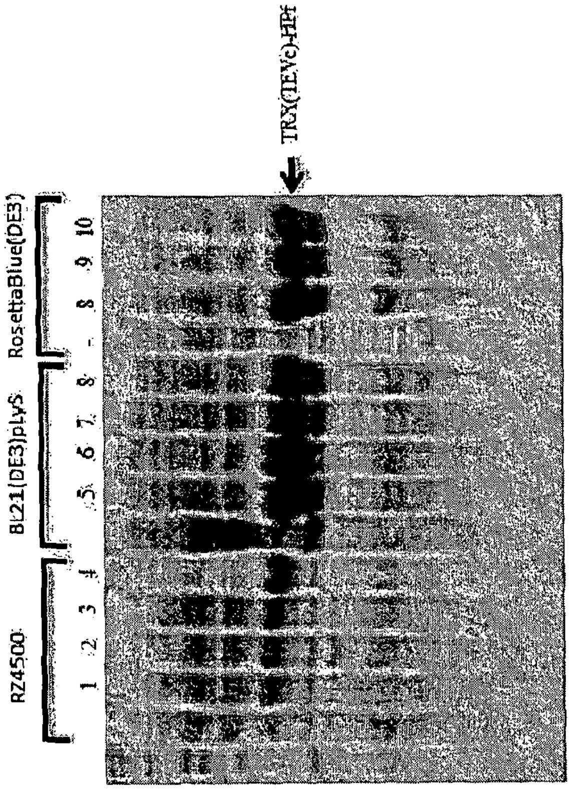
Figures 1A, 3:
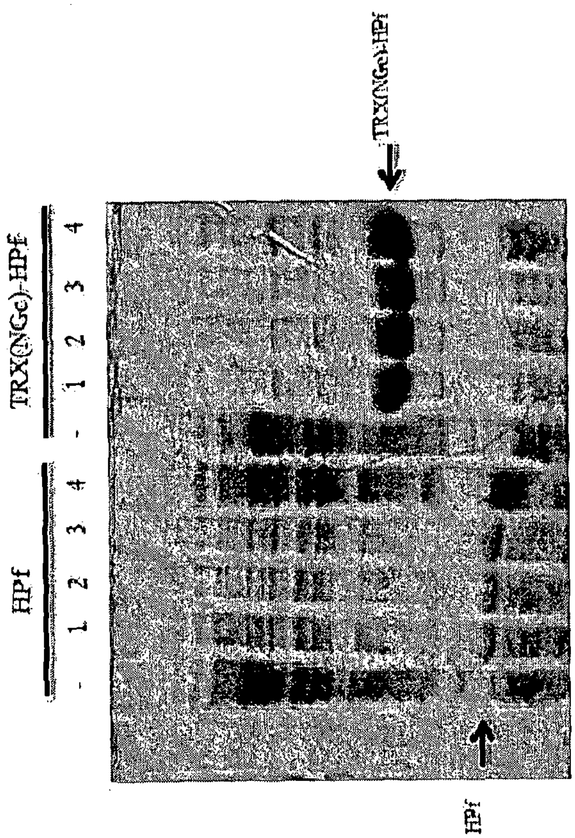
Figures 2A, 3:
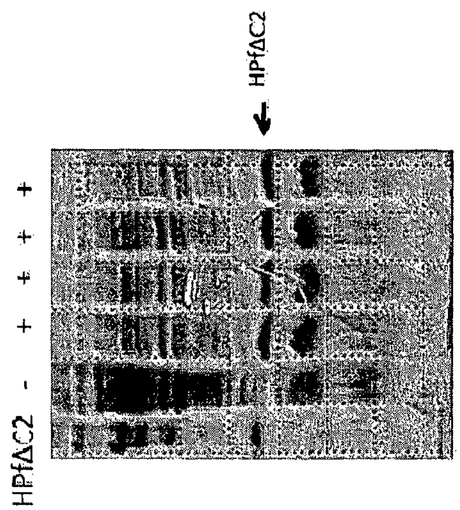
Figures 2B, 3:
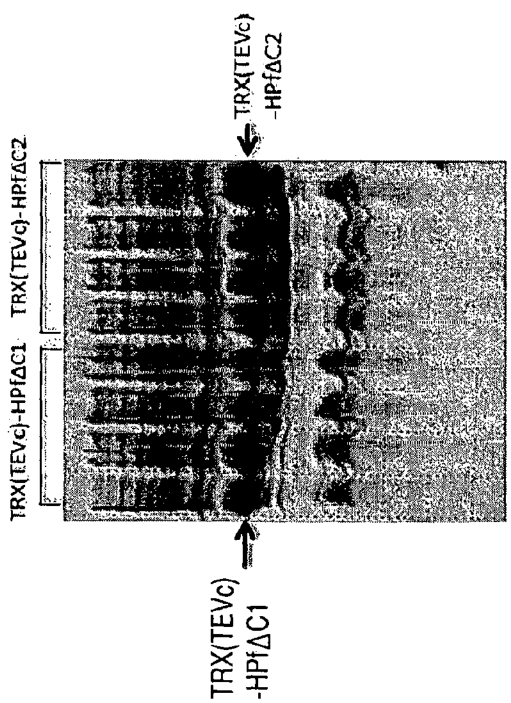
Figures 2C, 3:
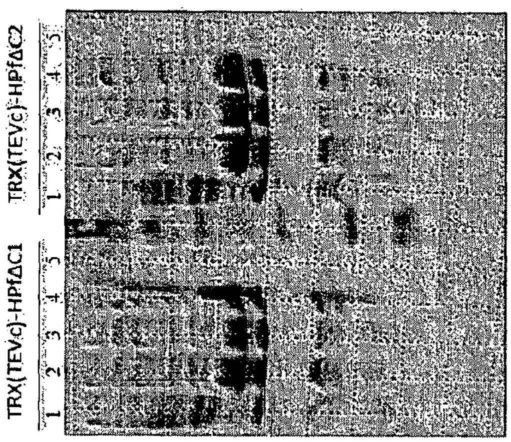
Figure 3:
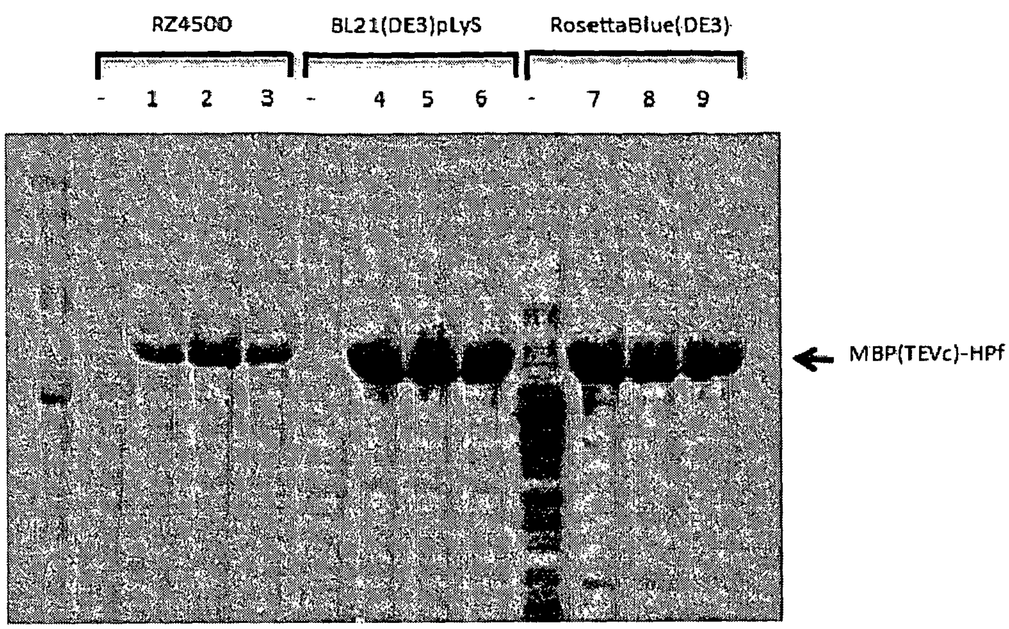
Figures 3, 4, 4A:
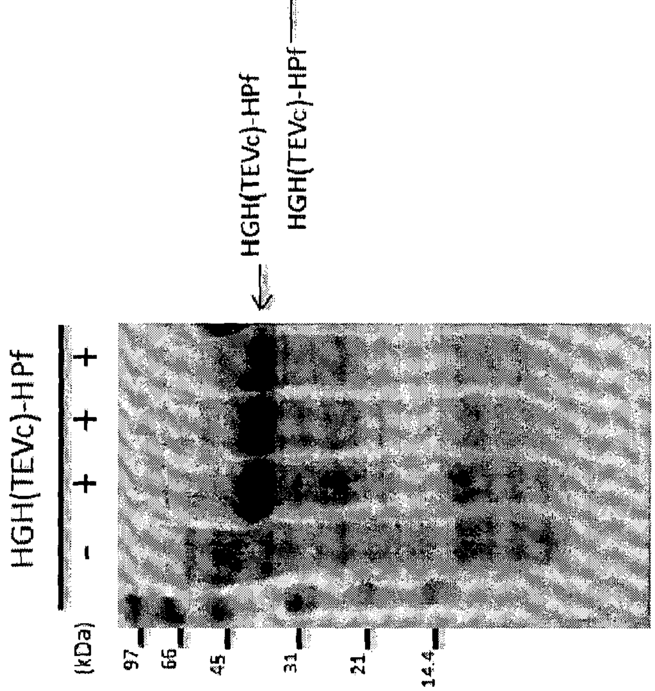

MBP(TEVc)-HPf fusion protein-expression plasmid and HGH gene obtained through the PCR were digested by DNA restriction enzymes NdeI and BamHI, then HGH was cloned into the MBP-eliminated plasmid by substitution, yielding HGH(TEVc)-HPf fusion protein-expression plasmid with the sequence identical to SEQ ID. NO. 25 (FIG. 2-4). The cloned HGH(TEVc)-HPf fusion protein-expression plasmid was transformed into RZ4500 *E. coli* cell line (Biotechnology Institute, Korea University, S. Korea) for a scaled-up fermentation. It was observed that a large quantity of the fusion protein was expressed (FIG. 3-4A). It was also confirmed that HGH(TEVc)-HPf fusion protein was expressed as an inclusion body form within *E. coli* (FIG. 3-4B).

Figures 3, 4, 4B:
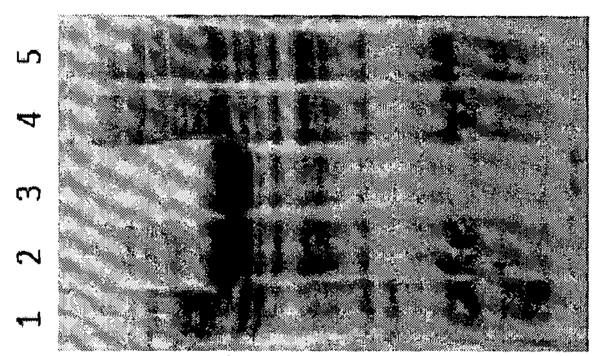
Figures 3, 4, 5:
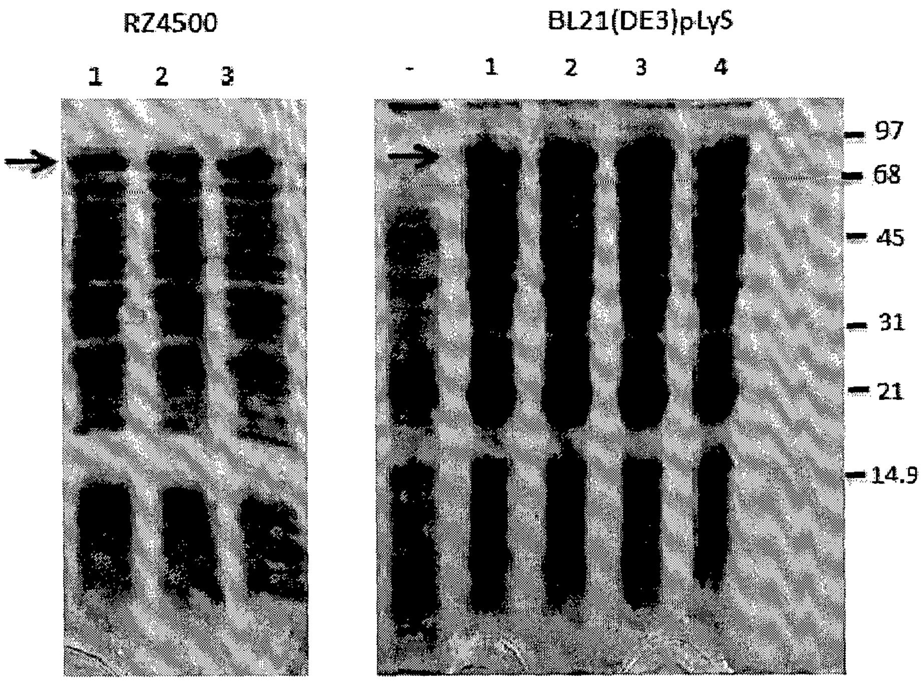
Figure 4B:
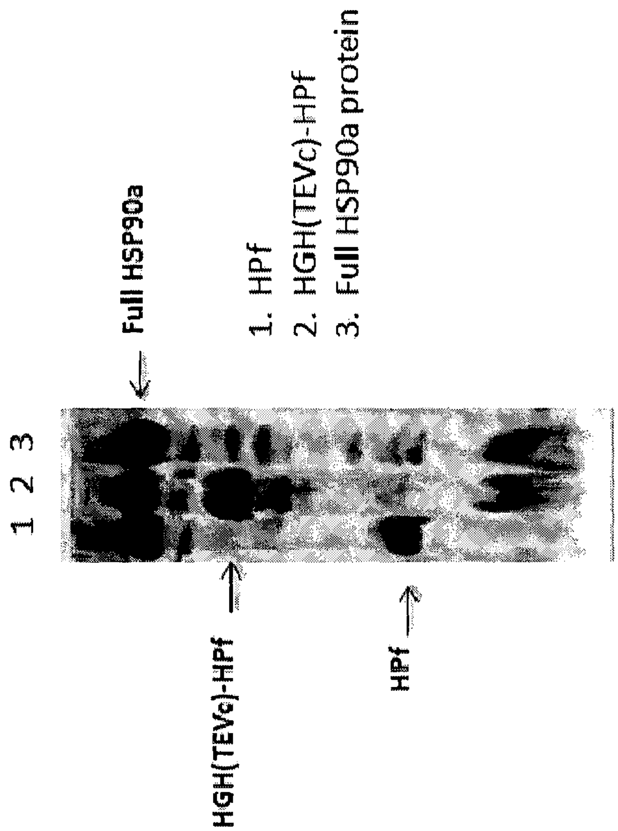
Figure 4A:
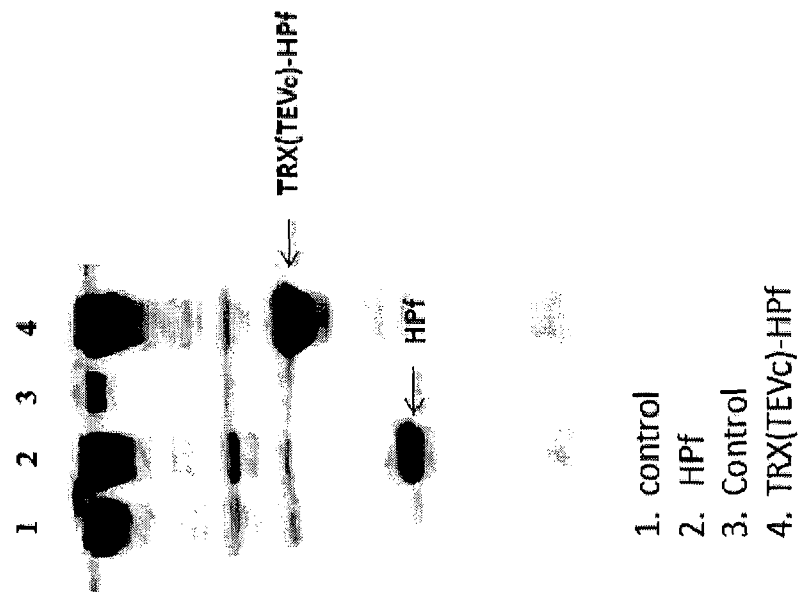
FIG. 4A is the gel results of HPf peptide production with TRX(TEVc)-HPf fusion protein (1. Control, 2. HPf, 3. Control, 4. TRX(TEVc)-HPf). 4B is the gel results of HPf peptide production with HGH(TEVc)-HPf fusion construct. (1. HPf, 2. HGH(TEVc)-HPf, 3. Full HSP90a protein.
Figure 5A:
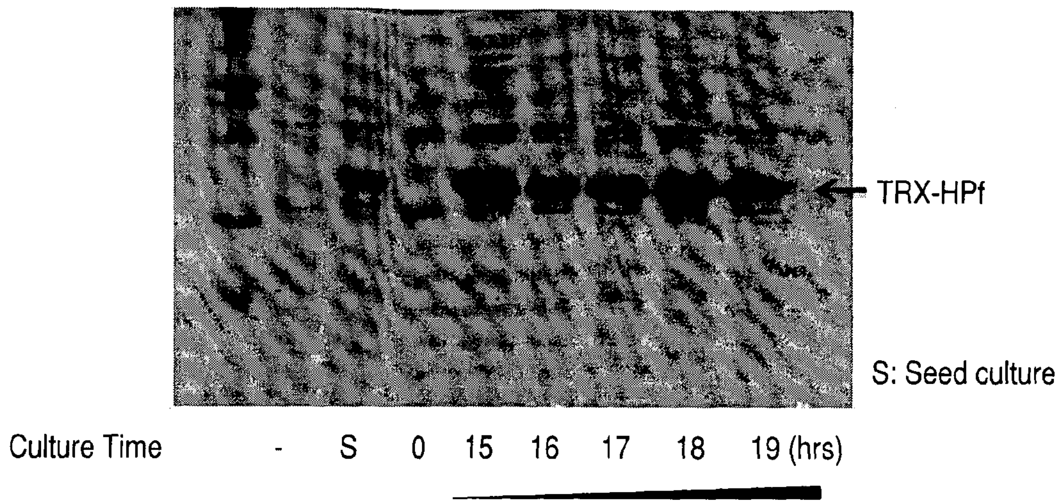
FIG. 5A shows the change of TRX(TEVc)-HPf fusion protein production with increasing culture time in a large scale fermentation (50 liter) for preparing the protein: 5B shows change in dissolved oxygen. 5C shows change in pH (5C), and 5D shows change in optical density.
Figure 5B:
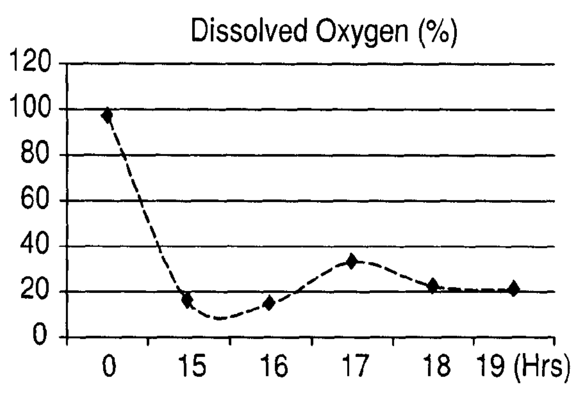
Figure 5C:
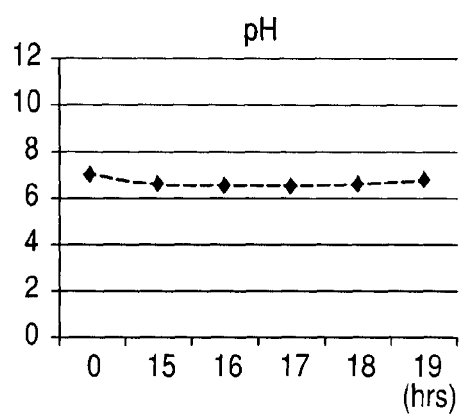
Figure 5D:
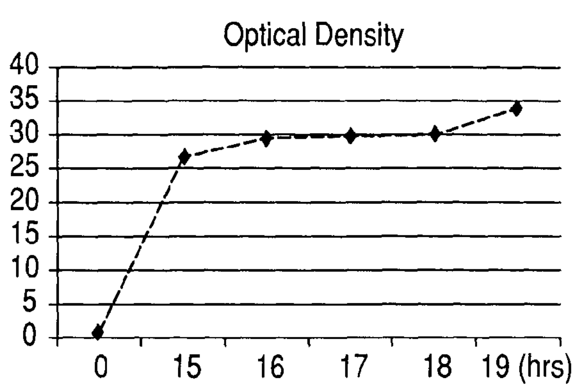

Explanation/Description for Each Line of FIG. 3-4B

1: RZ4500 strain (negative control group), 2: HGH (TEVc)-HPf-overexpressing *E. coli* strain, 3: Homogenized HGH(TEVc)-HPf-overexpressing *E. coli* by sonication, 4. Supernatant from centrifugation of sonication-homogenized *E. coli,* 5: Supernatant collected by centrifugation of the inclusion body re-suspended by washing solution.

Expression of the full HSP90a protein (732 amino acids) was attempted in *E. coli*. Partial carboxy-terminal fragment of full HSP90a gene was obtained by running a PCR using EST (Expressed Sequence Tag, clone id: IRCMP5012A0834D) clone containing full HSP90a gene (full coding region, DNA-sequence ID: NM_001017963) as a template and SEQ ID. NO. 16 and 17 as primers by following the same methods as described above in Example 1-1 (FIG. 2-5A). The partial carboxy-terminal fragment of full HSP90a was subcloned into the plasmid pNKmut (Korean Patent 10-0985746) protein-expression vector by using DNA restriction enzymes NdeI and KpnI. To complete subcloning of the full HSP90a gene, another PCR was run again using the EST clone as the template and SEQ ID. NO. 15 and 16 as primers by following the same methods described above in Example 1-1 (FIG. 2-5A). The PCR products thus acquired was introduced into the NdeI DNA restriction enzyme-digested site of the plasmid containing c-terminal part of HSP90a, resulting in construction of the full HSP90a protein expression plasmid encoding the sequence of HSP90a identical with SEQ ID. NO. 26 (FIG. 2-5B).

Their sequences were analyzed using DNA sequencing confirming the 100% identity to the original sequences of TRX, MBP, hGH, and HPf. The recombinant cDNA constructs were expressed in the RZ4500 cell line (Biotechnology Institute, Korea University, S. Korea), BL21(DE3)pLyS (Novagen, USA), and RosettaBlue (DE3)(Novagen, USA) to obtain the transformants which were then cultured in 5 ml LB (Luria-Bertani) media at 37° C. for 16 hrs.

The protein amount of expressed HPf, TRX(NGc)-HPf, TRX(TEVc)-HPf, MBP(TEVc)-HPf, and hGH(TEVc)-HPf were analyzed by SDS-PAGE, of which results reconfirmed the excellent expression of TRX(TEVc)-HPf gene in BL21 (DE3)pLyS. Therefore, this transformant is demonstrated to produce the recombinant TRX(TEVc)-HPf fusion protein in a large scale (FIGS. 3-1, 3-2, 3-3, and 3-4).

Example 2. Confirmation of the Expression of Recombinant HPf Protein by Immunoblot In order to further confirm whether the expressed recombinant protein described in the Example 1 is HPf, and originated from HSP90a, an immunoblot was performed (FIG. 4).

The transformants expressing the recombinant HPf, TRX (TEVc)-HPf, HGH (TEVc)-HPf, and full HSP90a genes were cultured in 5 ml LB media containing ampicillin by shaking at 37° C. for 16 hours. The culture was centrifuged and the sample was analyzed with SDS-PAGE. The resulting electrophoresis gel was analyzed, first, by transferring proteins on the gel to PVDF filter (Millipore, USA) at 12V for 150 minutes by electrophoresis. Once the transfer is completed, the filter was then immersed in the blocking buffer (10% fat free milk and 0.02% Tween 20 and Tris saline buffer) for 1 hour to inhibit any nonspecific binding. Then the PVDF filter was immersed in the solution containing the HPf specific antibody (Rabbit anti-HSP90 antibody, Calbio-Chem, USA) at room temperature for 90 minutes. The nonspecific binding was eliminated by washing the filter for 10 min for three times in washing buffer (0.02% Tween 20 and Tris saline buffer). Subsequently the secondary antibody, goat anti-immunoglobulin antibody (HRP-linked, KOMA, Korea), was added to the reaction solution and incubated for 1 hour before the filter was washed with the washing buffer three times. By final staining with Chemiluminescence, LAS-4000 (Fuji, Japan) immunoblot results reconfirmed that the expressed protein was HPf. As seen in FIG. 4A, the recombinant HPf alone and recombinant TRX (TEVc)-HPf proteins were recognized by the antibody confirming their identity. The HGH(TEVc)-HPf and Full HSP90a recombinant protein was also recognized by the specific antibody, anti-HSP90a (FIG. 4B).

Example 3. Large Scale Preparation of HPf

The host cell line RX4500 transformed with the vector construct containing the HPf gene TRX(TEVc)-HPf as described in the Example 1 above, was used to determine the optimum conditions for the maximum expression of the recombinant protein. Specifically, the above RZ4500 transformant was cultured in an 1 liter flask, initially in 7 liter fermentator (FMT-07/C-B, Fermentec, Korea), which was gradually increased to final 50 L fermentator (FMT-50, Fermentec, Korea). The culture mixture of the 50 liter fermentator contains compositions described in the Table 2 below.

TABLE 2

Fermentation mixture for preparing the recombinant TRX(TEVc)-HPf protein

| Compounds | % (W/V) |
|---|---|
| $NaHPO_4$ | 0.7 |
| $KH_2PO_4$ | 0.3 |
| $NH_4Cl$ | 0.1 |
| NaCl | 0.05 |
| $NaNO_3$ | 0.1 |
| Yeast extract | 4 |
| Glycerol | 2 |
| Water | to 100 |
| pH | 7.2 |

The seed culture prepared with 1 ml RZ4500 transformed with TRX(TEVc)-HPf (glycerol stock) was added to 500 ml LB media (pH 7.4) in a 2 liter flask by shaking for 6 hours 37° C. until the OD600 reached 0.5~0.6. For 50 liter fermentation, a subculture was prepared by mixing the seed culture and culture media in a ratio of 1:100.

Figures 2, 3, 4, 5, 5A:
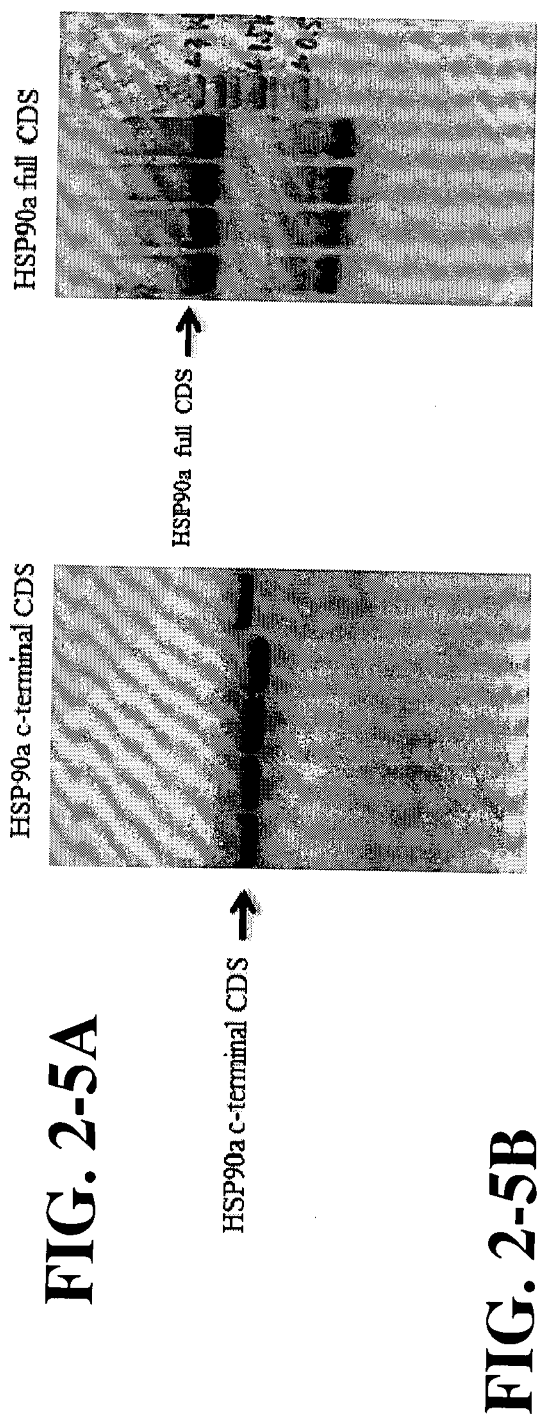
Figures 2, 3, 4, 5, 5B:
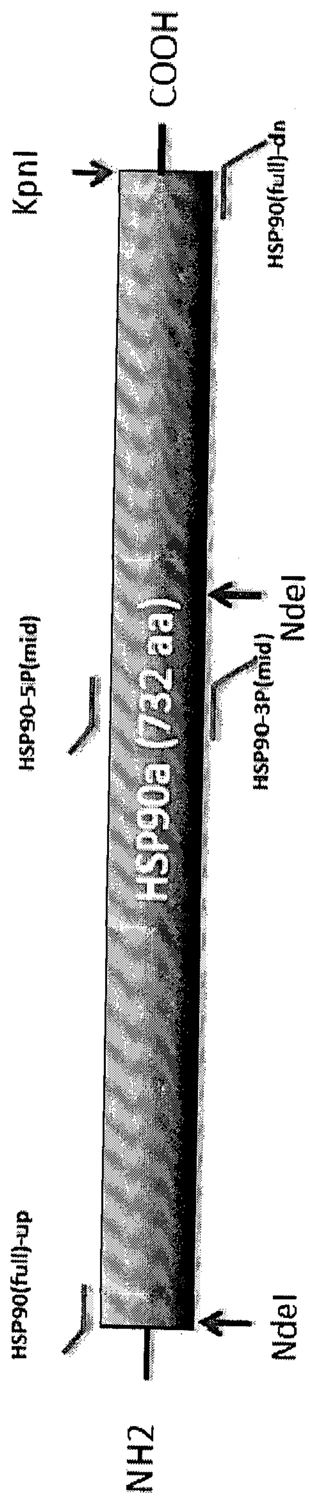

The concentration of dissolved oxygen in the 50 liter culture was decreased gradually as the culture time increased. After 15 hours, the dissolved oxygen concentration remained in the culture was 10% of the concentration measured immediately after adding seed culture (FIG. 5). At that time 100-200 ml autoclaved 100% glycerol was added to the culture in order to supplement the carbon source for the host cell.

During the 15 hours of fermentation, a portion of culture was sampled every hour to analyze the pH, dissolved oxygen, and the O.D. values to determine the growth curve of the host cell (FIG. 5). When the O.D. reached 35-40, the fermentation was terminated. Also a portion of the culture was analyzed by SDS-PAGE and staining with Coomassie Brilliant Blue.

Subsequently, the expression level was quantitatively determined by measuring the protein concentration of the culture vs. the BSA (Bovine Serum Albumin, Sigma, USA) with predetermined concentrations using densitometer (Total Lab Quant, Totallab, USA). The concentration of the recombinant protein was 1 g/L.

Example 4. Purification and Optimization of the HPf Protein

The recombinant cells harvested from the large quantity fermentation was homogenized using homogenizer and washed in 0.5% Triton X-100 using ultracentrifuger (Hanil, Korea). The inclusion body was harvested by collecting the precipitate after removing the supernatant. Then it was dissolved in 25 mM NaOH, renatured with 1% acetic acid, and centrifuged. Only the supernatant was collected to remove impurities. Throughout the purification steps a portion of solutions was removed for analyzing by SDS-PAGE and Coomassie Brilliant Blue.

Figure 6:
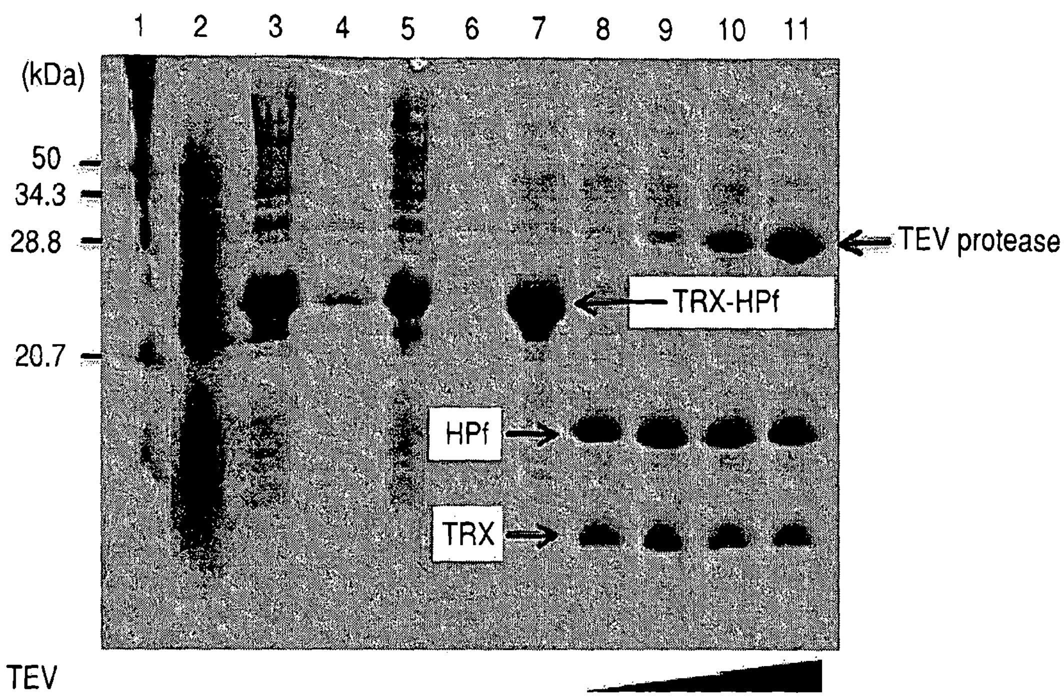
FIG. 6 demonstrates results of the isolation of HPf from the recombinant TRX(TEVc)-HPf fusion protein, separation as an inclusion body, and its TEV-cleavage efficiency depending on the amount of TEV added. 1. Protein marker, 2. Competent cell (negative control), 3. Total cell lysate, 4. Supernatant fraction after homogenization, 5. Pellet after sonication (Inclusion body), 6. Washing solution of the pellet, 7. Solubilized inclusion body. 8-11. Solubilized inclusion body+TEV protease.

As seen in FIG. 6, HPf was expressed as TRX(TEVc)-HPf in the inclusion body rather than in the cytosol (lanes 4 and 5), of the host cell. Its protein structure remained intact during the denaturation with NaOH and renaturation with acetic acid (lane 7). Subsequently, TEV protease was added (TRX(TEVc)-HPf:protease=10:1) and incubated at 4° C. for 24 hours to isolate the HPf from the TRX(TEVc)-HPf chimeric protein. The cleavage of the chimera by TEV protease was confirmed by SDS-PAGE as shown in lanes 8-11. The HPf protein was isolated by gel filtration chromatography (GFC).

Figure 7A:
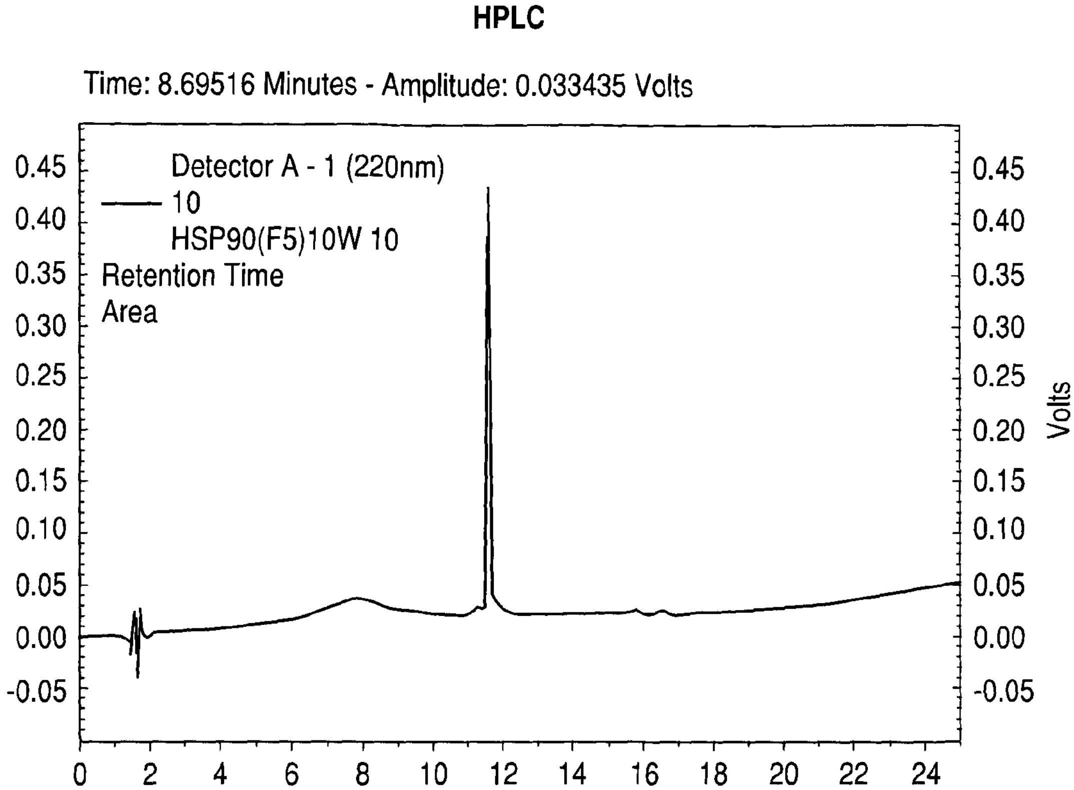
FIG. 7A is the result of the HPLC.
Figure 7B:
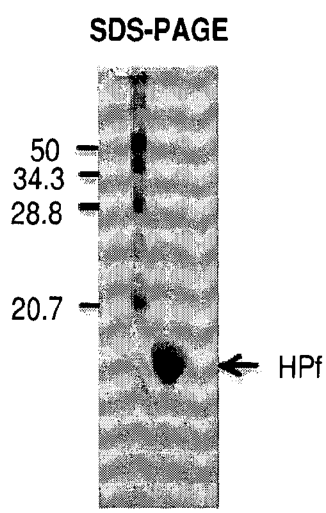
FIG. 7B is the SDS-PAGE, confirming the purity of the purified HPf.

Lanes of electrophoresis results of FIG. 6 indicate the proteins: 1. Marker proteins; 2. Competent cell (negative control); 3. Whole cell lysate; 4. Supernatant fraction after the homogenization (cytosol fraction); 5. Pellet obtained after homogenization (inclusion body fraction); 6. Supernatant after washing the pellet; 7. Dissolved inclusion body; 8-11 Solubilized inclusion body treated with TEV protease. The purity of purified HPf was >95% as determined by HPLC and SDS-PAGE. The yield after the purification was determined to be 0.1-0.2 g/liter (FIG. 7).

Example 5. Analysis of HPf by MALDI-TOF

In order to ensure that the HPf protein from the final purification step was originated from HPS90a, the MALDI-TOF analysis (Voyager-DE STR, Applied BioSystems, USA) was performed. After the electrophoresis of purified HPf (FIG. 7*b*), the bend corresponding to HPf was cut out from the gel with a sharp razor. Then the gel was immersed in 0.1 M $(NH_4)HCO_3$ solution for 1 hr. After the supernatant was removed, the gel was transferred to 50% acetonitrile in 0.1 M $(NH_4)HCO_3$ solution for 1 hr, then in 100% acetonitrile for 15 minutes. Then the in-gel trypsin digest was performed by mixing the gel with protein-sequencing-grade trypsin (Promega, USA) in 25 mM $(NH_4)HCO_3$ for 16 hours at 37° C. Subsequently 5% TFA solution containing 60% acetonitrile was added to terminate the reaction and the mixture was centrifuged. The supernatant was retrieved to determine the molecular weight by the MALDI-TOF analysis. According to the analysis using the protein mass database, the purified protein HPf is a fragment of HSP90a (FIG. 8).

Example 6-1. Analysis of the HPf Particle Size

In order to prepare the nano-liposome encapsulated HPf for the pharmaceutical/cosmetic formulation the HPf particle size was measured using Electrophoretic Light Scattering Spectrophotometer, ELS-8000.

HPf from the final purification step was diluted to 1 mg/ml (or higher concentration) in phosphate buffered saline; pH 7.2, the light scattered intensity, the weight and number of particles were determined using ELS 8000. As shown in the FIGS. 9A-9C, the diameter of the particle was measured to be approximately 10-14 nm. The diameter of the three dimensional structure of HPf monomer was approximately 4.4 nm based on the analysis using the software UCSF Chemera program.

Figures 1D, 9:
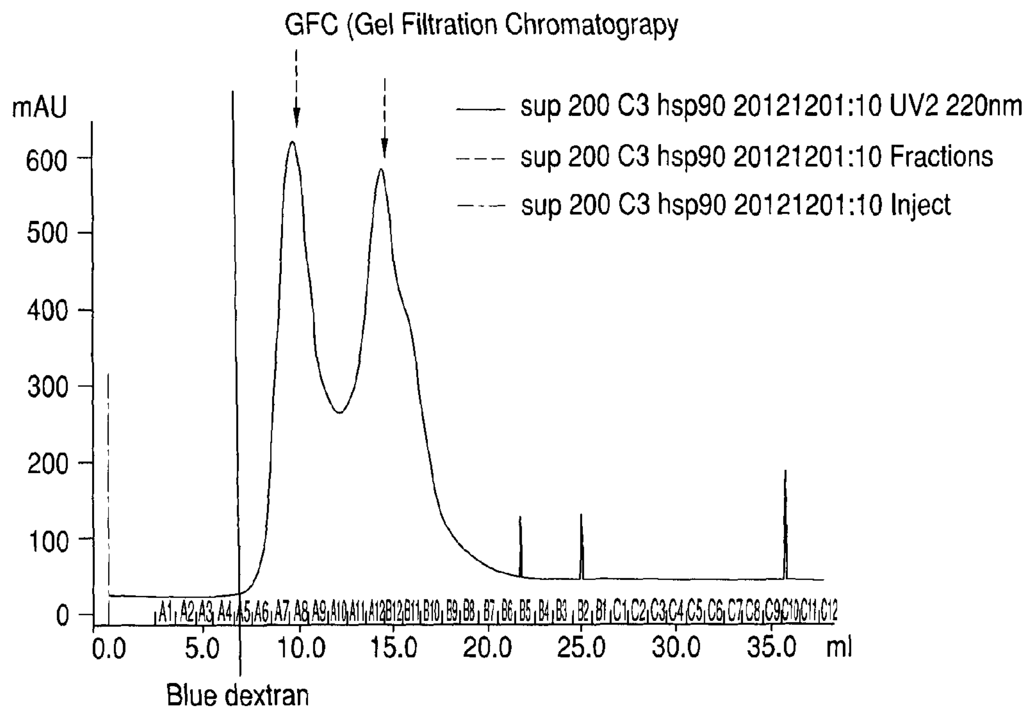
Figures 2, 9:
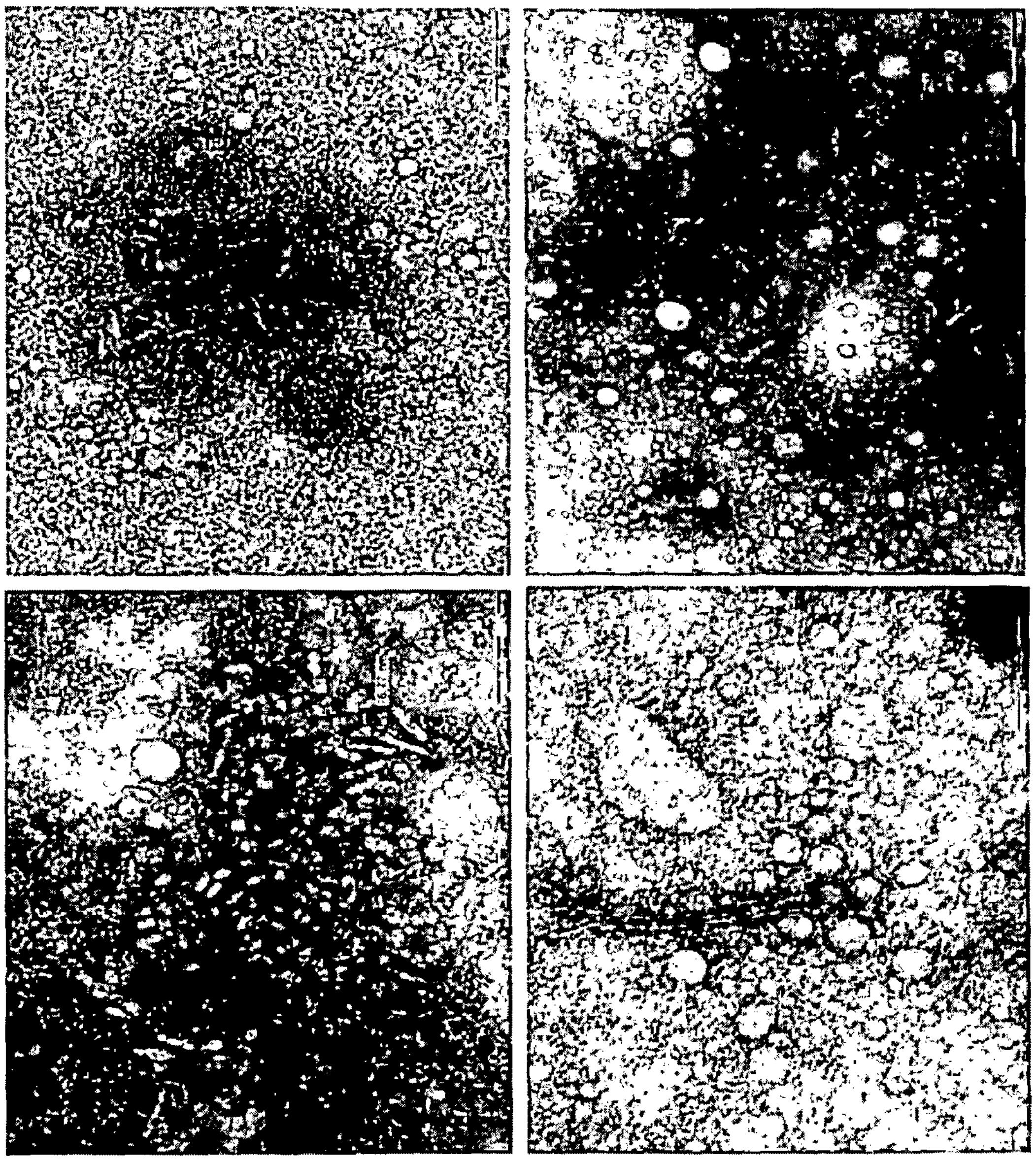

Since the size of monomer and the HPf in solution could be different due to its tendency to oligomerize in solution, its size in solution was measured by gel filtration chromatography. The results demonstrating the peak of HPf immediately following the Blue Dextran (200 kDa, Sigma-Aldrich, USA) indicated that HPf does exist in solution as an oligomeric form (FIG. 9-1D).

Example 6-2. HPf Protein-Size Analysis Via Electron Microscopy

By using a transmission electron microscope (EF-TEM; Energy Filtering-Transmission Electron Microscope, KBSI, Korea), HPf protein particle's size and image were analyzed. The first fixation process was completed by using a 2.5% glutaraldehyde and 4% paraformaldehyde solution, and it was washed with a phosphate buffer solution. Then, the second fixation process was done using with 1% osmium tetroxide, and underwent dehydration steps beginning with 60% ethanol, onto 70%, 80%, 90%, 95% and 100% in ascending order. After embedding with epoxy resin, sample sections were prepared by thin microslicer. Grids were prepared for section platform, and samples were observed after the electrostaining steps. (FIG. 9-2).

Example 7. Evaluation of the Safety of HPf Using Skin Cell Lines

Figures 1, 10A:
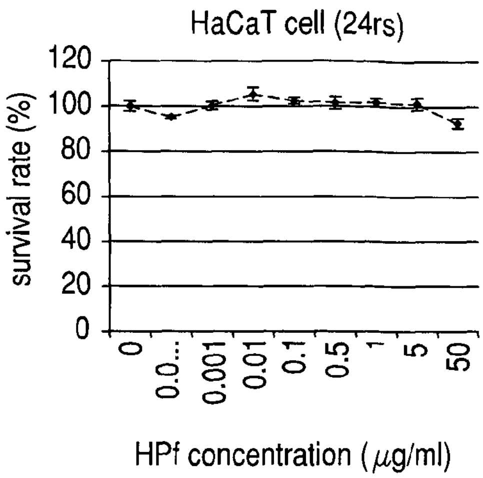
Figures 2, 10A:
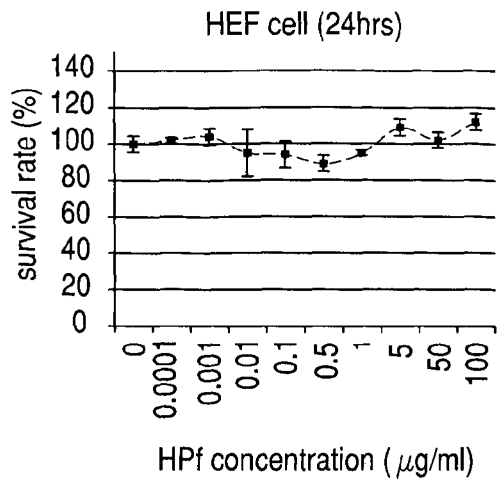
Figures 1, 10B:
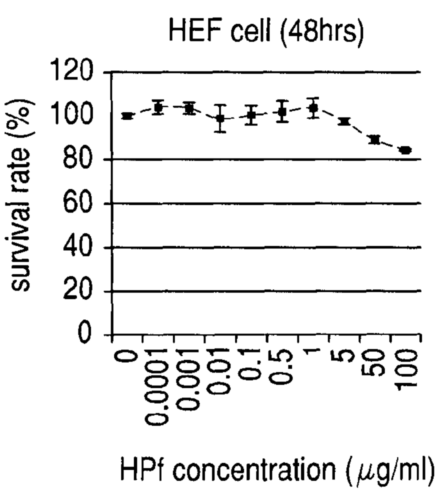
Figures 2, 10B:
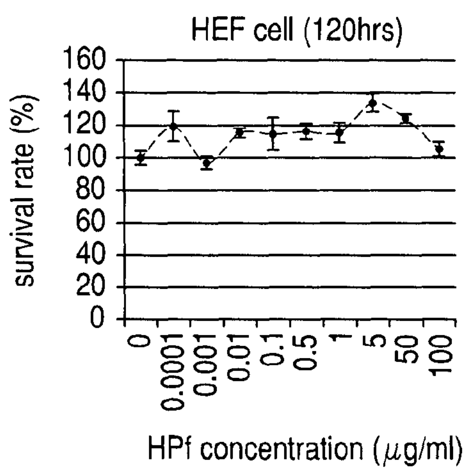
Figures 3, 10B:
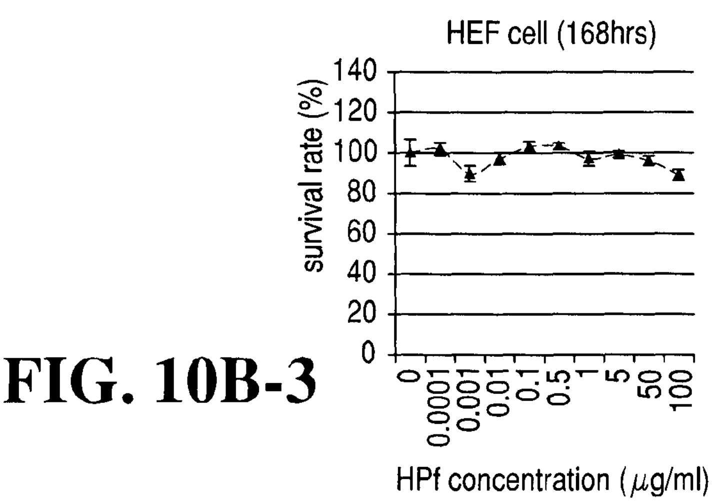

To determine whether HPf is safe for human application, human epidermal cell line (HaCaT) (Schoop, Veronika M., *Journal of Investigative Dermatology.,* 112 (3): 343-353, 1999) and dermal cell line (HEF)(CRL-7039, ATCC, USA) was incubated with HPf. The concentration of HPf used for testing the toxicity was 10-100 times higher than the concentration of epidermal growth factor used in cosmetic products manufactured and marketed by Regeron Inc. (1-10 μg/ml EGF used for the Clairesome-EF product line). Specifically, in 96 well plate 2~10×$10^3$ cells of each cell line were plated and cultured in DMEM media (Hyclone, USA) containing 10% FBS (Fetal Bovine Serum Albumin, Hyclone, USA). HPf was then added to each cell at the concentration of 0, 0.0001, 0.001, 0.01, 0.1, 0.5, 1, 5, 50 and 100 μg/ml, and the plate was incubated at 37° C. in the $CO_2$ incubator for 1 week. The growth rate (%) of cells was determined by mixing 10 μl culture media with 5 mg/ml MTT (3-(4,5-dimethylthiazol-2-yl)-2,5 diphenyltetrazolium bromide, Sigma-Aldrich, USA) and incubated at 37° C. in $CO_2$ incubator for 4 hours. After the insoluble MTT precipitate was dissolved in 10% Triton X-100 and 0.1N HCl the O.D. was measured using spectrophotometer, spectra MAX 190 (Molecular Device, USA) at 595 nm. The cells mixed with 100 μg/ml of HPf maintained the 90% survival rate (FIG. 10A) after incubation for 24 hours, and 85% after 7 days incubation (FIG. 10B). The results indicated that HPf can be safely used as a cosmetic or pharmaceutical ingredient.

Example 8. Stability of HPf in Aqueous Solution

In order to find out how to prevent the physical/chemical instability and the loss of bioactivity of HPf in aqueous solution, the stability of HPf was measured when dissolved in pH 7.2 phosphate buffer solution or kept in a gel state. The gel used for this analysis was prepared by mixing the following compounds. Care was taken to exclude any potentially interfering factors that affect the stability of HPf protein.

TABLE 3

Composition of the gel used for evaluation of the HPf stability

| Compounds | Amount (%) |
|---|---|
| KOH | 0.28 |
| carbomer | 0.4 |
| Glycerin | 10 |
| phenoxyethanol | 0.6 |
| HPf | 1 mg/ml |
| Water | 88.72 |

Figure 11A:
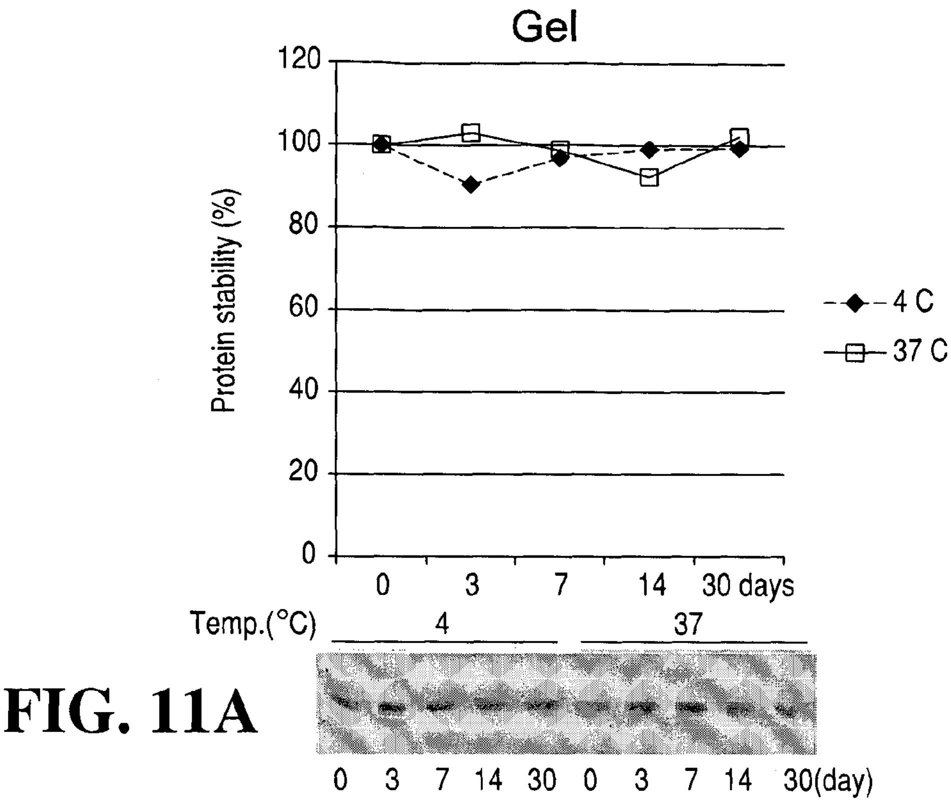
FIG. 11A shows the stability of HPf protein kept in a gel state while varying the temperature and storage time.
Figure 11B:
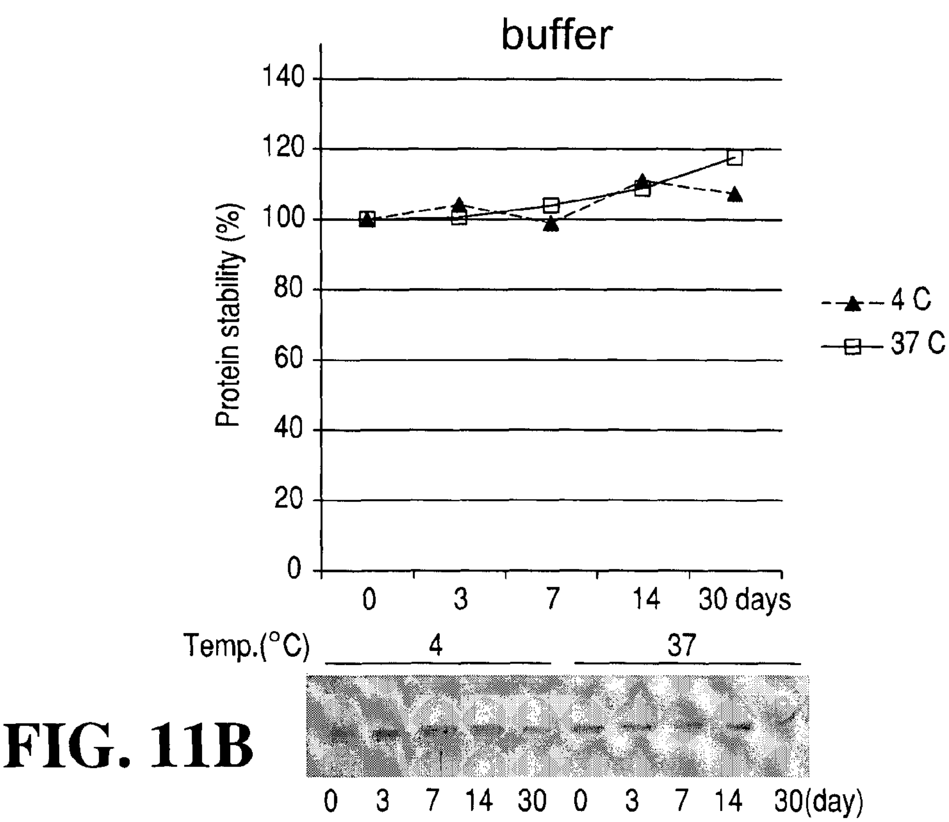
FIG. 11B shows the stability of the HPf protein kept in a buffer solution state while varying the temperature and storage time.
Figure 12:
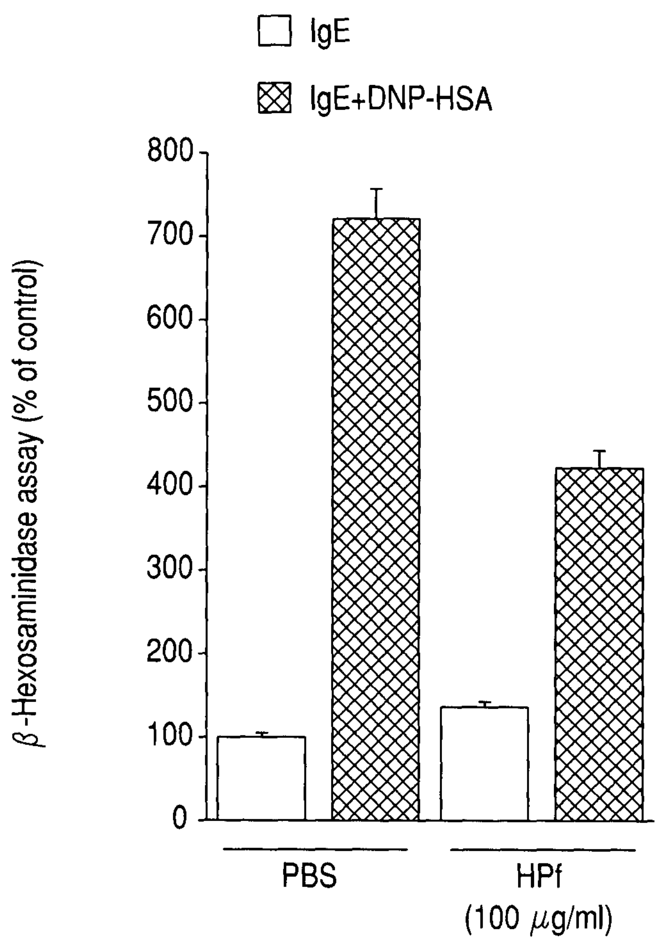
FIG. 12 demonstrates the ability of HPf to inhibit the degranulation in RBL-2H3 cell line as measured by the activity of secreting beta-hexosaminidase.

The stability was evaluated as follows; first, HPf was diluted to 10 μg/ml in phosphate buffer or to 1 mg/ml while tested in the gel state. The solution or the gel was left at 4° C. or 37° C. for one month. The amount and/or the denaturation of the protein was analyzed using Coumassie Brilliant Blue and SDS-PAGE with samples collected on 3, 7, 14, and 30 days from the first day of the experiment. The protein stability was measured using a densitometer (TotalLabQuant, Totallab, USA). As seen in the FIG. 11, the HPf was consistently stable while kept in phosphate buffer or in the gel state at 4° C. and 37° C. for one month.

Example 9. Evaluation of the Efficacy of HPf for Treating Atopic Dermatitis Using Cell Line Models (Anti-Inflammatory Effects of HPf Through Suppressing the Degranulation)

Degranulation of mast cells mediated by IgE is one of the typical symptoms of atopic dermatitis. To evaluate the anti-inflammatory effect of HPf, its activity of inhibiting the secretion of beta hexosaminase, a biomarker for degranulation, was measured using a basophilic cell line RBL-2H3 (CRL-2256, ATCC, USA). First, 2.5×$10^5$ RBL-2H3 cells were plated in each well of 48 well plate and incubated at 37° C. in $CO_2$ incubator for 3 hours. Cells were sensitized by adding IgE to 1.0 μg/ml and incubated for 24 hours. Then the unbound IgE was removed by washing the cells with HBS (HEPES buffered Saline) 4 times. Cells were then stimulated by treating with 800~1000 ng/2,4-dinitrophenyl hapten-human serum albumin (DNP-HSA, Biosearch Technologies, USA). Then 50 μl of the supernatant was mixed with 200 μl 0.05M citrate buffer (pH 4.5) containing 1 mM p-nitrophenyl N-acetyl-beta-glucosamine and left for 1 hour. The reaction was terminated by adding 500 μl 0.05M sodium carbonate buffer (pH10). The O.D was measured at 405 nm using spectrophotometer. The results demonstrated (FIG.

12) that 100 μg/ml HPf inhibited the secretion of beta hexosaminase by 60% when the inhibitory effects were compared with that of the control (treated with PBS). This indicates that HPf is able to significantly ameliorate symptoms of atopic dermatitis by suppressing the degranulation through inhibiting of the beta hexosaminase secretion.

Figure 13A:
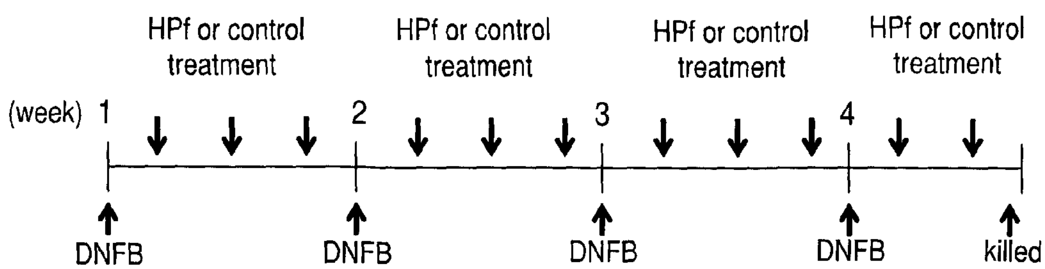
FIG. 13A shows the time line and HPf treatments examined.

Example 10. Evaluation of the Efficacy of HPf for Treating Atopic Dermatitis Using Animal Model 10-1) Effects on the Wound Healing Atopic dermatitis was induced on the skin of NC/Nga mouse by topical administration of 150 μl of 0.15% 2.4-dinitrofluorobenzene (DNFB) (dissolved in acetone:olive oil=3:1) once a week for 4 weeks. The wound healing effects of HPf was determined as follows: first, mice were divided into two groups; one group received topical administration of 100 μl HPf three times per week for 4 weeks, whereas the control group did not receive HPf. (see FIG. 13A for the scheme of the treatment). The degree of skin damage (wound) was determined by the naked eye (FIG. 13B), while the infiltration of immune cells and their recovery were measured by dermal tissue staining (FIG. 14). Compositions either with or without HPf used for the topical administration was prepared as gel in order to keep the HPf stay on the applied area.

TABLE 4

Composition of the gel used for evaluation of the HPf efficacy on treating atopic dermatitis.

| Compounds | Amount (%) Control | Amount (%) HPf treated group |
|---|---|---|
| KOH | 0.28 | 0.28 |
| Carbomer | 0.4 | 0.4 |
| Glycerin | 10 | 10 |
| Phenoxyethanol | 0.6 | 0.6 |
| HPf | — | 1 mg/ml |
| Water | 88.72 | 88.72 |

Figures 1, 13B:
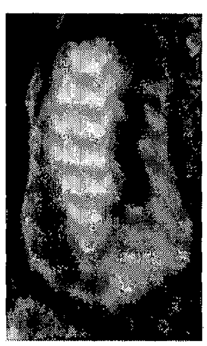
Figures 2, 13B:
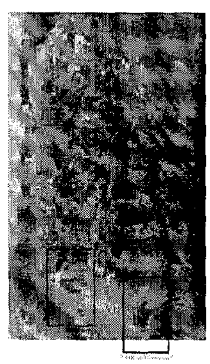
Figures 3, 13B:
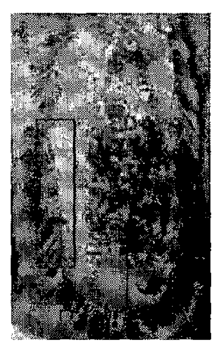
Figures 4, 13B:
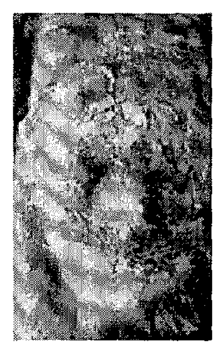
Figures 1, 14A:
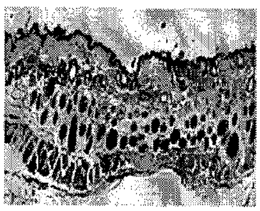
Figures 2, 14A:
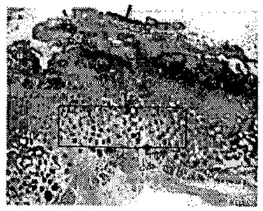
Figures 3, 14A:
Figures 4, 14A:
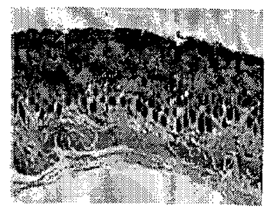
Figures 1, 14B:
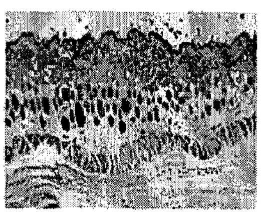
FIG. 14B shows simply the same results with a different corresponding set of hystological specimens. HPf was applied topically on wounds induced by applying DNFB on the NC/Nga mouse skin.
Figures 2, 14B:
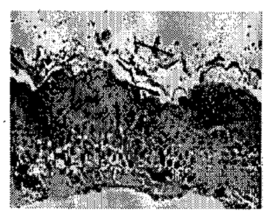
Figures 3, 14B:
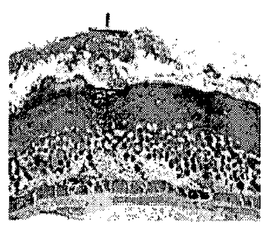
Figures 4, 14B:
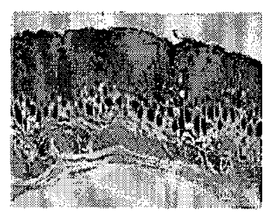

Throughout the animal test period, no skin disorders induced by DNFB were developed except the atopic dermatitis. A topical administration of DNFB on the skinned back of Nc/Nga mouse induced the separation of stratum corneum and inflammation due to the wound (FIG. 13B-2). After 4 weeks of treatment, skin of the treated group, i.e., the group that received DNFB+HPf (FIG. 13B-4), appeared virtually wound-free with a slight mark of keratosis, while the control group demonstrated serious wound left with a visible sign of inflammation and severe keratosis (FIG. 13B-3). These results indicate the efficacy of HPf for ameliorating the symptom of atopic dermatitis.

10-2) Effects of HPf for Wound Healing and for Suppressing the Infiltration of Immune Cells into the Skin Area Affected by Atopic Dermatitis as Shown in Animal Model In order to further evaluate the ability of HPf to heal wounds on Nc/Nga mouse with atopic dermatitis, a peace of skin tissue was cut out after 4 weeks from the treatment and stained with H&E (Hematoxylin & eosin) (FIG. 14). Results demonstrated a marked separation of stratum corneum in the group received DNFB only (FIG. 14A-2, 14B-2) or the control group (FIG. 14A-3, 14B-3) without treatment with HPf, while the skin damage was minimal in the group treated with HPf (FIG. 14A-4, 14B-4) (See the Table 4 for compositions used for the control group). Atopic dermatitis is known to cause the infiltration of immune cells around the affected areas since it tends to secrete various chemoattractive cytokines. According to the H&E staining experiment, the group received DNFB only and the control group without HPf shows the infiltration of immune cells (FIGS. 14A-2, 14B-2 and 14A-3, 14B-3), whereas such an infiltration was minimal in the group treated with HPf (FIG. 14A-4, 14B-4). The results strongly suggest that HPf is capable of suppressing the infiltration of excessive immune cells to the affected areas as well as healing the wound.

Example 11. Effects of HPf on Skin Cell Differentiation

Effects of HPf on the cell differentiation of keratinocyte and fibroblast was evaluated using human epidermal cell line HaCaT (Schoop, Veronika M., *Journal of Investigative Dermatology.,* 112(3): 343-353) and fibroblast cell line CCD-986sk (SCRL-1947, ATCC, USA). After each cell line was treated with HPf (100 μg/ml) for 24 hours RNA was extracted and qRT-PCR (SYBR-Green) was performed.

Specifically, $0.3\times10^6$ cells/ml were plated in 6 well plates, which was incubated in DMEM (Hyclone, USA) containing 10% FBS until cells reached the 70-80% confluency at 37° C. in $CO_2$ incubator. The above cells were treated with HPf to achieve 100 |g/ml as the final concentration and incubated 24 hours. After removing the supernatant, 1 ml TRizol solution (Invitrogen USA) was added to dissolve the cells. Then 200 |l chloroform was added followed by vortexing for 10 sec. and centrifuged at 12,000×g (Centrifuge 5418, Eppendorf, USA) for 15 minutes. The supernatant was collected in a new e tube and mixed with 0.5 ml isopropyl alcohol and recentrifuged for 10 min. to precipitate the total RNA. The total RNA was washed with 70% ethanol once then dissolved in water free of RNAse and DNAse. Such purified RNA was used to construct the cDNA library. The cDNA was synthesized using Omniscript Reverse Transcription kit (Qiagen, U.S.A.) following the instruction provided in the manufacturer's manual.

First, the total RNA 1 μg, 1×RT buffer, dNTP mix, oligo-dT primers, RNAse inhibitors and Omniscript Reverse Transcriptase were mixed, then water free of DNase and RNase was added to adjust the volume to 20 μl, which then was incubated at 37° C. for 60 minutes to obtain cDNAs.

The expression level of marker genes, such as keratin 10 (KRT10), transglutaminase 1 (TGM1) and involucrin (IVL), which represents the degree of cell differentiation were determined by RT-PCR (LightCycler 480, Roche, USA). Sequences of the primers for RT-PCR are shown in the Table 5. Reagents for the RT-PCR were SYBR green PCR master mix purchased from Applied Biosystem. The PCR was initiated by denaturation at 95° C., 10 seconds, followed by annealing at 60° C., 10 seconds and amplification at 72° C., 10 seconds. The cycle was repeated for 45 times.

Figure 15A:
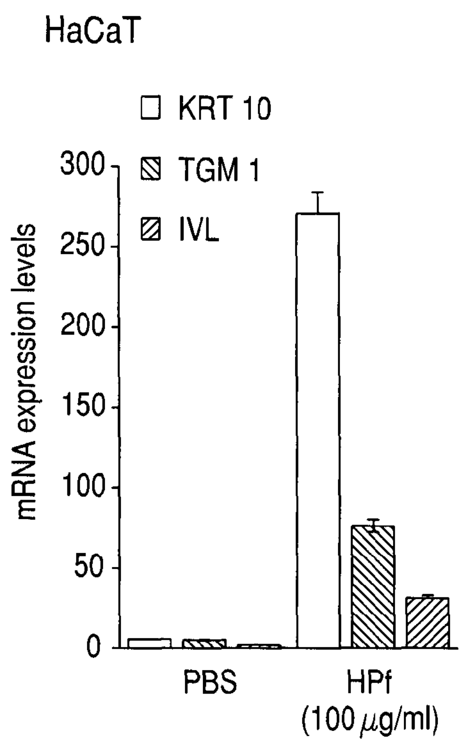
FIG. 15A shows the expression level of KRT10 (Keratin 10), TGM 1 (Transglutaminase 1) or IVL (involucrin) genes in an epidermal cell line (HaCaT) (a keratinocyte).
Figure 15B:
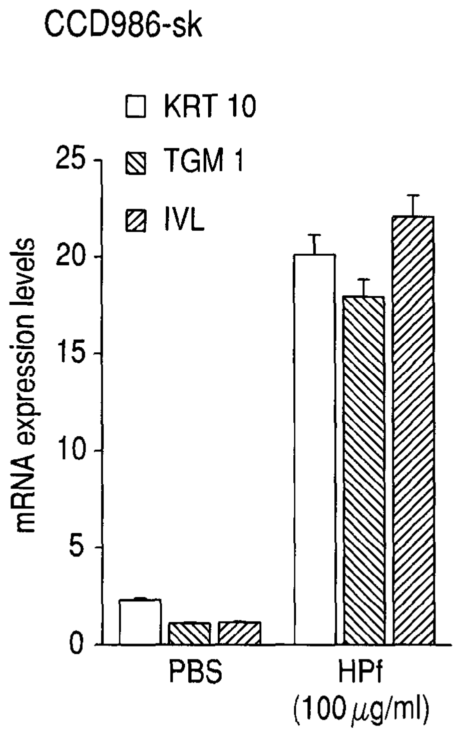
FIG. 15 B shows the expression level of KRT10, TGM 1 or IVL genes in a dermal cell line (CCD986-sk) (a fibroblast) treated with HPf or PBS (control). In the course of skin epidermal stem cell differentiation, keratinocytes increase the expression of genes related to Keratin 10, Transglutaminase 1 and involucrin. Thus, the KRT10, TGM 1 or IVL genes are used as markers that reflect the degree of cell differentiation in keratinocyte cells.

The melting curve analysis was performed at the final cycle of the RT-PCR to confirm the absence of nonspecific bands. The RT-PCR products were analyzed ddCt algorithm (Δ-Δ-Ct) and the results are demonstrated in FIG. 15. They indicate that when HaCaT cells were treated with HPF, the expression level of marker genes for cell differentiation was 20-250 higher than that of the control cell (FIG. 15A). In the case of CCD986-sk cell, the expression level of marker genes was 20 times higher than that of the control cells (FIG. 15B) when treated with HPf.

These results suggest that HPf plays important role in controlling skin cell differentiation hence can be effectively used as an active ingredient in wound healing medicine and/or cosmetic products.

TABLE 5

| Sequences of the primers for RT-PCR | | | |
|---|---|---|---|
| Gene | Direction | Sequences | Seq. No. |
| KRT10 | Sense | 5'-GGTGGGAGTTATGGAGGCAG-3' | 28 |
| | Antisense | 5'-CGAACTTTGTCCAAGTAGGAAGC-3' | 29 |
| TGM1 | Sense | 5'-CATCAAGAATGGCCTGGTCT-3' | 30 |
| | Antisense | 5'-CAATCTTGAAGCTGCCATCA-3' | 31 |
| IVL | Sense | 5'-TCCTCCAGTCAATACCCATCAG-3' | 32 |
| | Antisense | 5'-CAGCAGTCATGTGCTTTTCCT-3' | 33 |

Example 12: Effects of HPf on Subcutaneous Fat Cell Differentiation In Vitro

Figure 16A:
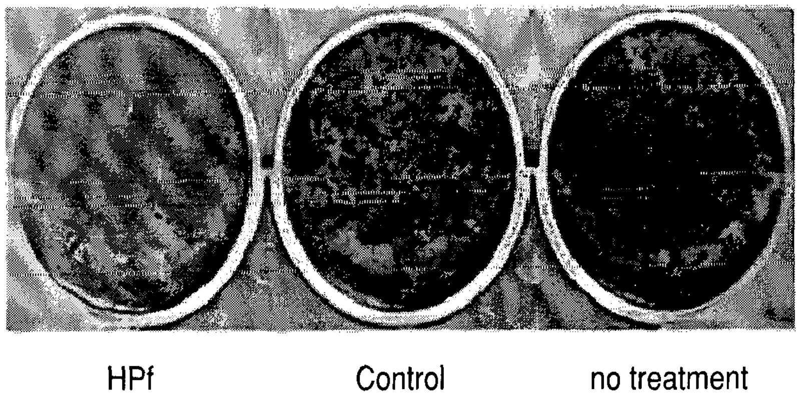
FIG. 16 shows the effects of HPf on the subcutaneous fat cell differentiation confirmed by Red O stain (FIG. 16A) and its graphical representation (FIG. 16B).
Figure 16B:
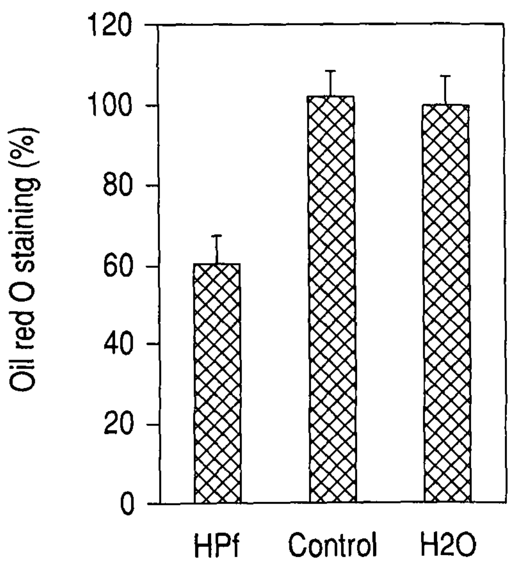

Subcutaneous fat cells secrete various factors necessary to maintain their structure properly and contain cells that are yet to be differentiated, such as pre-adipocytes and fat stem cell. We carried out experiments to find out whether HPf might promote or suppress the fat cell differentiation. After 3T3-L1 cell line (CL-173, ATCC, USA) was treated with HPf (100 ug/ml) or with PBS (pH 7.2) for the control, cells were stained with Oil Red O stain in order to determine the effect of HPf on the fat cell differentiation. As seen in FIG. 16, we were able to prove for the first time in this field of research that cells treated with HPf display 40% reduction in the fat cell differentiation when compared to that of control cell.

Example 13. Evaluation of Skin Condition Improving Effects of HPf Using Artificial Skin The present inventors have investigated the effects of HPf on skin conditioning using artificial skin which has a very similar 3D structure to human skin. The 3D artificial skin culture was carried out using the Neoderm ED product (TEGO Cell Science Inc., Korea) by following the protocols provided by the manufacturer. Neoderm ED product has epidermal and dermal tissue structure that is similar to human, hence has been frequently utilized for developing novel pharmaceuticals for skin as well as cosmetic products.

After collagen matrix and fibroblast cells were grown with media on the surface of cell culture vessels, keratinocytes were plated on the surface and cultured for 4 days to obtain monolayer cell. The monolayer of dermal cell was induced by exposing the cells to air for 16-20 days. Subsequently the artificial dermal layer was treated with 100 μg/ml HPf or with phosphate buffered saline (pH 7.2) for 7 days. Then the epidermis and dermis were stained with H&E stain. FIG. 17 demonstrates that there are no changes in the thickness of epidermal layers in the control (FIG. 17 A—C1-C3) and HPf treated groups (FIG. 17 B—H1-H4), while the HPf treated group displayed 2 fold increase in the thickness of dermal layers when compared to the control groups. This results clearly indicate that HPf promote the cell differentiation and growth of dermal layer, implicating that the expression of major skin tissue components, such as collagen and elastin may be induced by HPf. Therefore, we suggest that HPf can be used as an active ingredient for improving wrinkles or elasticity, and for developing skin condition improving cosmetic products.

Example 14. Effects of HPf on Inhibiting Melanin Biosynthesis

Figure 18A:
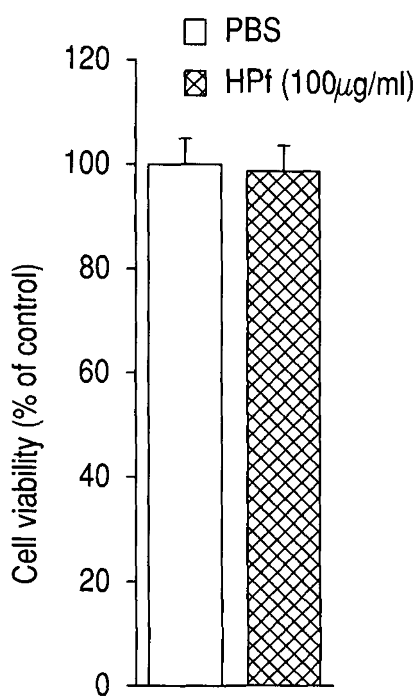
FIG. 18A—Cell viability after application of 100 μg/ml HPf. HPf does not affect cell viability.
Figure 18B:
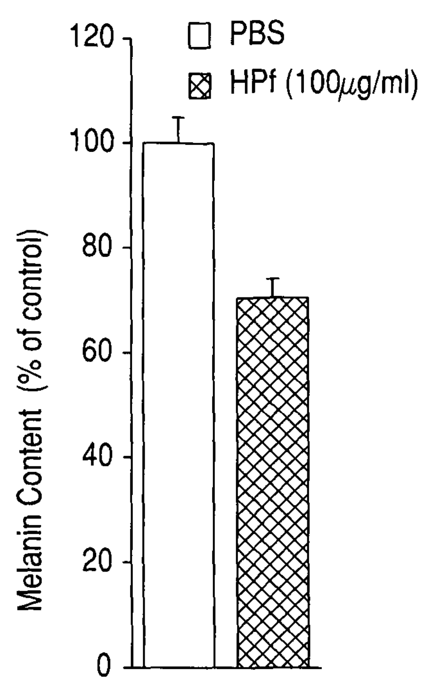
FIG. 18B—Melanin Content after application of 100 μg/ml HPf. HPf inhibits melanin biosynthesis.

Inhibitory effects of HPf on the melanin biosynthesis were examined in order to determine whether HPf might be effective on skin whitening. After B16F10 cell line (CRL-6475, ATCC, USA) was treated with HPf (100 μg/ml) or PBS for 48 hours. The cell survival rate and melanin biosynthesis were measured by MTT assay as shown in FIG. 18. The addition of 100 μg/ml HPf into the culture reduced the melanin biosynthesis 70% when compared to the control, suggesting that HPf has strong effect on skin whitening. In a safety test, 100 μg/ml HPf did not affect the survival of cells indicating no toxicity of HPf at this concentration.

Example 15. Manufacture of Lipo-HPf, HPf Encapsulated in Nano-Liposomes

The following materials were used for manufacturing Lipo-HPf; soybean lecithin (Shindongbang Inc., Korea) as the phospholipid, Metarin P (Degussa Texturant Systems Deutschland GmbH & Co. KG), Nutripur S (Degussa Texturant Systems Deutschland GmbH & Co. KG) or Emultop (Degussa Texturant Systems Deutschland GmbH & Co. KG).

The heat exchanger of a high-pressure homogenizer (max. output 5 L/hr, highest pressure 1200 bar, Model HS-1002; manufactured by Hwasung Machinery Co., Ltd., South Korea) was placed in ice water such that the temperature of the outlet of the homogenizer did not exceed 30° C., In the meantime the inside of the homogenizer was then washed with distilled water so as to be ready to operate. Then, HPf was dissolved in a buffer solution (20 mM $NaH_2PO_4$ pH 6.5-7.5, 1 mM EDTA) at a concentration of 1 mg/ml, phospholipid was added at a ratio of 10 w/v % and sufficiently hydrated and stirred. The stirred solution was passed through the homogenizer three times or more at room temperature and a low pressure of 0 bar. To the solution passed through the homogenizer, phospholipid was added to a ratio of 14 w/v % and sufficiently hydrated and stirred. The stirred solution was passed through the homogenizer three times or more at 100 bar. Then, to this solution phospholipid was added to a ratio of 18 w/v %, sufficiently hydrated and stirred, and passed through the homogenizer three times or more at 200 bar. Then, to this solution phospholipid was added to a ratio of 20 w/v %, sufficiently hydrated and stirred, and passed through the homogenizer three times or more at 300 bar. Then to this solution, phospholipid was added to a ratio of 22 w/v %, sufficiently hydrated and stirred, and passed through the homogenizer three times or more at 400 bar. Then, to the solution passed through the homogenizer in the condition of 400 bar, phospholipid was added to a ratio of 24 w/v %, sufficiently hydrated and stirred, and passed through the homogenizer three times or more at 500 bar. Then, to the solution passed through the homogenizer in the condition of 500 bar, phospholipid was added to a ratio of 26 w/v %, sufficiently hydrated and stirred, and passed through the homogenizer three times or more at 600 bar. Then, to the solution passed through the homogenizer in the condition of 600 bar, phospholipid was added to a ratio of 28 w/v %, sufficiently hydrated and stirred, and passed through the homogenizer three times or more at 700 bar. Then this solution was passed through the homogenizer three times or more at 800 bar followed by centrifugation at 15,000×g for 30 minutes. The supernatant was then passed through gel chromatography (GE Healthcare, USA) to eliminate HPf which was not encapsulated by liposome, hence preparing HPf-containing liposome (Lipo-HPf) liquid formulation.

For a topical preparation, it is envisioned that the product will include an effective dose estimate of about 100 ng/ml to about 1 mg/ml of each of the HPf polypeptide, the polypeptide fragments, or a mixture thereof.

Having described specific examples of the present invention, it is understood that variants and modifications thereof falling within the spirit of the invention may become apparent to those skilled in the art. The scope of the invention is not intended to be limited to those embodiments provided in the examples. The appended claims and their equivalents provide a determination of the scope of the invention.

SEQUENCE LISTING

```
Sequence I.D. No. 1-Amino acid sequence for HPf
Glu Glu Lys Glu Asp Lys Glu Glu Glu Lys Glu Lys Glu Glu Lys Glu Ser Glu Asp Lys Pro
Glu Ile Glu Asp Val Gly Ser Asp Glu Glu Glu GluLys Lys Asp Gly Asp Lys Lys Lys Lys
Lys Lys Ile Lys Glu Lys Tyr Ile Asp Gln Glu Glu Leu Asn LysThr Lys Pro Ile Trp Thr Arg
Asn Pro Asp Asp Ile Thr Asn Glu Glu Tyr Gly Glu Phe Tyr Lys Ser Leu Thr Asn Asp Trp
Glu Asp His Leu Ala Val Lys His Phe Ser Val Glu Gly Gln Leu Glu Phe Arg Ala Leu Leu
Phe Val Pro Arg Arg Ala Pro Phe Asp

Sequence I.D. No. 2-Full amino acid sequence for HSP90a
MetProGluGluThrGlnThrGlnAspGlnProMetGluGluGluGluValGluThrPheAlaPheGlnAlaGlu
IleAlaGlnLeuMetSerLeuIleIleAsnThrPheTyrSerAsnLysGluIlePheLeuArgGluLeuIleSerAsn
SerSerAspAlaLeuAspLysIleArgTyrGluSerLeuThrAspProSerLysLeuAspSerGlyLysGluLeu
HisIleAsnLeuIleProAsnLysGlnAspArgThrLeuThrIleValAspThrGlyIleGlyMetThrLysAlaAsp
LeuIleAsnAsnLeuGlyThrIleAlaLysSerGlyThrLysAlaPheMetGluAlaLeuGlnAlaGlyAlaAsp
IleSerMetIleGlyGlnPheGlyValGlyPheTyrSerAlaTyrLeuValAlaGluLysValThrValIleThrLys
HisAsnAspAspGluGlnTyrAlaTrpGluSerSerAlaGlyGlySerPheThrValArgThrAspThrGlyGlu
ProMetGlyArgGlyThrLysValIleLeuHisLeuLysGluAspGlnThrGluTyrLeuGluGluArgArgIle
LysGluIleValLysLysHisSerGlnPheIleGlyTyrProIleThrLeuPheValGluLysGluArgAspLysGlu
ValSerAspAspGluAlaGluGluLysGluAspLysGluGluGluLysGluLysGluGluLysGluSerGluAsp
LysProGluIleGluAspValGlySerAspGluGluGluGluLysLysAspGlyAspLysLysLysLysLysLys
IleLysGluLysTyrIleAspGlnGluGluLeuAsnLysThrLysProIleTrpThrArgAsnProAspAspIleThr
AsnGluGluTyrGlyGluPheTyrLysSerLeuThrAsnAspTrpGluAspHisLeuAlaValLysHisPheSer
ValGluGlyGlnLeuGluPheArgAlaLeuLeuPheValProArgArgAlaProPheAspLeuPheGluAsn
ArgLysLysLysAsnAsnIleLysLeuTyrValArgArgValPheIleMetAspAsnCysGluGluLeuIlePro
GluTyrLeuAsnPheIleArgGlyValValAspSerGluAspLeuProLeuAsnIleSerArgGluMetLeuGln
GlnSerLysIleLeuLysValIleArgLysAsnLeuValLysLysCysLeuGluLeuPheThrGluLeuAlaGlu
AspLysGluAsnTyrLysLysPheTyrGluGlnPheSerLysAsnIleLysLeuGlyIleHisGluAspSerGln
AsnArgLysLysLeuSerGluLeuLeuArgTyrTyrThrSerAlaSerGlyAspGluMetValSerLeuLysAsp
TyrCysThrArgMetLysGluAsnGlnLysHisIleTyrTyrIleThrGlyGluThrLysAspGlnValAlaAsn
SerAlaPheValGluArgLeuArgLysHisGlyLeuGluValIleTyrMetIleGluProIleAspGluTyrCysVal
GlnGlnLeuLysGluPheGluGlyLysThrLeuValSerValThrLysGluGlyLeuGluLeuProGluAspGlu
GluGluLysLysLysGlnGluGluLysLysThrLysPheGluAsnLeuCysLysIleMetLysAspIleLeuGlu
LysLysValGluLysValValValSerAsnArgLeuValThrSerProCysCysIleValThrSerThrTyrGly
TrpThrAlaAsnMetGluArgIleMetLysAlaGlnAlaLeuArgAspAsnSerThrMetGlyTyrMetAlaAla
LysLysHisLeuGluIleAsnProAspHisSerIleIleGluThrLeuArgGlnLysAlaGluAlaAspLysAsn
AspLysSerValLysAspLeuValIleLeuLeuTyrGluThrAlaLeuLeuSerSerGlyPheSerLeuGluAsp
ProGlnThrHisAlaAsnArgIleTyrArgMetIleLysLeuGlyLeuGlyIleAspGluAspAspProThrAla
AspAspThrSerAlaAlaValThrGluGluMetProProLeuGluGlyAspAspAspThrSer
ArgMetGluGluValAsp

Sequence I.D. No. 3 - Base sequence for HPf
atggaagaaa aggaagacaa agaagaagaa aaagaaaaag aagagaaaga gtcggaagac    60
aaacctgaaa ttgaagatgt tggttctgat gaggaagaag aaaagaagga tggtgacaag   120
aagaagaaga agaagattaa ggaaaagtac atcgatcaag aagagctcaa caaaacaaag   180
cccatctgga ccagaaatcc cgacgatatt actaatgagg agtacggaga attctataag   240
agcttgacca atgactggga agatcacttg gcagtgaagc atttttcagt tgaaggacag   300
ttggaattca gagcccttct atttgtccca cgacgtgctc cttttgatta a            351

Sequence I.D. No. 4-Base sequence for FOR primer HPf-up
GAGACATATGGAAGAAAAGGAAGACAAAGAAGAAGAA

Sequence I.D. No. 5-Base sequence for FOR primer HPf-dn
TATAGGTACCTTAATCAAAAGGAGCACGTCGTGGGACA

Sequence I.D. No. 6-Base sequence for FOR primer HPfΔC1-dn
GGGGTACCTCATTCCAACTGTCCTTCAACTGAA

Sequence I.D. No. 7-Base sequence for FOR primer HPfΔC2-dn
GGGGTACCTCAATCTTCCCAGTCATTGGTCAAG
```

-continued

SEQUENCE LISTING

Sequence I.D. No. 8-Base sequence for FOR primer TRX-up
TTAATTCATATGAGCGATAAAATTATTCACC Sequence I.D. No. 9-Base sequence for FOR primer TRX-NGc-dn
ACCGTTTTTGAACAGCAGC Sequence I.D. No. 10-Base sequence for KR primer TRX-TEVc-dn
CTGGAAGTACAGGTTTTCGGATCCATTACCGTTTTTGAACAGCAGCAG Sequence I.D.No. 11-Base sequence for PCR primer HPf-NGc-up
GCTGCTGTTCAAAAACGGTGAAGAAAAGGAAGACAAAGAAGAAGAA Sequence I.D. No. 12-Base sequence for PCR primer HPf-TEVc-up
GGATCCGAAAACCTGTACTTCCAGGGTGAAGAAAAGGAAGACAAAGAAGAAGAA Sequence I.D. No. 13-Base sequence for FOR primer HGH-Nde-up
GAGACATATGTTCCCGACCATCCCGCTGTCT Sequence I.D. No. 14-Base sequence for FOR primer HGH-7His-dn
TTTCGGATCCAGAACCATGATGATGGTGATGATGATGACCGAAGCCACAGCTGCCCTC Sequence I.D. No. 15-Base sequence for FOR primer HSP90(full)-up
GAGACATATGCCTGAGGAAACCCAGACCCAGACCC Sequence I.D. No. 16-Base sequence for FOR primer HSP90(full)-dn
TATAGGTACCTTAGTCTACTTCTTCCATGCGTGAT Sequence I.D. No. 17-Base sequence for FOR primer HSP90-5p(mid)
ACTGGCGGAAGATAAAGAGAA Sequence I.D. No. 18-Base sequence for TRX(NGc)
ATGAGCGATA AAATTATTCA CCTGACTGAC GACAGTTTTG ACACGGATGT ACTCAAAGCG 60
GACGGGGCGA TCCTCGTCGA TTTCTGGGCA GAGTGGTGCG GTCCGTGCAA AATGATCGCC 120
CCGATTCTGG ATGAAATCGC TGACGAATAT CAGGGCAAAC TGACCGTTGC AAAACTGAAC 180
ATCGATCAAA ACCCTGGCAC TGCGCCGAAA TATGGCATCC GTGGTATCCC GACTCTGCTG 240
CTGTTCAAAA ACGGT 255

Sequence I.D. No. 19-Base sequence for TRX(TEVc)
ATGAGCGATA AAATTATTCA CCTGACTGAC GACAGTTTTG ACACGGATGT ACTCAAAGCG 60
GACGGGGCGA TCCTCGTCGA TTTCTGGGCA GAGTGGTGCG GTCCGTGCAA AATGATCGCC 120
CCGATTCTGG ATGAAATCGC TGACGAATAT CAGGGCAAAC TGACCGTTGC AAAACTGAAC 180
ATCGATCAAA ACCCTGGCAC TGCGCCGAAA TATGGCATCC GTGGTATCCC GACTCTGCTG 240
CTGTTCAAAA ACGGTAATGG ATCCGAAAAC CTGTACTTCC AG 282

Sequence I.D. No. 20-Amino acid sequence for HPfΔC1
Glu Glu Lys Glu Asp Lys Glu Glu Glu Lys Glu Lys Glu Glu Lys Glu Ser Glu Asp Lys Pro
Glu Ile Glu Asp Val Gly Ser Asp Glu Glu Glu GluLys Lys Asp Gly Asp Lys Lys Lys Lys
Lys Lys Ile Lys Glu Lys Tyr Ile Asp Gln Glu Glu Leu Asn Lys Thr Lys Pro Ile Trp Thr Arg
Asn Pro Asp Asp Ile Thr Asn Glu Glu Tyr Gly Glu Phe Tyr Lys Ser Leu Thr Asn Asp Trp
Glu Asp His Leu Ala Val Lys His Phe Ser Val Glu Gly Gln Leu Glu Sequence I.D. No. 21-Amino acid sequence for HPfΔC2
Glu Glu Lys Glu Asp Lys Glu Glu Glu Lys Glu Lys Glu Glu Lys Glu Ser Glu Asp Lys Pro
Glu Ile Glu Asp Val Gly Ser Asp Glu Glu Glu GluLys Lys Asp Gly Asp Lys Lys Lys Lys
Lys Lys Ile Lys Glu Lys Tyr Ile Asp Gln Glu Glu Leu Asn Lys Thr Lys Pro Ile Trp Thr Arg
Asn Pro Asp Asp Ile Thr Asn Glu Glu Tyr Gly Glu Phe Tyr Lys Ser Leu Thr Asn Asp Trp
Glu Asp Sequence I.D. No. 22-Base sequence for HPfΔC1
atggaagaaa aggaagacaa agaagaagaa aaagaaaaag aagagaaaga gtcggaagac 60
aaacctgaaa ttgaagatgt tggttctgat gaggaagaag aaaagaagga tggtgacaag 120
aagaagaaga agaagattaa ggaaaagtac atcgatcaag aagagctcaa caaaacaaag 180
cccatctgga ccagaaatcc cgacgatatt actaatgagg agtacggaga attctataag 240
agcttgacca atgactggga agatcacttg gcagtgaagc atttttcagt tgaaggacag 300
ttggaatga 309

Sequence I.D. No. 23-Base sequence for HPfΔC2
atggaagaaa aggaagacaa agaagaagaa aaagaaaaag aagagaaaga gtcggaagac 60
aaacctgaaa ttgaagatgt tggttctgat gaggaagaag aaaagaagga tggtgacaag 120
aagaagaaga agaagattaa ggaaaagtac atcgatcaag aagagctcaa caaaacaaag 180
cccatctgga ccagaaatcc cgacgatatt actaatgagg agtacggaga attctataag 240
agcttgacca atgactggga agattga 267

Sequence I.D. No. 24-Base sequence for MBP(TEVc)-HPf
ATGAAAATCG AAGAAGGTAA ACTGGTAATC TGGATTAACG GCGATAAAGG CTATAACGGT 60
CTCGCTGAAG TCGGTAAGAA ATTCGAGAAA GATACCGGCA TTAAAGTCAC CGTTGAGCAT 120
CCGGATAAAC TGGAAGAGAA ATTCCCGCAG GTTGCGGCAA CTGGCGATGG CCCTGACATT 180

-continued

SEQUENCE LISTING

```
ATCTTCTGGG CACACGACCG CTTTGGTGGC TACGCTCAAA GCGGCCTGTT GGCTGAAATC   240
ACCCCGGACA AAGCGTTCCA GGACAAGCTG TATCCGTTTA CCTGGGATGC CGTACGTTAC   300
AACGGCAAGC TGATTGCTTA CCCGATCGCT GTTGAAGCGT TAAGCCTGAT TTATAACAAA   360
GACCTGCTGC CGAACCCACC GAAAACCTGG GAAGAGATCC CGGCGCTGGA TAAAGAACTG   420
AAAGCGAAAG GTAAGAGCGC GCTGATGTTC AACCTGCAAG AACCGTACTT CACCTGGCCG   480
CTGATTGCTG CTGACGGGGG TTATGCGTTC AAGTATGAAA ACGGCAAGTA CGACATTAAA   540
GACGTGGGCG TGGATAACGC TGGCGCGAAA GCGGGTCTGA CCTTCCTGGT TGACCTGATT   600
AAAAACAAAC ACATGAATGC AGACACCGAT TACAGCATCG CAGAAGCTGC CTTTAATAAA   660
GGCGAAACAG CGATGACCAT CAACGGCCCG TGGGCATGGA GCAACATCGA CACCAGCAAA   720
GTGAATTATG GTGTAACGGT ACTGCCGACC TTCAAGGGTC AACCGTCCAA ACCGTTCGTT   780
GGCGTGCTGA GCGCAGGTAT TAACGCCGCC AGCCCGAACA AAGAGCTGGC AAAAGAGTTC   840
CTCGAAAATT ATCTGCTGAC TGATGATGGT CTGGAAGCGG TTAATAAAGA CAAACCGCTG   900
GGTGCCGTAG CGCTGAAGAG CTACGAAGAA GAGTTGGTGA ATGATCCGCG TATTGCCGCC   960
ACTATGGAAA ACGCCCAGAA AGGTGAAATC ATGCCGATCA TCCCGCAGAT GAGCGTTTTG  1020
TGGTATGCCG TGCGTACTGC GGTGATCAAC GCCGCCAGCG GTCGTCAGAC TGTCGATGAA  1080
GCCCTGAAAG ACGCGCAGAC TATGATTAAC GGCGATGGTG CTGGTCTGGA AGTGCTGTTT  1140
CAGGGTCCGG AGCTAGGATC CGAAAACCTG TACTTCCAGG GTGAAGAAAA GGAAGACAAA  1200
GAAGAAGAAA AAGAAAAAGA AGAGAAAGAG TCGGAAGACC AACAAGAAAT TGAAGATGTT  1260
GGTTCTGATG AGGAAGAAGA AAAGAAGGAT GGTAACAAGA AGAAGAAGAA GATTAAGGAA  1320
AAGTACATCG ATCAAGAAGA GCTCAACAAA ACAAAGCCCA TCTGGACCAG AAATCCCGAC  1380
GATATTACTA ATGAGGAGTA CGGAGAATTC TATAAGAGCT TGACCAATGA CTGGGAAGAT  1440
CACTTGGCAG TGAAGCATTT TTCAGTTGAA GGACAGTTGG AATTCAGAGC CCTTCTATTT  1500
GTCCCACGAC GTGCTCCTTT TGATTAA                                      1527
```

Sequence I.D.No. 25-Base sequence for HGH(TEVc)-HPf

```
ATGTTCCCGA CCATCCCGCT GTCTCGTCTG TTTGACAACG CTATGCTCCG CGCCCATCGT    60
CTGCACCAGC TGGCCTTTGA CACCTACCAG GAGTTTGAAG AAGCCTATAT CCCAAAGGAA   120
CAGAAGTATT CATTCCTGCA GAACCCCCAG ACCTCCCTCT GTTTCTCAGA GTCTATTCCG   180
ACACCCTCCA ACAGGGAGGA AACACAACAG AAATCCAACC TAGAGCTGCT CCGCATCTCC   240
CTGCTGCTCA TCCAGTCGTG GCTGGAGCCC GTGCAGTTCC TCAGGAGTGT CTTCGCCAAC   300
AGCCTGGTGT ACGGCGCCTC TGACAGCAAC GTCTATGACC TCCTAAAGGA CCTAGAGGAA   360
GGCATCCAAA CGCTGATGGG GAGGCTGGAA GATGGCAGCC CCCGGACTGG GCAGATCTTC   420
AAGCAGACCT ACAGCAAGTT CGACACAAAC TCACACAACG ATGACGCACT ACTCAAGAAC   480
TACGGGCTGC TCTACTGCTT CAGGAAGGAC ATGGACAAGG TCGAGACATT CCTGCGCATC   540
GTGCAGTGCC GCTCTGTGGA GGGCAGCTGT GGCTTCGGTC ATCATCATCA CCATCATCAT   600
GGTTCTGGAT CCGAAAACCT GTACTTCCAG GGTGAAGAAA AGGAAGACAA AGAAGAAGAA   660
AAAGAAAAAG AAGAGAAAGA GTCGGAAGAC AAACCTGAAA TTGAAGATGT TGGTTCTGAT   720
GAGGAAGAAG AAAAGAAGGA TGGTGACAAG AAGAAGAAGA AGAAGATTAA GGAAAAGTAC   780
ATCGATCAAG AAGAGCTCAA CAAAACAAAG CCCATCTGGA CCAGAAATCC CGACGATATT   840
ACTAATGAGG AGTACGGAGA ATTCTATAAG AGCTTGACCA ATGACTGGGA AGATCACTTG   900
GCAGTGAAGC ATTTTTCAGT TGAAGGACAG TTGGAATTCA GAGCCCTTCT ATTTGTCCCA   960
CGACGTGCTC CTTTTGATTA A                                             981
```

Sequence I.D. No. 26-Base sequence for HSP90a full CDS

```
atgcctgagg aaacccagac ccaagaccaa ccgatggagg aggaggaggt tgagacgttc    60
gcctttcagg cagaaattgc ccagttgatg tcattgatca tcaatacttt ctactcgaac   120
aaagagatct ttctgagaga gctcatttca aattcatcag atgcattgga caaaatccgg   180
tatgaaagct tgacagatcc cagtaaatta gactctggga aagagctgca tattaacctt   240
ataccgaaca aacaagatcg aactctcact attgtggata ctggaattgg aatgaccaag   300
gctgacttga tcaataacct tggtactatc gccaagtctg ggaccaaagc gttcatggaa   360
gctttgcagg ctggtgcaga tatctctatg attggccagt tcggtgttgg tttttattct   420
gcttatttgg ttgctgagaa agtaactgtg atcaccaaac ataacgatga tgagcagtac   480
gcttgggagt cctcagcagg gggatcattc acagtgagga cagacacagg tgaacctatg   540
ggtcgtggaa caaaagttat cctacacctg aaagaagacc aaactgagta cttggaggaa   600
cgaagaataa aggagattgt gaagaaacat tctcagttta ttggatatcc cattactctt   660
tttgtggaga aggaacgtga taaagaagta agcgatgatg aggctgaaga aaaggaagac   720
aaagaagaag aaaaagaaaa agaagagaaa gagtcggaag acaaacctga aattgaagat   780
gttggttctg atgaggaaga agaaaagaag gatggtgaca agaagaagaa gaagaagatt   840
aaggaaaagt acatcgatca agaagagctc aacaaaacaa agcccatctg gaccagaaat   900
cccgacgata ttactaatga ggagtacgga gaattctata agagcttgac caatgactgg   960
gaagatcact tggcagtgaa gcatttttca gttgaaggac agttggaatt cagagccctt  1020
ctatttgtcc cacgacgtgc tccttttgat ctgtttgaaa acagaaagaa aaagaacaac  1080
atcaaattgt atgtacgcag agttttcatc atggataact gtgaggagct aatccctgaa  1140
tatctgaact tcattagagg ggtggtagac tcggaggatc tccctctaaa catatcccgt  1200
gagatgttgc aacaaagcaa aattttgaaa gttatcagga agaatttggt caaaaaatgc  1260
ttagaactct ttactgaact ggcggaagat aaagagaact acaagaaatt ctatgagcag  1320
ttctctaaaa acataaagct tggaatacac gaagactctc aaaatcggaa gaagctttca  1380
gagctgttaa ggtactacac atctgcctct ggtgatgaga tggtttctct caaggactac  1440
tgcaccagaa tgaaggagaa ccagaaacat atctattata tcacaggtga gaccaaggac  1500
caggtagcta actcagcctt tgtggaacgt cttcggaaac atggcttaga agtgatctat  1560
atgattgagc ccattgatga gtactgtgtc caacagctga aggaatttga ggggaagact  1620
ttagtgtcag tcaccaaaga aggcctggaa cttccagagg atgaagaaga gaaaaagaag  1680
caggaagaga aaaaaacaaa gtttgagaac ctctgcaaaa tcatgaaaga catattggag  1740
aaaaaagttg aaaaggtggt tgtgtcaaac cgattggtga catctccatg ctgtattgtc  1800
acaagcacat atggctggac agcaaacatg gagagaatca tgaaagctca agccctaaga  1860
gacaactcaa caatgggtta catggcagca aagaaacacc tggagataaa ccctgaccat  1920
```

-continued

SEQUENCE LISTING

```
tccattattg agaccttaag gcaaaaggca gaggctgata agaacgacaa gtctgtgaag  1980
gatctggtca tcttgcttta tgaaactgcg ctcctgtctt ctggcttcag tctggaagat  2040
ccccagacac atgctaacag gatctacagg atgatcaaac ttggtctggg tattgatgaa  2100
gatgacccta ctgctgatga taccagtgct gctgtaactg aagaaatgcc acccccttgaa  2160
ggagatgacg acacatcacg catggaagaa gtagactaa                         2199
```

Sequence I.D. No. 27-TEV protease recognition sequence
Glu Asn Leu Tyr Phe Gln Gly Sequence I.D. No. 28-base sequence for PCR sense primer of KRT10
GGTGGGAGTTATGGAGGCAG Sequence I.D. No. 29-base sequence for PCR antisense primer of KRT10
CGAACTTTGTCCAAGTAGGAAGC Sequence I.D. No. 30-base sequence for PCR sense primer of TGM1
CATCAAGAATGGCCTGGTCT Sequence I.D. 31-base sequence for FOR antisense primer of TGM1
CAATCTTGAAGCTGCCATCA Sequence I.D. No. 32-base sequence for PCR sense primer of IVL
TCCTCCAGTCAATACCCATCAG Sequence I.D. No. 33-base sequence for FOR antisense primer of IVL
CAGCAGTCATGTGCTTTTCCT

BIBLIOGRAPHY

The following references are specifically incorporated herein by reference in their entirety.

1. U.S. Pat. No. 7,951,396
2. USPub 20080213346
3. USPub 20070081963
4. Berke, R., et al., American Family Physician 86 (1): 35-42. July 2012.
5. Bolinder, J., et al., J Clin Endocrinol Metab. September; 57(3):455-61, 1983.
6. Bos J. D. et al., Experimental Dermatology, 2000, 9(3): 165-169.
7. Capristo C et al., Allergy, August; 59, Suppl 78:53-60, 2004.
8. Cheng C F et al., J Clin Invest., 121(11):4348-61, 2012.
9. Dhingra N et at, J Invest Dermatol., 133(10): 2311-4, 2013 October
10. Pockley, A. G., The Lancet, 362 (9382): pp. 469-476, 2003.
11. Schoop, V. M., J Inv. Derm., 112(3): 343-353, 1999.
12. Van Noort, J M, et al., J. Biochem. Cell Biol., 44 (10): pp. 1670-1679, 2012.
13. Subcutaneous Tissue. Medical Subject Headings (MeSH). NLM 5 Jun. 2013.
14. Paul G. Biochem., Paul G., Fox, Brian, *Protein Expr Purifi.,* 55(1): pp. 53-68, 2007.

What is claimed is:

1. A liposomal encapsulated polypeptide composition comprising HSP90a, HPf polypeptide, HPfΔC1, HPfΔC2, or a combination thereof.

2. The liposomal encapsulated polypeptide composition of claim 1 wherein the HPf polypeptide is HPfΔC1 or HPfΔC2.

3. The liposomal encapsulated polypeptide composition of claim 1, wherein the liposome is a nano-liposome having a particle size of about 50-500 nm, about 50-350 nm, or about 100-250 nm.

4. The liposomal encapsulated polypeptide composition of claim 1, wherein the polypeptide is HSP90a.

5. A topical formulation containing the composition of claim 1 for the treatment of a skin condition, wherein the skin condition is atopic dermatitis, wrinkles, dark spots, skin elasticity or skin aging, wherein said composition comprises a concentration of about 100 ng/ml to about 1 mg/ml of the HPf polypeptide, HPfΔC1, or HPfΔC2.

6. A topical formulation containing the composition of claim 1 for the treatment of subcutaneous fat accumulation, wherein said composition comprises a concentration of about 100 ng/ml to about 1 mg/ml of the HPf polypeptide, HPfΔC1, or HPfΔC2.

7. A skin condition preparation comprising the composition of claim 1, wherein the skin condition is atopic dermatitis, wrinkles, dark spots, skin elasticity or skin aging.

8. The skin condition preparation of claim 7 wherein the skin condition is obesity, cellulite, varicose veins of lower extremities with ulcer, lower body extremity edema, varicose veins, skin discoloration, venous eczema, scleroderma, inflammatory thrombus, skin ulcer, or chronic pain.

9. The liposome encapsulated polypeptide composition of claim 1 wherein the composition comprises a fusion protein comprising the HSP90a, HPf polypeptide, HPfΔC1 or HPfΔC2 polypeptide, and a fusion partner peptide.

10. The liposome encapsulated polypeptide composition of claim 9 wherein the fusion partner peptide is theoredoxin A, maltose binding protein (MBP) or human growth hormone (hGH).

11. The liposome encapsulated polypeptide composition of claim 1 wherein the HPf has a sequence of SEQ ID NO 1.

12. The liposome encapsulated polypeptide composition of claim 1 wherein the HPfΔC1 has a sequence of SEQ ID NO 20.

13. The liposome encapsulated polypeptide composition of claim 1 wherein the HPfΔC2 has a sequence of SEQ ID NO 21.

14. The liposome encapsulated polypeptide composition of claim 10 wherein the fusion partner peptide is theoredoxin A.

15. The liposome encapsulated polypeptide composition of claim 10 wherein the fusion partner peptide is maltose binding protein (MBP).

16. The liposome encapsulated polypeptide composition of claim 10 wherein the fusion partner peptide is human growth hormone.

17. The liposome encapsulated polypeptide composition of claim 10 wherein the fusion protein comprises the HPf-polypeptide and a fusion partner peptide theoredoxin A.

18. The liposome encapsulated polypeptide composition of claim 10 wherein the fusion protein comprises the HPf-polypeptide and a fusion partner peptide maltose binding protein.

19. The liposome encapsulated polypeptide composition of claim 10 wherein the fusion protein comprises the HPf-polypeptide and a fusion partner peptide human growth hormone.

20. The skin condition preparation of claim 7 comprising a concentration of about 100 ng/ml to about 1 mg/ml of the HPf polypeptide.

21. The skin condition preparation of claim 20 wherein the HPf polypeptide has a sequence of SEQ ID NO: 1.

* * * * *